(12) United States Patent
Fischer et al.

(10) Patent No.: US 11,041,215 B2
(45) Date of Patent: *Jun. 22, 2021

(54) PCR READY COMPOSITIONS AND METHODS FOR DETECTING AND IDENTIFYING NUCLEIC ACID SEQUENCES

(71) Applicant: Longhorn Vaccines and Diagnostics, LLC, Bethesda, MD (US)

(72) Inventors: Gerald W. Fischer, Bethesda, MD (US); Luke T. Daum, San Antonio, TX (US)

(73) Assignee: Longhorn Vaccines and Diagnostics, LLC, Bethesda, MD (US)

( * ) Notice: Subject to any disclaimer, the term of this patent is extended or adjusted under 35 U.S.C. 154(b) by 34 days.

This patent is subject to a terminal disclaimer.

(21) Appl. No.: 15/334,519

(22) Filed: Oct. 26, 2016

(65) Prior Publication Data

US 2017/0044595 A1  Feb. 16, 2017

Related U.S. Application Data

(63) Continuation-in-part of application No. 14/969,339, filed on Dec. 15, 2015, now Pat. No. 9,683,256, and
(Continued)

(51) Int. Cl.
*C12Q 1/68* (2018.01)
*C12Q 1/689* (2018.01)
(Continued)

(52) U.S. Cl.
CPC ......... *C12Q 1/689* (2013.01); *C12N 15/1003* (2013.01); *C12Q 1/6806* (2013.01);
(Continued)

(58) Field of Classification Search
CPC ..................................................... C12Q 1/68
(Continued)

(56) References Cited

U.S. PATENT DOCUMENTS 1,307,416 A   6/1919  Pine
2,697,373 A   12/1954 Siekmann et al.
(Continued)

FOREIGN PATENT DOCUMENTS

CN   1310235   8/2001
EA   6512      12/2005
(Continued)

OTHER PUBLICATIONS

Daum et al., Real-time RT-PCR assays for type and subtype detection of influenza A and B viruses, Influenza Other Respir Viruses. Jul. 2007; 1(4): 167-75. doi: 10.1111/j.1750-2659.2007.00024.X.*
(Continued)

*Primary Examiner* — Aaron A Priest
(74) *Attorney, Agent, or Firm* — Remenick PLLC

(57) ABSTRACT

The invention is directed to compositions and methods for isolating, detecting, amplifying, and quantitating pathogen-specific nucleic acids in a biological sample, and in particular PCR ready compositions that contain enzyme and are stable or long periods of time. The invention also provides diagnostic kits containing specific amplification primers, and labeled detection probes that specifically bind to the amplification products obtained therefrom. Also disclosed are compositions and methods for the isolation and characterization of nucleic acids that are specific to one or more pathogens, including for example Influenza virus and *Mycobacterium tuberculosis*, from a wide variety of samples including those of biological, environmental, clinical and/or veterinary origin.

46 Claims, 8 Drawing Sheets

Specification includes a Sequence Listing.

Related U.S. Application Data a continuation-in-part of application No. 14/527,281, filed on Oct. 29, 2014, now Pat. No. 9,598,737, and a continuation-in-part of application No. 14/048,905, filed on Oct. 8, 2013, now Pat. No. 9,481,912, said application No. 14/527,281 is a continuation of application No. 13/890,512, filed on May 9, 2013, now Pat. No. 9,365,904, said application No. 14/048,905 is a continuation-in-part of application No. 13/847,202, filed on Mar. 19, 2013, now Pat. No. 8,669,240, and a continuation-in-part of application No. 13/839,847, filed on Mar. 15, 2013, now abandoned, and a continuation-in-part of application No. 13/750,771, filed on Jan. 25, 2013, now Pat. No. 9,598,462, said application No. 13/847,202 is a continuation of application No. 13/632,272, filed on Oct. 1, 2012, now Pat. No. 8,415,330, said application No. 14/048,905 is a continuation of application No. PCT/US2012/035253, filed on Apr. 26, 2012, and a continuation-in-part of application No. 13/341,314, filed on Dec. 30, 2011, now Pat. No. 9,080,204, said application No. 13/632,272 is a continuation of application No. 13/332,204, filed on Dec. 20, 2011, now Pat. No. 8,293,467, said application No. 14/969,339 is a continuation of application No. 13/328,992, filed on Dec. 16, 2011, now Pat. No. 9,416,416, said application No. 14/048,905 is a continuation-in-part of application No. 13/094,809, filed on Apr. 26, 2011, now Pat. No. 8,652,782, said application No. PCT/US2012/035253 is a continuation-in-part of application No. 13/094,809, filed on Apr. 26, 2011, now Pat. No. 8,652,782, which is a continuation-in-part of application No. 12/916,263, filed on Oct. 29, 2010, now abandoned, said application No. 13/341,314 is a continuation-in-part of application No. 12/510,968, filed on Jul. 28, 2009, now Pat. No. 8,097,419, said application No. 13/328,992 is a continuation of application No. 12/426,890, filed on Apr. 20, 2009, now Pat. No. 8,080,645, said application No. 13/332,204 is a continuation of application No. 12/243,949, filed on Oct. 1, 2008, now Pat. No. 8,084,443, which is a continuation-in-part of application No. 11/844,933, filed on Aug. 24, 2007, now abandoned.

(60) Provisional application No. 61/897,015, filed on Oct. 29, 2013, provisional application No. 61/746,962, filed on Dec. 28, 2012, provisional application No. 61/737,250, filed on Dec. 14, 2012, provisional application No. 61/695,960, filed on Aug. 31, 2012, provisional application No. 61/646,060, filed on May 11, 2012, provisional application No. 61/644,876, filed on May 9, 2012, provisional application No. 61/616,676, filed on Mar. 28, 2012, provisional application No. 61/591,113, filed on Jan. 26, 2012, provisional application No. 60/976,728, filed on Oct. 1, 2007.

(51) Int. Cl.
*C12Q 1/6806* (2018.01)
*C12Q 1/686* (2018.01)
*C12N 15/10* (2006.01)

(52) U.S. Cl.
CPC ......... *C12Q 1/686* (2013.01); *C12Q 2600/16* (2013.01); *C12Q 2600/166* (2013.01)

(58) Field of Classification Search
USPC ........................................ 435/6.12
See application file for complete search history.

(56) References Cited

U.S. PATENT DOCUMENTS

| | | |
|---|---|---|
| 4,116,777 A | 9/1978 | Takatsy et al. |
| 4,196,265 A | 4/1980 | Koprowski et al. |
| 4,235,244 A | 11/1980 | Abele et al. |
| 4,315,073 A | 2/1982 | Brown et al. |
| 4,355,102 A | 10/1982 | Quash |
| 4,356,170 A | 10/1982 | Jennings et al. |
| 4,371,091 A | 2/1983 | Gelina |
| 4,372,945 A | 2/1983 | Likhite |
| 4,474,757 A | 10/1984 | Arnon et al. |
| 4,529,702 A | 7/1985 | Bryan |
| 4,554,101 A | 11/1985 | Hopp |
| 4,559,231 A | 12/1985 | Bjerre et al. |
| 4,578,770 A | 3/1986 | Mitani |
| 4,588,680 A | 5/1986 | Bucher et al. |
| 4,596,792 A | 6/1986 | Vyas |
| 4,599,230 A | 7/1986 | Milich et al. |
| 4,601,903 A | 7/1986 | Frasch |
| 4,608,251 A | 8/1986 | Mia |
| 4,634,664 A | 1/1987 | Oestberg |
| 4,634,666 A | 1/1987 | Engleman et al. |
| 4,668,476 A | 5/1987 | Bridgham et al. |
| 4,683,195 A | 7/1987 | Mullis et al. |
| 4,683,202 A | 7/1987 | Mullis |
| 4,707,450 A | 11/1987 | Nason |
| 4,744,982 A | 5/1988 | Hunter et al. |
| 4,746,490 A | 5/1988 | Saneii |
| 4,749,490 A | 6/1988 | Smyth et al. |
| 4,800,159 A | 1/1989 | Mullis et al. |
| 4,803,998 A | 2/1989 | Kezes et al. |
| 4,816,513 A | 3/1989 | Bridgham et al. |
| 4,883,750 A | 11/1989 | Whiteley et al. |
| 4,954,449 A | 9/1990 | Hunter et al. |
| 4,981,782 A | 1/1991 | Judd et al. |
| 4,996,143 A | 2/1991 | Heller et al. |
| 5,091,316 A | 2/1992 | Monthony et al. |
| 5,108,927 A | 4/1992 | Dorn |
| 5,136,019 A | 8/1992 | Judd et al. |
| 5,145,684 A | 9/1992 | Liversidge et al. |
| 5,149,653 A | 9/1992 | Roser |
| 5,163,441 A | 11/1992 | Monthony et al. |
| 5,168,039 A | 12/1992 | Crawford et al. |
| 5,182,109 A | 1/1993 | Tamura et al. |
| 5,186,898 A | 2/1993 | Bridgham et al. |
| 5,187,060 A | 2/1993 | Cerutti et al. |
| 5,234,809 A | 8/1993 | Boom et al. |
| 5,243,030 A | 9/1993 | Judd et al. |
| 5,252,458 A | 10/1993 | Liav et al. |
| 5,290,686 A | 3/1994 | Kendal et al. |
| 5,316,910 A | 5/1994 | Rota et al. |
| 5,370,998 A | 12/1994 | Crawford et al. |
| 5,399,363 A | 3/1995 | Liversidge et al. |
| 5,482,856 A | 1/1996 | Fell, Jr. et al. |
| 5,503,841 A | 4/1996 | Doyle et al. |
| 5,543,158 A | 8/1996 | Gref et al. |
| 5,545,555 A | 8/1996 | Racioppi et al. |
| 5,552,157 A | 9/1996 | Yagi et al. |
| 5,565,213 A | 10/1996 | Nakamori et al. |
| 5,565,322 A | 10/1996 | Heller |
| 5,567,434 A | 10/1996 | Szoka, Jr. |
| 5,571,511 A | 11/1996 | Fischer |
| 5,589,174 A | 12/1996 | Okuno et al. |
| 5,627,071 A | 5/1997 | Triva |
| 5,631,350 A | 5/1997 | Okuno et al. |
| 5,641,515 A | 6/1997 | Ramtoola |
| 5,648,215 A | 7/1997 | West |
| 5,656,016 A | 8/1997 | Ogden |
| 5,663,055 A | 9/1997 | Turner et al. |
| 5,679,356 A | 10/1997 | Bonnem et al. |
| 5,691,299 A | 11/1997 | Fabry |
| 5,697,899 A | 12/1997 | Hillman et al. |

(56) References Cited

U.S. PATENT DOCUMENTS

| | | |
|---|---|---|
| 5,702,944 A | 12/1997 | Racioppi et al. |
| 5,719,020 A | 2/1998 | Liav et al. |
| 5,736,333 A | 4/1998 | Livak et al. |
| 5,738,868 A | 4/1998 | Shinkarenko |
| 5,741,516 A | 4/1998 | Webb et al. |
| 5,766,841 A | 6/1998 | Liav et al. |
| 5,770,219 A | 6/1998 | Chiang et al. |
| 5,779,708 A | 7/1998 | Wu |
| 5,783,208 A | 7/1998 | Venkateshwaran et al. |
| 5,785,975 A | 7/1998 | Parikh |
| 5,795,582 A | 8/1998 | Wright |
| 5,795,587 A | 8/1998 | Gao et al. |
| 5,797,898 A | 8/1998 | Santini, Jr. et al. |
| 5,800,810 A | 9/1998 | Doyle et al. |
| 5,849,489 A | 12/1998 | Heller |
| 5,891,624 A | 4/1999 | Huang |
| 5,945,515 A | 8/1999 | Chomczynski |
| 5,955,074 A | 9/1999 | Fischer |
| 5,958,379 A | 9/1999 | Regenold et al. |
| 6,015,664 A | 1/2000 | Henrickson et al. |
| 6,033,673 A | 3/2000 | Clements |
| 6,060,068 A | 5/2000 | Doyle et al. |
| 6,136,585 A | 10/2000 | Ball et al. |
| 6,162,603 A | 12/2000 | Heller |
| 6,168,915 B1 | 1/2001 | Scholl et al. |
| 6,242,582 B1 | 6/2001 | Reece et al. |
| 6,280,928 B1 | 8/2001 | Scholl et al. |
| 6,306,404 B1 | 10/2001 | LaPosta et al. |
| 6,306,582 B1 | 10/2001 | Scholl et al. |
| 6,312,395 B1 | 11/2001 | Tripp et al. |
| 6,376,172 B1 | 4/2002 | Scholl et al. |
| 6,406,842 B2 | 6/2002 | Scholl et al. |
| 6,440,423 B1 | 8/2002 | Clements et al. |
| 6,451,325 B1 | 9/2002 | Van Nest et al. |
| 6,458,577 B1 | 10/2002 | Huang |
| 6,495,316 B1 | 12/2002 | Scholl et al. |
| 6,500,432 B1 | 12/2002 | Dalemans et al. |
| 6,503,745 B1 | 1/2003 | Chand et al. |
| 6,534,065 B1 | 3/2003 | Makin et al. |
| 6,572,866 B1 | 6/2003 | Torcia |
| 6,573,080 B2 | 6/2003 | Scholl et al. |
| 6,602,510 B1 | 8/2003 | Fikes et al. |
| 6,603,908 B2 | 8/2003 | Dallas et al. |
| 6,603,998 B1 | 8/2003 | King et al. |
| 6,610,293 B1 | 8/2003 | Fischer et al. |
| 6,610,474 B1 | 8/2003 | Huang |
| 6,627,396 B1 | 9/2003 | Swanson et al. |
| 6,632,432 B1 | 10/2003 | Fischer |
| 6,680,308 B1 | 1/2004 | Hassan |
| 6,689,363 B1 | 2/2004 | Sette et al. |
| 6,713,068 B1 | 3/2004 | Audonnet et al. |
| 6,720,409 B2 | 4/2004 | Okuno et al. |
| 6,734,292 B1 | 5/2004 | Omura et al. |
| 6,759,241 B1 | 7/2004 | Hone et al. |
| 6,780,421 B1 | 8/2004 | Haensler et al. |
| 6,793,928 B1 | 9/2004 | van Scharrenburg et al. |
| 6,811,971 B2 | 11/2004 | Klepp et al. |
| 6,855,321 B1 | 2/2005 | Rappuoli et al. |
| 6,875,600 B2 | 4/2005 | Scholl et al. |
| 6,881,835 B2 | 4/2005 | Bai et al. |
| 6,893,814 B2 | 5/2005 | Swanson et al. |
| 6,939,543 B2 | 9/2005 | Fischer et al. |
| 6,946,291 B2 | 9/2005 | Scholl et al. |
| 7,090,853 B2 | 8/2006 | Kapp et al. |
| 7,122,640 B2 | 10/2006 | Gjerde et al. |
| 7,223,409 B2 | 5/2007 | Nagata et al. |
| 7,279,162 B1 | 10/2007 | Fischer |
| 7,311,671 B2 | 12/2007 | Jung et al. |
| 7,351,413 B2 | 4/2008 | Page et al. |
| 7,357,936 B1 | 4/2008 | Garcon |
| 7,361,352 B2 | 4/2008 | Birkett et al. |
| 7,494,771 B2 | 2/2009 | Picard et al. |
| 7,541,194 B2 | 6/2009 | Mink et al. |
| 7,648,681 B2 | 1/2010 | Meyer et al. |
| 7,695,904 B2 | 4/2010 | Cawthon |
| 7,718,402 B2 | 5/2010 | Gayral et al. |
| 7,767,804 B2 | 8/2010 | Bair, Jr. et al. |
| 7,794,001 B2 | 9/2010 | Blackwell et al. |
| 8,080,645 B2 | 12/2011 | Fischer et al. |
| 8,084,443 B2 | 12/2011 | Fischer et al. |
| 8,097,419 B2 | 1/2012 | Fischer et al. |
| 8,293,467 B2 | 10/2012 | Fischer et al. |
| 2001/0021501 A1 | 9/2001 | Scholl et al. |
| 2001/0023065 A1 | 9/2001 | Lee |
| 2001/0034022 A1 | 10/2001 | Scholl et al. |
| 2001/0036628 A1 | 11/2001 | Scholl et al. |
| 2002/0054882 A1 | 5/2002 | Okuno et al. |
| 2002/0055094 A1 | 5/2002 | Reece et al. |
| 2002/0081567 A1 | 6/2002 | Henrickson et al. |
| 2002/0082395 A1 | 6/2002 | Fischer et al. |
| 2002/0169140 A1 | 6/2002 | Henrickson et al. |
| 2003/0119209 A1 | 6/2003 | Kaylor et al. |
| 2003/0138805 A1 | 7/2003 | Loffert |
| 2003/0143566 A1 | 7/2003 | Helftenbein |
| 2003/0203357 A1 | 10/2003 | Huang |
| 2003/0215796 A1 | 11/2003 | Scholl et al. |
| 2003/0219442 A1 | 11/2003 | Mikayama et al. |
| 2004/0009126 A1 | 1/2004 | Pilkiewicz et al. |
| 2004/0013673 A1 | 1/2004 | Fischer et al. |
| 2004/0071757 A1 | 4/2004 | Rolf |
| 2004/0082549 A1 | 4/2004 | Jomaa |
| 2004/0086849 A1 | 5/2004 | Shimasaki et al. |
| 2004/0101869 A1 | 5/2004 | Berg et al. |
| 2004/0126789 A1 | 7/2004 | Park et al. |
| 2004/0142319 A1 | 7/2004 | Yu et al. |
| 2004/0170965 A1 | 9/2004 | Scholl et al. |
| 2004/0214272 A1 | 10/2004 | La Rosa et al. |
| 2004/0223976 A1 | 11/2004 | Bianchi et al. |
| 2005/0009008 A1 | 1/2005 | Robinson et al. |
| 2005/0026147 A1* | 2/2005 | Walker ................. C12N 9/1252 435/6.1 |
| 2005/0042229 A1 | 2/2005 | Yang et al. |
| 2005/0090009 A1 | 4/2005 | Cormier et al. |
| 2005/0112656 A1 | 5/2005 | Iwaki |
| 2005/0169941 A1 | 8/2005 | Lees |
| 2005/0170334 A1 | 8/2005 | Mikayama et al. |
| 2005/0181357 A1 | 8/2005 | Peiris et al. |
| 2005/0187213 A1 | 8/2005 | Lang et al. |
| 2005/0227225 A1 | 10/2005 | Krevolin |
| 2005/0227269 A1 | 10/2005 | Lloyd, Jr. et al. |
| 2006/0002939 A1 | 1/2006 | Fischer et al. |
| 2006/0014185 A1 | 1/2006 | Ollikka et al. |
| 2006/0105468 A1 | 5/2006 | Winkler et al. |
| 2006/0121468 A1 | 6/2006 | Allnutt et al. |
| 2006/0134648 A1 | 6/2006 | Chou et al. |
| 2006/0147944 A1 | 7/2006 | Chomczynski |
| 2006/0286557 A1 | 12/2006 | Basehore et al. |
| 2007/0042358 A1 | 2/2007 | Shah |
| 2007/0078025 A1 | 4/2007 | Pepe |
| 2007/0102946 A1 | 5/2007 | Blackwell et al. |
| 2007/0172835 A1 | 7/2007 | McBride et al. |
| 2007/0196388 A1 | 8/2007 | Dowling et al. |
| 2007/0202497 A1 | 8/2007 | Renuart et al. |
| 2007/0202511 A1 | 8/2007 | Chen et al. |
| 2007/0286871 A1 | 12/2007 | Hickle et al. |
| 2008/0032921 A1 | 2/2008 | Alexander et al. |
| 2008/0044883 A1 | 2/2008 | Walker |
| 2008/0050737 A1 | 2/2008 | Arieli et al. |
| 2008/0064071 A1 | 3/2008 | Hogrefe |
| 2008/0069821 A1 | 3/2008 | Yang et al. |
| 2008/0074521 A1 | 3/2008 | Olsen |
| 2008/0075708 A1 | 3/2008 | Yu et al. |
| 2008/0078499 A1 | 4/2008 | Feeney |
| 2008/0107665 A1 | 5/2008 | Suckow et al. |
| 2008/0107687 A1 | 5/2008 | Poulet |
| 2008/0118531 A1 | 5/2008 | Hoffmann et al. |
| 2008/0139789 A1 | 6/2008 | Fischer |
| 2008/0145373 A1 | 6/2008 | Arumugham et al. |
| 2008/0145910 A1* | 6/2008 | Ward ................. C12Q 1/6848 435/188 |
| 2008/0181914 A1 | 7/2008 | Eichhorn |
| 2008/0260763 A1 | 10/2008 | Felgner et al. |
| 2009/0081202 A1 | 3/2009 | Fischer et al. |

(56) References Cited

U.S. PATENT DOCUMENTS

| | | | |
|---|---|---|---|
| 2009/0098527 A1* | 4/2009 | Fischer | C12Q 1/6806 435/5 |
| 2009/0233309 A1* | 9/2009 | Fischer | C12Q 1/6806 435/6.18 |
| 2009/0312285 A1 | 12/2009 | Fischer et al. | |
| 2010/0009343 A1 | 1/2010 | Fischer | |
| 2010/0043546 A1 | 2/2010 | Kandori et al. | |
| 2010/0055672 A1 | 3/2010 | Saghbini et al. | |
| 2010/0099150 A1* | 4/2010 | Fang | C07K 14/765 435/91.5 |
| 2010/0151447 A1 | 6/2010 | Cawthon | |
| 2010/0151477 A1 | 6/2010 | Cawthon | |
| 2010/0209927 A1 | 8/2010 | Menon | |
| 2010/0221822 A1 | 9/2010 | Fischer et al. | |
| 2010/0311739 A1 | 12/2010 | Gunaratnan et al. | |
| 2011/0159497 A1 | 6/2011 | Lee et al. | |
| 2011/0281754 A1 | 11/2011 | Fischer et al. | |
| 2012/0088231 A1 | 4/2012 | Fischer et al. | |
| 2012/0100529 A1 | 4/2012 | Fischer et al. | |
| 2012/0107799 A1 | 5/2012 | Daum | |
| 2012/0115126 A1 | 5/2012 | Fischer et al. | |
| 2012/0244527 A1 | 9/2012 | Trinh et al. | |

FOREIGN PATENT DOCUMENTS

| | | | |
|---|---|---|---|
| EP | 0313224 | 4/1989 | |
| EP | 320308 | 6/1989 | |
| EP | 0621339 | 10/1994 | |
| EP | 0675199 | 10/1995 | |
| EP | 0726316 | 8/1996 | |
| EP | 1081496 | 3/2001 | |
| EP | 2069487 B1 * | 3/2014 | C12Q 1/686 |
| JP | 2002501368 | 1/2002 | |
| JP | 2003052380 | 2/2003 | |
| JP | 2007519613 | 7/2007 | |
| JP | 2011508742 | 3/2011 | |
| RU | 2150281 | 6/2000 | |
| WO | WO 91/02740 | 3/1991 | |
| WO | WO1992003454 | 3/1992 | |
| WO | WO1992016619 | 10/1992 | |
| WO | WO1994009035 | 4/1994 | |
| WO | WO1994017106 | 8/1994 | |
| WO | WO 1995/08348 | 3/1995 | |
| WO | WO1997005248 | 2/1997 | |
| WO | WO 1997/46707 | 11/1997 | |
| WO | WO 1997/46712 | 11/1997 | |
| WO | WO 1997/46714 | 11/1997 | |
| WO | WO 98/40099 | 9/1998 | |
| WO | WO 1998/40099 | 9/1998 | |
| WO | WO01/16163 | 3/2001 | |
| WO | WO-0216639 A1 * | 2/2002 | C12Q 1/6853 |
| WO | WO2003026567 | 4/2003 | |
| WO | WO 2003/053462 | 7/2003 | |
| WO | WO2003053462 | 7/2003 | |
| WO | WO03/095646 | 11/2003 | |
| WO | WO2004/002451 | 1/2004 | |
| WO | WO2004002451 | 1/2004 | |
| WO | WO2004004658 | 1/2004 | |
| WO | WO 2004/043407 | 5/2004 | |
| WO | WO2004043407 | 5/2004 | |
| WO | WO2004055205 | 7/2004 | |
| WO | WO2004072270 | 8/2004 | |
| WO | WO2004084876 | 10/2004 | |
| WO | WO2005010186 | 2/2005 | |
| WO | WO 2005/042784 | 5/2005 | |
| WO | WO2005075642 | 8/2005 | |
| WO | WO2005085274 | 9/2005 | |
| WO | WO2006/041933 | 4/2006 | |
| WO | WO2006041933 | 4/2006 | |
| WO | WO 2006/138444 | 12/2006 | |
| WO | WO2006138444 | 12/2006 | |
| WO | WO 2007/051036 | 5/2007 | |
| WO | WO 2007/056266 | 5/2007 | |
| WO | WO2007051036 | 5/2007 | |
| WO | WO2007056266 | 5/2007 | |
| WO | WO 2007/091030 | 8/2007 | |
| WO | WO2007091030 | 8/2007 | |
| WO | WO2007133682 | 11/2007 | |
| WO | WO-2007133682 A2 * | 11/2007 | C12Q 1/702 |
| WO | WO 2008/079463 | 3/2008 | |
| WO | WO2008079463 | 7/2008 | |
| WO | WO1997005248 | 7/2009 | |
| WO | WO2009085355 | 7/2009 | |
| WO | WO 2009/085355 | 9/2009 | |
| WO | WO 1997005248 | 9/2009 | |
| WO | WO2010009398 | 1/2010 | |
| WO | WO-2010009398 A1 * | 1/2010 | C12Q 1/6846 |
| WO | WO 2010/066908 | 6/2010 | |
| WO | WO2010/123908 | 10/2010 | |
| WO | WO 2010123908 A1 | 10/2010 | |
| WO | WO-2011107003 A1 * | 9/2011 | G01N 33/582 |

OTHER PUBLICATIONS

Nolan et al., Quantification of mRNA using real-time RT-PCR, Nature Protocols, vol. 1, No. 3, pp. 1559-1582, Nov. 9, 2006.*
CN Examination Report Aug. 11, 2016.
Translation of CN Examination Report Aug. 11, 2016.
Nopvichai et al. (PCR detection of *Mycobacterium tuberculosis* in necrotising non-granulomatous lymphadenitis using formalin-fixed paraffin-embedded tissue: a study in Thai patients, J Clin Pathol. Sep. 2009;62(9):812-5).
Sigma-Aldrich (Buffer Reference Center, attached, available at inurl:http://www.sigmaaldrich.com/lifescience/corebioreagents/biologicalbuffers/learningcenter/bufferreferencecenter.html, accessed, Mar. 11, 2016).
EP Search Report for Application No. 15184002.2.
EP Opinion for Application No. EP15184002, dated Mar. 11, 2016.
CA Office Action for Application No. 2832499, dated Feb. 16, 2016.
CN Office Action for Application No. 201280031236, dated Feb. 5, 2016.
Wikibooks (Structural Biochemistry/Buffer, available at https://en.wikibooks.org/wiki/Structural_Biochemistry/Buffer, Jan. 27, 2009).
Ahern (Chapter 1 Outline, available at http://oregonstate.edu/instruct/bb450/spring14/lecture/introductionoutline.html, Sep. 30, 2006).
CN Office Action for Application No. 201280031236, dated May 14, 2015.
RU Office Action for PCT/US2012/035253.
JP Office Action for JP Application No. 2014-508562, dated Mar. 24, 2015.
Papagrigorakis, et al, "DNA examination of ancient dental pulp incriminates typhoid fever as a probable cause of the Plague of Athens," Int. J. Infect. Dis., 2006, 10(3), pp. 206-214.
Buys MH, Janse Van Rensburg LL, Mienie CMS, Barker N, Burgoyne PM, et al. "Applying AFLPs in Aizoaceae: The *Delosperma herbeum* complex as a case study," Biochem. Syst. Ecol., 2008, 36(2), pp. 92-100.
Anderson IC, Parkin PI, Campbell CD, "DNA- and RNA-derived assessments of fungal community composition in soil amended with sewage sludge rich in cadmium, copper and zinc," Soil Biol. Biochem., 2008, 40(9), pp. 2358-2365.
Liao J, Mitsuyasu T, Yamane T, et al., "Telomerase activity in oral and maxillofacial tumors," Oral Oncol., 2000, 36(4), pp. 347-352.
Thierry, et al., "Characterization of a *Mycobacterium tuberculosis* Insertion Sequence, IS6110, and Its Application in Diagnosis," Journal of Clinical Microbiology, vol. 28 No. 12, Dec. 1990, p. 2668-2673.
AU Exam Report for PCT/US2012/035253, dated Feb. 16, 2015.
Anderson, et al, "DNA and RNA-derived assessments of fungal community composition in soil amended with sewage sludge rich in cadmium, copper and zinc," Soil Biology and Biochemistry, Pegamon, Oxford, GB, vol. 40, No. 9, Sep. 1, 2008.
Liao, J et al, "Telomerase activity in oral and maaxillofacial tumors," Oral Oncology, Elsevier Science, Oxford, GB, vol. 36, No. 4, Jul. 1, 2000.
Daum, L, et al, "A clinical specimen collection and transport medium for molecular diagnostic and genomic applications," Epi-

(56) References Cited

OTHER PUBLICATIONS demiology and Infection, Cambridge University Press, Cambridge, GB, vol. 139, No. 11, Dec. 16, 2010.
Daum, L. et al, "A rapid, collection-to-detection PCR system of the universal detection of *Mycobacterium tuberculosis*," Jun. 29, 2011, pp. 1-1.
Papagrigorakis, M. et al, "DNA examination of ancient dental pulp incriminates typhoid fever as a probable cause of the plague of Athens," International Journal of Infectious Diseases, Hamilton, CA, vol. 10, No. 3, May 1, 2006.
Buys, et al, "Applying AFLPs in Aizoaceae: the Delosperma herbeum complex as a case study," Biochemical Systematics and Ecology, Pergamon Press, GB, vol. 36, No. 2, Dec. 13, 2007.
EP Exam Report for PCT/US2012/035253, dated Feb. 13, 2015.
Austalian Exam Report for Application No. 2012239385, dated Oct. 9, 2013.
Austalian Exam Report for Application No. 2012211365, dated Oct. 9, 2013.
Max, et al Reliability of PCR-based detection of occult tumour cells: lessons from real-time RT-PCR.
EP Search Report for Application No. 13175959, dated Nov. 18, 2013.
PCT Search and Patentability Report for PCT/US2013/077038, dated Mar. 10, 2014.
CA Office Action for CA Application No. 2701168, dated Mar. 4, 2014.
PCT Search Report for PCT/US13/32354, dated May 31, 2013.
Chinese Office Action for Application No. 201080028416.4.
Chinese Search Report for Application No. 201080028416.4.
IL Exam Report for PCT/US2007/078025, dated Mar. 7, 2013.
EPO Exam Report for EP12180376, dated Feb. 8, 2013.
Canadian Office Action for application No. 2759028, dated Apr. 12, 2013.
Canadian Office Action for application No. 2697373, dated Feb. 19, 2013.
Fouchier, et al., "Characterization of Novel Influenza A Virus Hemagglutinin Subtype (H16) Obtained from Black-Headed Gulls," J. Virol. 79(5):2814-2822 (2005).
Daum, et al., Abstract and Poster—"Development of a Real Time Reverse-Transcription PCR (RRT-PCR) Assay for Detection of Influenza A H1N1 2009 From Clinical Respiratory Specimens," Pediatric Infectious Disease Conference ESPID, Nice, France, May 5-8, 2009.
Daum L.T., et al., "Molecular Analysis of Isolates From Influenza B Outbreaks in the U.S. and Nepal, 2005," Arch. of Virol., 151:1863-1874 (2006).
Longhorn Vaccines & Diagnostics, "PrimeStore and PrimeMix," advertisement pamphlet.
Daum, et al., "Real-Time RT-PCR Detection of Influenza Virus within Symptomatic and Asymptomatic Family Members," Longhorn Vaccines & Diagnostics TechNotes Newsletter.
USB Corp., "USB Taq PCR Master Mix in qPCR," Tech Tip 207 (2005).
World Health Organization, "CDC protocol of realtime RTPCR for influenza A (H1N1)," Apr. 28, 2009.
PCT Patentability Report for PCT/US2012/35253, dated Sep. 21, 2012.
Taiwan Office Action dated Aug. 20, 2012.
"Development of an Internal Positive Control for Rapid Diagnosis of Avian Influenza, etc.", A.Das, et al., Journal of Clinical Microbiology, Sep. 2006, vol. 44, No. 9, pp. 3065-3073.
De Moreau de Gerbehaye, A.I. et al., "Stable Hepatitis C Virus RNA Detection by RT-PCR During Four Days Storage," BioMed Central, BMC Infectious Diseases, 2:22 (2002).
"Evaluation of PCR Testing of Ethanol-Fixed Nasal Swab Specimens, etc." A.Krafft, et al., Journal of Clinical Microbiology, Apr. 2005, vol. 43, No. 4, pp. 1768-1775.
"Abstracts—27th Annual Meeting for the European Society for Paediatric Infectious Disease, Brussels, Belgium, Jun. 9-13, 2009," The Ped. Infect. Dis. J., 28(6):e1, e75, e229 (Jun. 2009).

"AgPath-ID One-Step RT-PCR Kit," Applied Biosystems, available at http://www.abion.com/techlib/prot/bp_1005.pdf (last visited Aug. 24, 2009).
Lin, B., et al., "Broad-Spectrum Respiratory Tract Pathogen Identification Using Resequencing DNA Microarrays." Genome Res., 16:527-35 (2006).
Buck et al. BioTechniques vol. 27, pp. 528-536, Sep. 1999.
Wolff, C. et al, "Single-Tube Nested PCR With Room-Temperature-Stable Reagents," Cold Spring Harbor Laboratory Press, PCR Methods and Appl., 4:376-79 (1995).
Schultz, C.L., et al., "A Lysis, Storage, and Transportation Buffer for Long-Term, Room-Temperature Preservation of Human Clinical Lymphoid Tissue Samples Yielding High Molecular Weight Genomic DNA Suitable for Molecular Diagnosis," Am. J. Clin. Pathol., 111(6):748-52 (1999).
Characterization of Novel Influenza 2005.
"Collecting, Preserving, Shipping Specimens for the Diagnosis of Avian Influenza (H5N1) Virus Infection: Guide for Field Operations," WHO/CDS/EPR/ARO/2006.1 (2006).
Daum, et al., Abstract—"A Molecular Transport Medium (MTM) for Pathogen Inactivation, Ambient Transport and Preservation of RNA from Clinical Samples," ICAAC, Boston, MA, Sep. 12-15, 2010.
Daum, et al., Abstract and Poster—"Development of a Real Time Reverse-Transcription PCR (RRT-PCR) Assay for Detection of Influenza A H1N1 2009 from Clinical Respiratory Specimens," Pediatric Infectious Disease Conference ESPID, Nice, France, May 5-8, 2010.
De Silva at al. Influenza A virus (A/Nonthaburi/102/2009(H1N1)) segment 4 hemagglutinin (HA) gene, partial cds. Genbank Accession No. GQ 132184.1, submitted May 9, 2009.
Spackman, E., et al., "Development of a Real-Time Reverse Transcriptase PCR Assay for Type A Influenza Vrius and the Avian H5 and H7 Hemagglutinin Subtypes," J. Clinic. Mirobiol., 40(9): 3256-60 (2002).
Hindiyeh et al. Journal of Clinical Microbiology, vol. 43, No. 2, pp. 589-595, Feb. 2005.
J. Mahoney et al., "Multiplex RT-PCR for detecting nineteen respiratory viruses," Journal of Clinical Virology, vol. 36, Jan. 1, 2006, p. S9.
"Adamantane Resistance Among Influenza, etc.", JAMA, Feb. 22, 2006, vol. 295, No. 8, pp. 891-894.
Jamie A. Blow et al., "Viral nucleic acid stabilization by RNA extraction reagent," Journal of Virological Methods, 150 (2008), Feb. 4, 2008, pp. 41-44.
"KOD Hot Start DNA Polymerase," Novagen, available at http://www.emdbiosciences.com/ProductDisplay.asp?catno=71086 (last visited Aug. 24, 2009).
Kutyavin et al. 3'-Minor groove binder-DNA probes increase sequence specificity at PCR extension temperatures. Nucleic Acid Res. (2000) vol. 28, No. 2, pp. 655-661.
"Genetic and Antigenic Analysis of the First A/New Calendonia, etc.", L.Daum, et al., Emerging Infectious Diseases, vol. 8, No. 4, Apr. 2002, pp. 408-412.
Canas, L.C., "Clinical Laboratory: Selection, Collection and Transport of Specimens for Viral Cultures." Department of the Air Force, Air Force Institute of Operational Health (AFIOH), Epidemiological Surveillance Division, SDE O1 44/5001, Virol. Proc. Man., 1-8 (2005).
Daum, L.T. et al., "Real-Time RT-PCR Assays for Type and Subtype Detection of Influeza A and B Viruses," Influenza & Other Resp. Viruses 1(4): 167-75 (2007).
Daum, L.T., et al., "Abstract—Quantification of Influenza A Virus From Nasal and Lung Tissue of Cotton Rats Using Real-Time RT-PCR and Culture," 26th Annual Meeting of the European Society for Pediatric Infectious Diseases, Graz, Austria (2008).
Daum, L.T., et al., "Abstract—Development and Clinical Evaluation of Rapid Real-Time RT-PCR Assays for Detection of Influenza A and B Viruses," 26th Annual Meeting of the European Society for Pediatric Infectious Diseases, Graz, Austria (2008).
Daum, L.T., et al., "Poster—A Novel Specimen Collection Solution for Molecular Diagnostic Applications," the Pediatric Academic Societies (PAS) Annual Meeting, Honolulu, HI (2008).

(56) References Cited

OTHER PUBLICATIONS

Daum, L.T., et al., "Poster—A Rapid, Simplified Collection-to-Detection System for Typing and Subtyping Influenza Viruses Using Real-Time RT-PCR and Culture," American Society for Microbiology (ASM) Conference on Emerging Technologies of Medical Importance for the Diagnosis of Infectious Diseases and the Detection of Pathogenic Microbes, Beijing, China (2008).

Daum, L.T., et al., "Poster—Real-Time RT-PCR Detection of Influenza A Virus in Asymptomatic Culture-Negative Cotton Rats," The Pediatric Academic Societies (PAS) Annual Meeting, Honolulu, HI (2008).

Daum, L.T., et al., "A Rapid, Single-Step Multiplex Reverse Transcription-PCR Assay for the Detection of Human H1N1, H3N2 and B Influenza Viruses." J. of Clinic. Virol., 25(3): 345-50 (2002).

Daum, L.T., et al., "Real-Time RT-PCR Detection of Influenza Virus Within Symptomatic and Asymptomatic Family Members," The 48th Annual IDSA/ICAAC, Washington D.C. (2008).

Lowe et al. A computer program for selection of oligonucleotide primers for polymerase chain reactions. Nucleic Acids Research (1990) vol. 18, No. 7, pp. 1757-1761.

Luke T. Daum et al., "Detection and Molecular Characterization of Clinical Influenza A and B Viruses from Original Nasal Wash Specimens Preserved in PrimeStore," (2008).

Luke T. Daum et al., "Portugal Meeting Poster (Introduction, Materials, and Methods, Results, Discussion)," (2008).

"Luminex Confirms Effectiveness of xTAG Respiratory Viral Panel for Swine Flu Surveillance," Medical News Today, available at http://www.medicalnewstoday.com/printerfriendlynews.php?newsid=148498 (May 1, 2009).

"Luminex Receives FDA Clearance for an Update to the xTAG Respiratory Panel Insert Package Insert to Include Data from Two New Publications on 2009 Influenza A/H1N1," available at http://phx.corporate-ir.net/phoenix.zhtml?c=79403&p=irol-newsArticle&ID=1307416&highlight= (Jul. 14, 2009).

Borns, M. et al., "Most Accurate PCR Enzyme Inproved With Hot Start Feature," Biocompare, available at http://www.biocompare.com/technicalarticle/212/Most-Accurate-PCR-Enzyme-Improved-With-Hot-Start-Feature-from-Startagene.html (last visited Aug. 24, 2009).

Denhart, M., and Doraiswamy, V., "Master Your PCR Domain!" Promega Notes, 78: 9-12 (2001).

Master Your PCR Domain.

"Tools of Biochemistry 5A—Ways to Isolate and Purify Proteins and Other Macromolecules", Matthews, et al., Biochemistry, Second Edition, 1996, pp. 152-155.

Tortora, et al., "Tools of Biochemistry 5A—Ways to Isolate and Purify Proteins and Other Macromolecules," Microbiology—An Introduction, pp. 152-155, 4th Ed., The Benjamin/Cummings Publishing Company, Inc., United States (1992).

Matthews, et al., "Immunofluorescence and Fluorescent Antibody Techniques," Biochemistry, pp. 461-463, 2nd Ed., The Benjamin/Cummings Publishing Company, Inc., United States (1996).

Morre, et al., "RNA Amplification by Nucleic Acid Sequence-Based Amplification with an Internal Standard Enables Reliable Detection of Chlamydia trachomatis in Cervical Scrapings and Urine Samples," J. of Clinical Microbiol, 34(12): 3108-3114 (1996).

http://www.ncbi.nlm.nih.gov/genomes/Flu/SwineFlu2009.html. NCBI Influenza Virus Resource "CLE I. GenBank Sequence from Pandemic (H1N1) 2009 Viruses". 1237 pages.

Pheng, O.C. et al., "Temperature Related Storage Evaluation of an RT-PCR Test Kit for the Detection of Dengue Infection in Mosquitoes," (Research Note), Tropical Biomedicine, 22(1):73-6 (2005).

"Single-Step Method of RNA Isolation by Acid Guanidinium, etc.", P. Chomczyniski, et al., Analytical Biochemistry 162, 1987, pp. 156-159.

Pamphlet—"Prime PCR System"—Longhorn Vaccines & Disagnostics.

"PCR Optimization: Reaction Conditions and Components," Applied Biosystems, Part No. 4371091, Revision C, pp. 1-6 available at http://www.appliedbiosystems.com/cms/groups/mcb_marketing/documents/generaldocuments/cms_042520.pdf (last visited Aug. 24, 2009).

"PCR-Ready Clear Supreme," Syntezza Bioscience Ltd., available at http://www.syntezza.com/egt/PCR-Ready_Clear Supreme.pdf (2006).

European Patent Office, "PCT Notification of Transmittal of the International Search Report and the Written Opinion of the International Searching Authority or the Declaration, PCT International Search Report, PCT Written Opinion of the International Searching Authority—Application No. PCT/US2007/078025," dated Nov. 13, 2008, 10 pages, Munich.

European Patent Office, "PCT Notification of Transmittal of the International Search Report and the Written Opinion of the International Searching Authority—Application No. PCT/US2008/078499," dated Aug. 4, 2009, 13 pages.

Ramanujam, R. et al., "Room-Temperature-Stable PCR Reagents," Cold Spring Harbor Laboratory Press, PCR Methods and Appl., 3:75-76 (1993).

Bright, R.A., et al., "Adamantane Resistance Among Influenza A Viruses Isolated Early During the 2005-2006 Influenza Season in the United States," JAMA, 295(8):891-4 (Feb. 22, 2006).

Fouchier, R.A.M. et al., "Characterization of a Novel Influenza A Virus Hemagglutinin Subtype (H16) Obtained From Black-Headed Gulls," J. of Virol. 79(5):2814-22 (Mar. 2005).

"R.A.P.I.D System," Idaho Technology Inc., available at http://www.idahotech.com/RAPID/Rapid-Water.html (last visited Aug. 24, 2009).

Magari, R.T., Assessing shelf life using real-time and accelerated stability tests, BioPharm Nov. 2003.

Rosenstraus, et al., "An Internal Control for Routine Diagnostic PCR: Design, Properties, and Effect on Clinical Performance," J. of Clinical Microbial, 36(1): 191-197 (1998).

Blacksell, S.D. et al., "The Effect of Sample Degradation and RNA Stabilization on Classical Swine Fever Virus RT-PCR and ELISA methods," J. Virol. Methods, 118(1):33-7 (2004).

"Single Tube PCR Kit Manual," Takara Bio Inc., Cat #RR021, V.02.09, pp. 1-6 available at http://www.takara-bio.us/files/manuels/TAK_RR021_TM.pdf (last visited Aug. 24, 2009).

"Taq PCR Master Mix (2x)," USB Corp., (2007).

"TechNotes Newsletter," Applied Biosystems, 14(4):1-37 (2007).

"Immunoflourescence and Fluorescent-Antibody Techniques", Tortora, et al., Microbiology—An Introduction, Fourth Edition, 1992, pp. 461-463.

"USB Taq PCR Master Mix in qPCR," USB Corporation, Tech Tips, 207 (2005).

Wiecek, A., "Pocket PCR: The Whole Chain Reaction in His Hand," Biotechniques.com, Oct. 26, 2010.

Wang, Z., et al., "Identifying Influenza Viruses with Resequencing Microarrays," Emerg. Infect. Dis. 12(4):638-46 (2006).

Danila Valmori et al. "Use of human universally antigenic tetanus toxin T cell epitopes as carriers for human vaccination" Journal of Immunology Jul. 15, 1992.

PCT Search Report for PCT/US2008/074521 dated Feb. 13, 2009.
PCT Written Opinion for PCT/US2008/074521 dated May 3, 2009.
PCT Search Report for PCT/US10/43546 dated Nov. 16, 2010.
PCT Search Report for PCT/US10/31716 dated Jul. 28, 2010.
PCT Written Opinion for PCT/US10/31716 dated Oct. 25, 2011.

De Folette et al. Vaccine 2006, Jun. 12, vol. 24, No. 44-46, pp. 6597-6601.

Galarza et al. Viral Immunity 2005, vol. 18, No. 2, pp. 365-372.

Arend et al. Infection and Immunity, 2000, vol. 68, No. 6, pp. 3314-3321.

Geysen, et al., "Use of Peptide Synthesis to Probe Viral Antigens for Epitopes to a Resolution of a Single Amino Acid," Proc. Natl. Acad. Sci., 81, pp. 3998-4002 (1984).

Tolman, et al., "Cyclic V3-Loop Related HIV-1 Conjugate Vaccines," Int. J. Peptide Protein Res., 41, pp. 455-466 (1993).

Conley, et al., "Immunogenicity of Synthetic HIV-1 Gp120 V3-Loop Peptide-Conjugate Immunogens," Vaccine, 12(5), pp. 445-451 (1994).

Schneider, et al., "Induction of CD8+T Cells Using Heterologous Prime-Boost Immunisation Strategies," Immunol. Rev., 170, pp. 29-38 (1999).

(56) References Cited

OTHER PUBLICATIONS

Tanghe, et al., "Improved Immunogenicity and Protective Efficacy of a Tuberculosis DNA Vaccine Encoding Ag85 by Protein Boosting," Infect. and Immun., 69(5), pp. 3041-3047 (2001).
Gonzalo, et al., "A Heterologous Prime-Boost Regime Using DNA and Recombinant Vaccinia Virus Expressing the Leishmania infantum P36/LACK Antigen Protects BALB/c Mice from Cutaneous Leishmaniasis," Vaccine, 20, pp. 1226-1231 (2002).
Meyer, et al., "Complement-Mediated Enhancement of Antibody Function for Neutralization of Pseudotype Virus Containing Hepatitis C Virus E2 Chimeric Glycoprotein," J. of Virol., 76(5) pp. 2150-2158 (2002).
Robinson, "New Hope for an AIDS Vaccine," Nat. Rev. Immunol., 2, pp. 239-250 (Apr. 2002).
Lu, et al., "Multiepitope Trojan Antigen Peptide Vaccines for the Induction of Antitumor CTL and Th Immune Responses," J. of Immunol., 172, pp. 4575-4582 (2004).
Westerfield, et al., "Peptides Delivered by Immunostimulating Reconsituted Influenza Virosomes," J. of Peptide Sci., 11(11), pp. 707-712 (2005).
Gerhard, et al., "Prospects for Universal Influenza Virus," Emerging Infectious Diseases, 12(4), pp. 569-574 (Apr. 2006).
Luo, "Structural Biology: Antiviral Drugs Fit for a Purpose," Nature, 443, pp. 37-38 (Sep. 1, 2006).
PepTcell Ltd., "Technology," http://www.peptcell.com/technology.aspx (2007).
Stoloff, et al., "Synthetic Multi-Epitope Peptides Idenitifed in Silico Induce Protective Immunity Against Multiple Influeza Serotypes," Eur. J. of Immunol., 37(9), pp. 2441-2449 (Aug. 2, 2007).
Depla, et al., "Rational Design of a Multiepitope Vaccine Encoding T-Lymphocyte Epitopes for Treatment of Chronic Hepatitis B Virus Infections," J. of Virol., 82(1), pp. 435-450 (Jan. 2008).
Chien et al. J. Clin. Microbiol. 1999, vol. 37, No. 5, 1393-1397.
Ishioka et al. J. Immunol. vol. 162, pp. 3915-3925.
Lederman et al. Molecular Immunology 1991, vol. 28, No. 11, pp. 1171-1181.
PCT Search Report for PCT/US2007/078025 dated Oct. 28, 2008.
PCT Written Opinion for PCT/US2007/078025 dated Mar. 17, 2009.
PCT Search Report for PCT/US2008/078499 dated Jul. 23, 2009.
CA Office Action for PCT/US2007/078025, dated Jan. 4, 2011.
EPO Exam Report for PCT/US2007/078025, dated Dec. 30, 2011.
EPO Exam Report for PCT/US2007/078025, dated Aug. 26, 2010.
EPO Exam Report for PCT/US2007/078025, dated Jul. 6, 2009.
EPO Exam Report for PCT/US2007/078025, dated May 18, 2009.
AU Exam Report for PCT/US2007/078025, dated Nov. 19, 2010.
IL Exam Report for PCT/US2007/078025, dated Mar. 16, 2011.
NZ Exam Report for PCT/US2007/078025, dated Jul. 7, 2010.
Israel Office Action of Jul. 19, 2012.
EPO Supplementary Search Report for PCT/US10/31761, dated Jul. 13, 2012.
PCT Written Opinion for PCT/US2008/078499, dated Jul. 4, 2010.
"Monolithic Silica Extraction Tips for Sample Preparation," CP-Analytica, available at http://cp-analytica (last visited Oct. 25, 2010).
Barnard, et al., "Suitability of new chlamydia transport medium for transport of herpes simplex virus," J. of Clin. Microbiol., 24(5): 692-695 (1986).
Eroglu, et al., "Successful cyropreservation of mouse oocytes by using low concentrations of trehalose and dimethylsylfoxide," Biol. of Rep. 80:70-78 (2009).
Gelmi, et al., "Bacertial survival in different transport media," European Congress of Clinical Microbiology and Infectious Diseases (ECCMID), May 28-31, 2000 (poster).
Higashiyama, T., "Novel functions and applications of terhalose," Pure Appl. Chem. 74(7): 1263-1269.
H1N1 RTPCR Primer/Probe Sets, Intergrated DNA Technologies—H1N1, available at http://www.idtdna.com/catalog/h1n1/page1.aspx.
Johnson, F.B., "Transport of viral specimens," Clin. Microbiol. Rev. 3(2): 120-131 (1990).
Sponseller, et al., "Influenza A pandemic (H1N1) 2009 virus infection in domestic cat," Emerg. Infect. Dis. (e-publication) (2010).
PCT Patentability Report for PCT/US2010/043546, dated Jan. 31, 2012.
PCT Search Report and Patentability Report for PCT/US2008/074521, dated Mar. 2, 2010.
Miyazaki, et al., "Development of a monolithic silica extraction top for the analysis of proteins," J. Chromatogr. A., 1043(1): 19-25 (2004) [abstract only].
CA Office action for PCT/US08/78499, dated Mar. 29, 2012.
De Folette et al. Vaccine Jun. 12, 2006, vol. 24, No. 44-46, pp. 6597-6601.
Israel Office Action dated Jul. 19, 2012.
CA Office Action for PCT/US2008/078499, dated Mar. 29, 2012.
Henke et al., Nucleic Acids Research 25(19): 3957-3958 (1997).
Yue et al., Diagnostic Microbiology and Infectious Disease, 48(1): 47-54 (2004).
EP Search Report for Application No. 1277650937 dated Oct. 25, 2016.
IL Examination Report for Application No. 228971 dated Nov. 28, 2018 (not translated).
IN Examination Report for Application No. 9740/DELNP/2013 dated Aug. 9, 2018.
CA Examination Report for Application No. 2,832,499 dated Dec. 7, 2018.
Marenco et al., "Fluorescent-Based Genetic Analysis for a Microfluidics Device" Defense Research and Development Canada, PWGS Canada Contract No. W7702-00-R849/001/EDM Final Report, Period from Feb. 1, 2000 to Mar. 31, 2004, dated Mar. 2004.
EP Search and Examination Report for Application No. 19166149.5 dated Sep. 12, 2019.
Manolis J. Papagrogorakis et al., "DNA Examination of Ancient Dental Pulp Incriminates Typhoid Fever as a Probable Cause of the Plague of Athens" International Society of Infectious Disease 10:206-214, 2006.
Ian C. Anderson et al., "DNA- and RNA-Derived Assessments of Fungal Community Compositions in Soil Amended with Sewage Sludge Rich in Cadmium, Copper and Zinc" Soil Biology & Biochemistry 40:2358-2365, 2008.
M.H. Buys et al., "Applying AFLPs in Aizoaceae: The Delospermia Herbeum Complex as a Case Study" Biochemical Systematics and Ecology 36:92-100, 2008.
Examination Report for CA Application No. 2,832,499 dated Feb. 28, 2020.

* cited by examiner

SEQUENCE LISTING

<160> NUMBER OF SEQ ID NOS: 162

<210> SEQ ID NO 1
<211> LENGTH: 180
<212> TYPE: DNA
<213> ORGANISM: Mycobacterium tuberculosis

<400> SEQUENCE: 1

```
gtcccgccga tctcgtccag cgccgcttcg gaccaccagc acctaaccgg ctgtgggtag      60
cagacctcac ctatgtgtcg acctgggcag ggttcgccta cgtggccttt gtcaccgacg     120
cctacgtcgc aggatcctgg gctggcgggt cgcttccacg atggccacct ccatggtcct     180
```

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 2

```
ctcgtccagc gccgcttc                                                     18
```

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 3

```
acaaaggcca cgtaggcga                                                    19
```

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4

```
accagcacct aaccggctgt gggta                                             25
```

```
<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 5
accagcacct aaccggct                                                   18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 6
accgacgcct acgtcgca                                                   18

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
agggttcgcc tacgtggcct ttgt                                            24

<210> SEQ ID NO 8
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
gggatcgtat aatcgtcgtg cagtcagtcc ctcggttaaa gtctcgagtc gctctgtcaa     60
aatatccgta ccgtagtcga tgcgagcgag tccgatcagt ccaggtttca aagtcaaatg    120
acta                                                                 124

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 9
gtgcagtcag tccctcggtt a                                               21

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 10
```
ttgactttga aacctggact gatc                                              24

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
aaatatccgt accgtagtcg                                                   20

<210> SEQ ID NO 12
<211> LENGTH: 1623
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(500)
<223> OTHER INFORMATION: a, c, t, g, unknown or other
<220> FEATURE:
<221> NAME/KEY: misc_feature
<222> LOCATION: (1)..(500)
<223> OTHER INFORMATION: This region may encompass 0-500 nucleotide
      wherein some positions may be absent
<220> FEATURE:
<221> NAME/KEY: modified_base
<222> LOCATION: (524)..(1023)
<223> OTHER INFORMATION: a, c, t, g, unknown or other
<220> FEATURE:
<221> NAME/KEY: misc_feature
<222> LOCATION: (524)..(1023)
<223> OTHER INFORMATION: This region may encompass 0-500 nucleotide
      wherein some positions may be absent
<220> FEATURE:
<221> NAME/KEY: modified_base
<222> LOCATION: (1124)..(1623)
<223> OTHER INFORMATION: a, c, t, g, unknown or other
<220> FEATURE:
<221> NAME/KEY: misc_feature
<222> LOCATION: (1124)..(1623)
<223> OTHER INFORMATION: This region may encompass 0-500 nucleotide
      wherein some positions may be absent

<400> SEQUENCE: 12
nnnnnnnnnn nnnnnnnnnn nnnnnnnnnn nnnnnnnnnn nnnnnnnnnn nnnnnnnnnn       60
nnnnnnnnnn nnnnnnnnnn nnnnnnnnnn nnnnnnnnnn nnnnnnnnnn nnnnnnnnnn      120
nnnnnnnnnn nnnnnnnnnn nnnnnnnnnn nnnnnnnnnn nnnnnnnnnn nnnnnnnnnn      180
nnnnnnnnnn nnnnnnnnnn nnnnnnnnnn nnnnnnnnnn nnnnnnnnnn nnnnnnnnnn      240
nnnnnnnnnn nnnnnnnnnn nnnnnnnnnn nnnnnnnnnn nnnnnnnnnn nnnnnnnnnn      300
nnnnnnnnnn nnnnnnnnnn nnnnnnnnnn nnnnnnnnnn nnnnnnnnnn nnnnnnnnnn      360
nnnnnnnnnn nnnnnnnnnn nnnnnnnnnn nnnnnnnnnn nnnnnnnnnn nnnnnnnnnn      420
nnnnnnnnnn nnnnnnnnnn nnnnnnnnnn nnnnnnnnnn nnnnnnnnnn nnnnnnnnnn      480
nnnnnnnnnn nnnnnnnnnn tattaatacg actcactata gggnnnnnnn nnnnnnnnnn      540
nnnnnnnnnn nnnnnnnnnn nnnnnnnnnn nnnnnnnnnn nnnnnnnnnn nnnnnnnnnn      600
nnnnnnnnnn nnnnnnnnnn nnnnnnnnnn nnnnnnnnnn nnnnnnnnnn nnnnnnnnnn      660
nnnnnnnnnn nnnnnnnnnn nnnnnnnnnn nnnnnnnnnn nnnnnnnnnn nnnnnnnnnn      720
nnnnnnnnnn nnnnnnnnnn nnnnnnnnnn nnnnnnnnnn nnnnnnnnnn nnnnnnnnnn      780

```
nnnnnnnnnn nnnnnnnnnn nnnnnnnnnn nnnnnnnnnn nnnnnnnnnn nnnnnnnnnn      840
nnnnnnnnnn nnnnnnnnnn nnnnnnnnnn nnnnnnnnnn nnnnnnnnnn nnnnnnnnnn      900
nnnnnnnnnn nnnnnnnnnn nnnnnnnnnn nnnnnnnnnn nnnnnnnnnn nnnnnnnnnn      960
nnnnnnnnnn nnnnnnnnnn nnnnnnnnnn nnnnnnnnnn nnnnnnnnnn nnnnnnnnnn     1020
nnngtgcagt cagtccctcg gttaaagtct cgagtcgctc tgtcaaaata tccgtaccgt     1080
agtcgatgcg agcgagtccg atcagtccag gtttcaaagt caannnnnnn nnnnnnnnnn     1140
nnnnnnnnnn nnnnnnnnnn nnnnnnnnnn nnnnnnnnnn nnnnnnnnnn nnnnnnnnnn     1200
nnnnnnnnnn nnnnnnnnnn nnnnnnnnnn nnnnnnnnnn nnnnnnnnnn nnnnnnnnnn     1260
nnnnnnnnnn nnnnnnnnnn nnnnnnnnnn nnnnnnnnnn nnnnnnnnnn nnnnnnnnnn     1320
nnnnnnnnnn nnnnnnnnnn nnnnnnnnnn nnnnnnnnnn nnnnnnnnnn nnnnnnnnnn     1380
nnnnnnnnnn nnnnnnnnnn nnnnnnnnnn nnnnnnnnnn nnnnnnnnnn nnnnnnnnnn     1440
nnnnnnnnnn nnnnnnnnnn nnnnnnnnnn nnnnnnnnnn nnnnnnnnnn nnnnnnnnnn     1500
nnnnnnnnnn nnnnnnnnnn nnnnnnnnnn nnnnnnnnnn nnnnnnnnnn nnnnnnnnnn     1560
nnnnnnnnnn nnnnnnnnnn nnnnnnnnnn nnnnnnnnnn nnnnnnnnnn nnnnnnnnnn     1620 nnn                                                                   1623

<210> SEQ ID NO 13
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
atcgtattaa tacgactcac tatagggaat cgtcgtgcag tcagtccctc ggttaaagtc       60
tcgagtcgct ctgtcaaaat atccgtaccg tagtcgatgc gagcgagtcc gatcagtcca      120
ggtttcaaag tcaaatgact a                                                141

<210> SEQ ID NO 14
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
atcgtattaa tacgactcac tatagggaat cgtcgtgcag tcagtccctc ggttaaagtc       60
tcgagtcgct ctgtcaaaat atccgtaccg tagtcgatgc gagcgagtcc gatcagtcca      120
ggtttcaaag tcaaatgact a                                                141

<210> SEQ ID NO 15
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
atcgtattaa tacgactcac tatagggaat cgtcgtgcag tcagtccctc ggttaaagtc       60
tcgagtcgct ctgtcaaaat atccgtaccg tagtcgatgc gagcgagtcc gatcagtcca      120
```

```
ggtttcaaag tcaaatgact a                                         141

<210> SEQ ID NO 16
<211> LENGTH: 127
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
atattaatac gactcactat agggagtgca gtcagtccct cggttaaagt ctcgagtcgc   60
tctgtcaaaa tatccgtacc gtagtcgatg cgagcgagtc cgatcagtcc aggtttcaaa  120
gtcaaat                                                            127

<210> SEQ ID NO 17
<211> LENGTH: 127
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
atattaatac gactcactat agggagtgca gtcagtccct cggttaaagt ctcgagtcgc   60
tctgtcaaaa tatccgtacc gtagtcgatg cgagcgagtc cgatcagtcc aggtttcaaa  120
gtcaaat                                                            127

<210> SEQ ID NO 18
<211> LENGTH: 127
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
atattaatac gactcactat agggagtgca gtcagtccct cggttaaagt ctcgagtcgc   60
tctgtcaaaa tatccgtacc gtagtcgatg cgagcgagtc cgatcagtcc aggtttcaaa  120
gtcaaat                                                            127

<210> SEQ ID NO 19
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
tattaatacg actcactata ggggtgcagt cagtccctcg gttaaagtct cgagtcgctc   60
tgtcaaaata tccgtaccgt agtcgatgcg agcgagtccg atcagtccag gtttcaaagt  120
caa                                                                123

<210> SEQ ID NO 20
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 20
tattaatacg actcactata ggggtgcagt cagtccctcg gttaaagtct cgagtcgctc        60
tgtcaaaata tccgtaccgt agtcgatgcg agcgagtccg atcagtccag gtttcaaagt       120
caa                                                                    123

<210> SEQ ID NO 21
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
tattaatacg actcactata ggggtgcagt cagtccctcg gttaaagtct cgagtcgctc        60
tgtcaaaata tccgtaccgt agtcgatgcg agcgagtccg atcagtccag gtttcaaagt       120
caa                                                                    123

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 22
taaccgaggt cgaaacgta                                                    19

<210> SEQ ID NO 23
<211> LENGTH: 16
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 23
gcacggtgag cgtgaa                                                       16

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
tcaggccccc tcaaagc                                                      17

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 25
ggaattgcaa aggatgtaat ggaa                                              24

<210> SEQ ID NO 26

```
<211> LENGTH: 28
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 26
agaacaaatt gaaagaatct gaaatggt                                           28

<210> SEQ ID NO 27
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
atgggaaatt cagctct                                                       17

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 28
ctcgtccagc gccgcttc                                                      18

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 29
acaaaggcca cgtaggcga                                                     19

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
accagcacct aaccggctgt gggt                                               24

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 31
agcgatgagc ggtccaatc                                                     19

<210> SEQ ID NO 32
<211> LENGTH: 16
```

-continued

```
<212> TYPE: DNA
<213> ORGANISM: Artificial Sequence
<220> FEATURE:
<223> OTHER INFORMATION: Description of Artificial Sequence: Synthetic
reverse primer
<400> SEQUENCE: 32
tgccctggcg cagctt 16

<210> SEQ ID NO 33
<211> LENGTH: 14
<212> TYPE: DNA
<213> ORGANISM: Artificial Sequence
<220> FEATURE:
<223> OTHER INFORMATION: Description of Artificial Sequence: Synthetic
probe
<400> SEQUENCE: 33
ccgcaaccat cgac 14

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
Influenza Subtype H1 forward amplification primer
<400> SEQUENCE: 34
agycttcctt tccagaatgt aca 23

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
Influenza Subtype H1 reverse amplification primer
<400> SEQUENCE: 35
agtcctgtar ccatycttaa ttttg 25

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
Influenza Subtype H1 probe
<400> SEQUENCE: 36
tctccaaagt atgtcagg 18

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
Influenza Subtype H3 forward amplification primer
<400> SEQUENCE: 37
aatacgaagt gggaaaagct ca 22

<210> SEQ ID NO 38
<211> LENGTH: 23
<212> TYPE: DNA

```
<213> ORGANISM: Artificial Sequence
<220> FEATURE:
<223> OTHER INFORMATION: Description of Artificial Sequence: Synthetic
      Influenza Subtype H3 reverse amplification primer

<400> SEQUENCE: 38
gccccrtatg tgatyctgtt tac                                              23

<210> S

```
<220> FEATURE:
<223> OTHER INFORMATION: Description of Artificial Sequence: Synthetic
      Influenza Type A reverse amplification primer

<400> SEQUENCE: 44
agtagaaaca aggtagtttt ttac                                              24

<210> SEQ ID NO 45
<211> LENGTH: 45
<212> TYPE: DNA
<213> ORGANISM: Artificial Sequence
<220> FEATURE:
<223> OTHER INFORMATION: Description of Artificial Sequence: Synthetic
      Influenza Type B forward amplification primer

<400> SEQUENCE: 45
gctaatacga ctcactatag ggagatcgct gtttggagac acaat                       45

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      Influenza Type B reverse amplification primer

<400> SEQUENCE: 46
ctccaaaact gtttcaccca                                                   20

<210> SEQ ID NO 47
<211> LENGTH: 43
<212> TYPE: DNA
<213> ORGANISM: Artificial Sequence
<220> FEATURE:
<223> OTHER INFORMATION: Description of Artificial Sequence: Synthetic
      Influenza Type H1 forward amplification primer

<400> SEQUENCE: 47
gctaatacga ctcactatag ggagaaagca ggggaaaata aaa                         43

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic
      Influenza Type H1 reverse amplification primer

<400> SEQUENCE: 48
gtaatcccgt taatcgca                                                     18

<210> SEQ ID NO 49
<211> LENGTH: 43
<212> TYPE: DNA
<213> ORGANISM: Artificial Sequence
<220> FEATURE:
<223> OTHER INFORMATION: Description of Artificial Sequence: Synthetic
      Influenza Subtype H3 forward amplification primer

<400> SEQUENCE: 49
gctaatacga ctcactatag ggagaactat cattgctttg agc                         43

<210> SEQ ID NO 50
<211> LENGTH: 18
<212> TYPE: DNA
<213> ORGANISM: Artificial Sequence
<220> FEATURE:
```

<223> OTHER INFORMATION: Description of Artificial Sequence: Synthetic
      Influenza Subtype H3 reverse amplification primer

<400> SEQUENCE: 50
atggctgctt gagtgctt                                                     18

<210> SEQ ID NO 51
<211> LENGTH: 47
<212> TYPE: DNA
<213> ORGANISM: Artificial Sequence
<220> FEATURE:
<223> OTHER INFORMATION: Description of Artificial Sequence: Synthetic
      Influenza Subtype H5 forward amplification primer

<400> SEQUENCE: 51
gctaatacga ctcactatag ggagatcatc tgtcaaatgg agaaaat                     47

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      Influenza Subtype H5 reverse amplification primer

<400> SEQUENCE: 52
aaggatagac cagctaccat ga                                                22

<210> SEQ ID NO 53
<211> LENGTH: 146
<212> TYPE: DNA
<213> ORGANISM: Influenza A virus

<400> SEQUENCE: 53
gactacccgc agtattcaga agaagcaaga ttaaaaagag aggaaataag tggagtaaaa       60
ttggaatcaa taggaactta ccaaatactg tcaatttatt caacagttgc gagttctcta      120
gcactggcaa tcatggtggc tggtct                                           146

<210> SEQ ID NO 54
<211> LENGTH: 146
<212> TYPE: DNA
<213> ORGANISM: Influenza A virus

<400> SEQUENCE: 54
gactacccgc agtattcaga agaagcaaga ttaaaaagag aggaaataag tggagtaaaa       60
ttggaatcaa taggaactta ccaaatactg tcaatttatt caacagtggc gagctcccta      120
gcactggcaa tcatggtggc tggtct                                           146

<210> SEQ ID NO 55
<211> LENGTH: 146
<212> TYPE: DNA
<213> ORGANISM: Influenza A virus

<400> SEQUENCE: 55
gactacccgc agtattcaga agaagcaaga ttaaaaagag aggaaataag tggagtaaaa       60
ttggaatcaa taggaattta ccaaatactg tcaatttatt ctacagtggc gagttcccta      120
gcactggcaa tcatggtagc tggtct                                           146

<210> SEQ ID NO 56
<211> LENGTH: 146
<212> TYPE: DNA

<213> ORGANISM: Influenza A virus

<400> SEQUENCE: 56
gactacccgc agtattcaga agaagcaaga ttaaaaagag aggaaataag tggagtaaaa 60
ttggaatcaa taggaactta ccaaatactg tcaatttatt caacagtggc gagttcccta 120
gcactggcaa tcatggtggc tggtct 146

<210> SEQ ID NO 57
<211> LENGTH: 146
<212> TYPE: DNA
<213> ORGANISM: Influenza A virus

<400> SEQUENCE: 57
gactacccgc agtattcaga agaagcaaga ctaaacagag aggaaataag tggagtaaaa 60
ttggaatcaa tgggaattta ccaaatactg tcaatttatt caacagtggc gagttcccta 120
gcactggcaa tcatggtagc tggtct 146

<210> SEQ ID NO 58
<211> LENGTH: 146
<212> TYPE: DNA
<213> ORGANISM: Influenza A virus

<400> SEQUENCE: 58
gactacccgc agtattcaga agaagcaaga ctaaacagag aggaaataag tggagtaaaa 60
ttggaatcaa tgggaactta ccaaatactg tcaatttatt caacagtggc gagttcccta 120
gcactggcaa tcatggtagc tggtct 146

<210> SEQ ID NO 59
<211> LENGTH: 146
<212> TYPE: DNA
<213> ORGANISM: Influenza A virus

<400> SEQUENCE: 59
gactacccgc agtattcaga agaagcaaga ttaaaaagag aggaaataag tggagtaaaa 60
ttggaatcaa taggaactta ccaaatcctg tcaatttatt caacagtggc gagctcccta 120
gcactggcaa tcatggtggc tggtct 146

<210> SEQ ID NO 60
<211> LENGTH: 146
<212> TYPE: DNA
<213> ORGANISM: Influenza A virus

<400> SEQUENCE: 60
gactacccgc agtattcaga agaagcaaaa ctaaaaagag cggaaataag tggagtaaaa 60
ttggaatcaa taggaattta ccaaatactg tcaatttatt ccacagtagc gagttcccta 120
gcactggcaa tcatggtagc tggtct 146

<210> SEQ ID NO 61
<211> LENGTH: 146
<212> TYPE: DNA
<213> ORGANISM: Influenza A virus

<400> SEQUENCE: 61
gactacccgc agtattcaga agaagcaaga ctaaacagag aggaaataag tggagtaaaa 60
ttggagtcaa tgggaattta ccaaatactg tcaatttatt caacagtggc gagttcccta 120
gcactggcaa tcatggtagc tggtct 146

<210> SEQ ID NO 62
<211> LENGTH: 146
<212> TYPE: DNA
<213> ORGANISM: Influenza A virus

<400> SEQUENCE: 62
gactacccgc agtattcaga agaagcaaga ttaaaaagag aggaaataag tggagtaaaa      60
ttggaatcaa taggaattta ccaaatactg tcaatttatt caacagtggc gagctcccta     120
gcactggcaa tcatggtggc tggtct                                          146

<210> SEQ ID NO 63
<211> LENGTH: 146
<212> TYPE: DNA
<213> ORGANISM: Influenza A virus

<400> SEQUENCE: 63
gactacccgc agtattcaga agaagcaaga ctaaaaagag aggaaataag tggagtaaaa 60
ttggaatcaa taggaattta ccaaatactg tcaatttatt ctacagtggc gagttcccta 120
gcactggcaa tcatggtagc tggtct 146

<210> SEQ ID NO 64
<211> LENGTH: 146
<212> TYPE: DNA
<213> ORGANISM: Influenza A virus

<400> SEQUENCE: 64
gactacccgc agtattcaga agaagcgaga ctaaaaagag aggaaataag tggagtaaaa 60
ttggaatcaa taggaattta ccaaatactg tcaatttatt ctacagtggc gagttcccta 120
gcactggcaa tcatggtagc tggtct 146

<210> SEQ ID NO 65
<211> LENGTH: 145
<212> TYPE: DNA
<213> ORGANISM: Influenza A virus

<400> SEQUENCE: 65
gactacccgc agtattcaga agaagcaaga ctaaaaagag aggaaataag tggagtaaaa 60
ttggagtcaa taggaactta ccaaatactg tcaatttatt ctacagtggc gagttcccta 120
gcactggcaa tcatggtagc tggtc 145

<210> SEQ ID NO 66
<211> LENGTH: 145
<212> TYPE: DNA
<213> ORGANISM: Influenza A virus

<400> SEQUENCE: 66
gactacccgc agtattcaga agaagcaaga ctaaaaagag aggaaataag tggagtaaaa 60
ttggaatcaa taggaattta ccaaatattg tcaatttatt ctacagtggc gagctcccta 120
gcactggcaa tcatggtagc tggtc 145

<210> SEQ ID NO 67
<211> LENGTH: 145
<212> TYPE: DNA
<213> ORGANISM: Influenza A virus

<400> SEQUENCE: 67
aactatccgc agtattcaga agaagcaaga ttaaaaagag aggaaataag tggggtaaaa    60
ttggaatcaa taggaactta ccaaatactg tcaatttatt caacagtggc gagttcccta   120
gcactggcaa tcatgatggc tggtc                                         145

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 68
tggcaatcat grtrgctggt c                                              21

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
      Influenza A H1N1 forward primer

<400> SEQUENCE: 69
agcctyccat ttcagaatat aca                                            23

<210> SEQ ID NO 70
<211> LENGTH: 25
<212> TYPE: DNA
<213> ORGANISM: Artificial Sequence
<220> FEATURE:
<223> OTHER INFORMATION: Description of Artificial Sequence: Synthetic
      Influenza A H1N1 reverse primer

<400> SEQUENCE: 70
aatcctgtrg ccagtctcaa ttttg                                          25

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
      Influenza A H1N1 probe

<400> SEQUENCE: 71
tccaaaatat gtaaaaag                                                  18

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tcctctaagg gctctcgtt                                                 19

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 73
gtcaggtaca cgatctcgt                                                      19

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
atcgaaacgc cgtaccgcaa                                                     20

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tgacgtcgag cacgtaactc cct                                                 23

<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
acaccaactc ctgggaagga at                                                  22

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tgatcgcaca tccagcacat tt                                                  22

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gacggatttg tcgctcacta c                                                   21

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 79
gccggagacg atatccagat                                                        20

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
aaggatgttc ggttcctgga t                                                      21

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
taacactcgt acccggct                                                          18

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ttctaaatac ctttggctcc ct                                                     22

<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
tggccaactt tgttgtcatg ca                                                     22

<210> SEQ ID NO 84
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
acgcgtgatc agcaaaagca gg                                                     22

<210> SEQ ID NO 85
<211> LENGTH: 1161
<212> TYPE: DNA
<213> ORGANISM: Mycobacterium tuberculosis

<400> SEQUENCE: 85
aggcgggaat gaacaccgtc acagccgagt ccatcgcgac ctcgagttcg agatcgcgca            60

-continued

```
gcaccaccgt gccggagacg atatccagat cgcgatggaa cgtgatatcc cgcggcccga      120
tgaaggtgtc gtagaagcgg ccgatggcct catgccccac ctgcggctgc gaacccaccg      180
ggtcttcgac ccgcgcgtca ccggtgaaca acccgaccca gccggcgcgg tcgtgcgcgg      240
cggccgcttg cggcgagcgc tccaccgccg ccaacagttc atcccggttc ggcggtgcca      300
tcaggagctg caaaccaact cgacgctggc ggtgcgcatc tcctccagcg cggcgacggt      360
ggtatcggcc gacacacccg ctgtcaggtc caccagcacc ctggtggcca agccattgcg      420
taccgcgtcc tcggccgtct ggcgcacaca atgatcggtg caataccga ccacatcgac       480 ctcatcgacg ccgcgttgcc gcagccaatt cagcagtggc gtgccgttct cgtcgactcc      540
ttcgaagccg ctgtacgctc cggtgtaggc acccttgtag aacaccgcct cgattgccga      600
cgtgtccaga ctgggatgga agtccgcgcc gggagtaccg ctgacgcaat gcggtggcca      660
cgacgaggaa tagtccggtg tgccggagaa gtggtcaccc gggtcgatgt ggaagtcctt      720
ggttgccacg acgtgatggt agtccgccgc ttcggccagg tagtcgctga tggcgcgggc      780
cagcgcggcg ccaccggtta ccgccagcga gccaccctcg cagaagtcgt tctgcacgtc      840
gacgatgatc aacgcccgca tacgtccacc atacgttcgg gcgactgccc gggcagtttg      900
cctaccgacg cggcagccac agatataggg tccatgacgc cgcgacgatc gcgaacatga      960
ccagctgagc ggcggccacc caaccggcgg gatagatcac gccggtgatg tagtgagcga     1020
caaatccgtc cggtgacaga ggtgtcatcg cggccttggt gcgagcccag cgctccaccc     1080
aggtcagcgg gcagtcgacc cgcttagcgg cgatgccgat ccccatatc accgccggaa      1140 catgcagcca catcgtgcgt c                                                1161

<210> SEQ ID NO 86
<211> LENGTH: 1161
<212> TYPE: DNA
<213> ORGANISM: Mycobacterium tuberculosis

<400> SEQUENCE: 86
gacgcacgat gtggctgcat gttccggcgg tgatatgggg gatcggcatc gccgctaagc       60
gggtcgactg cccgctgacc tgggtggagc gctgggctcg caccaaggcc gcgatgacac      120
ctctgtcacc ggacggattt gtcgctcact acatcaccgg cgtgatctat cccgccggtt      180
gggtggccgc cgctcagctg gtcatgttcc gatcgtcgc ggcgtcatgg accctatatc       240
tgtggctgcc gcgtcggtag gcaaactgcc cgggcagtcg cccgaacgta tggtggacgt      300
atgcgggcgt tgatcatcgt cgacgtgcag aacgacttct gcgagggtgg ctcgctggcg      360
gtaaccggtg gcgccgcgct ggcccgcgcc atcagcgact acctggccga agcggcggac      420
taccatcacg tcgtggcaac caaggacttc cacatcgacc cgggtgacca cttctccggc      480
acaccggact attcctcgtc gtggccaccg cattgcgtca gcggtactcc cggcgcggac      540
ttccatccca gtctggacac gtcggcaatc gaggcggtgt tctacaaggg tgcctacacc      600
ggagcgtaca gcggcttcga aggagtcgac gagaacggca cgccactgct gaattggctg      660
cggcaacgcg cgtcgatga ggtcgatgtg gtcggtattg ccaccgatca ttgtgtgcgc       720
cagacggcca aggacgcggt acgcaatggc ttggccacca gggtgctggt ggacctgaca      780
gcgggtgtgt cggccgatac caccgtcgcc gcgctggagg agatgcgcac cgccagcgtc      840
gagttggttt gcagctcctg atggcaccgc cgaaccggga tgaactgttg gcggcggtgg      900
agcgctcgcc gcaagcggcc gccgcgcacg accgcgccgg ctgggtcggg ttgttccacg      960
gtgacgcgcg ggtcgaagac ccggtggggtt cgcagccgca ggtggggcat gaggccatcg     1020
```

```
gccgcttcta cgacaccttc atcgggccgc gggatatcac gttccatcgc gatctggata    1080
tcgtctccgg cacggtggtg ctgcgcgatc tcgaactcga ggtcgcgatg gactcggctg    1140
tgacggtgtt cattcccgcc t                                              1161
```

<210> SEQ ID NO 87
<211> LENGTH: 186
<212> TYPE: PRT
<213> ORGANISM: Mycobacterium tuberculosis

<400> SEQUENCE: 87

```
Met Arg Ala Leu Ile Ile Val Asp Val Gln Asn Asp Phe Cys Glu Gly
1               5                   10                  15

Gly Ser Leu Ala Val Thr Gly Gly Ala Ala Leu Ala Arg Ala Ile Ser
            20                  25                  30

Asp Tyr Leu Ala Glu Ala Ala Asp Tyr His His Val Ala Thr Lys
        35                  40                  45

Asp Phe His Ile Asp Pro Gly Asp His Phe Ser Gly Thr Pro Asp Tyr
    50                  55                  60

Ser Ser Ser Trp Pro Pro His Cys Val Ser Gly Thr Pro Gly Ala Asp
65                  70                  75                  80

Phe His Pro Ser Leu Asp Thr Ser Ala Ile Glu Ala Val Phe Tyr Lys
                85                  90                  95

Gly Ala Tyr Thr Gly Ala Tyr Ser Gly Phe Glu Gly Val Asp Glu Asn
            100                 105                 110

Gly Thr Pro Leu Leu Asn Trp Leu Arg Gln Arg Gly Val Asp Glu Val
        115                 120                 125

Asp Val Val Gly Ile Ala Thr Asp His Cys Val Arg Gln Thr Ala Glu
    130                 135                 140

Asp Ala Val Arg Asn Gly Leu Ala Thr Arg Val Leu Val Asp Leu Thr
145                 150                 155                 160

Ala Gly Val Ser Ala Asp Thr Thr Val Ala Ala Leu Glu Glu Met Arg
                165                 170                 175

Thr Ala Ser Val Glu Leu Val Cys Ser Ser
            180                 185
```

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88

```
tcatggaccc tatatctgtg                                                  20
```

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89

```
atgaactgtt ggcggcggtg                                                  20
```

<210> SEQ ID NO 90

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
acggatttgt cgctcactac                                                 20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
atctggatat cgtctccggc                                                 20

<210> SEQ ID NO 92
<211> LENGTH: 1737
<212> TYPE: DNA
<213> ORGANISM: Mycobacterium tuberculosis

<400> SEQUENCE: 92
ggccatgctc ttgatgcccc gttgtcgggg gcgtggccgt tgttttgtc aggatatttc      60 taaataccct tggctccctt ttccaaaggg agtgtttggg ttttgtttgg agagtttgat    120
cctggctcag gacgaacgct ggcggcgtgc ttaacacatg caagtcgaac ggaaaggtct    180
cttcggagat actcgagtgg cgaacgggtg agtaacacgt gggtgatctg ccctgcactt    240
cgggataagc ctgggaaact gggtctaata ccggatagga ccacgggatg catgtcttgt    300
ggtggaaagc gctttagcgg tgtgggatga gcccgcggcc tatcagcttg ttggtggggt    360
gacggcctac caaggcgacg acgggtagcc ggcctgagag ggtgtccggc cacactggga    420
ctgagatacg gcccagactc ctacgggagg cagcagtggg gaatattgca caatgggcgc    480
aagcctgatg cagcgacgcc gcgtggggga tgacggcctt cgggttgtaa acctctttca    540
ccatcgacga aggtccgggt tctctcggat tgacggtagg tggagaagaa gcaccggcca    600
actacgtgcc agcagccgcg gtaatacgta gggtgcgagc gttgtccgga attactgggc    660
gtaaagagct cgtaggtggt ttgtcgcgtt gttcgtgaaa tctcacggct taactgtgag    720
cgtgcgggcg atacgggcag actagagtac tgcaggggag actggaattc ctggtgtagc    780
ggtggaatgc gcagatatca ggaggaacac cggtggcgaa ggcgggtctc tgggcagtaa    840
ctgacgctga ggagcgaaag cgtggggagc gaacaggatt agatacctg gtagtccacg    900 ccgtaaacgg tgggtactag gtgtgggttt ccttccttgg gatccgtgcc gtagctaacg    960
cattaagtac cccgcctggg gagtacggcc gcaaggctaa aactcaaagg aattgacggg   1020
ggcccgcaca agcggcggag catgtggatt aattcgatgc aacgcgaaga accttacctg   1080
ggtttgacat gcacaggacg cgtctagaga taggcgttcc cttgtggcct gtgtgcaggt   1140
ggtgcatggc tgtcgtcagc tcgtgtcgtg agatgttggg ttaagtcccg caacgagcgc   1200
aacccttgtc tcatgttgcc agcacgtaat ggtgggact cgtgagagac tgccggggtc   1260
aactcggagg aaggtgggga tgacgtcaag tcatcatgcc ccttatgtcc agggcttcac   1320
acatgctaca atggccggta caaagggctg cgatgccgcg aggttaagcg aatccttaaa   1380
agccggtctc agttcggatc ggggtctgca actcgacccc gtgaagtcgg agtcgctagt   1440
```

```
aatcgcagat cagcaacgct gcggtgaata cgttcccggg ccttgtacac accgcccgtc    1500
acgtcatgaa agtcggtaac acccgaagcc agtggcctaa ccctcgggag ggagctgtcg    1560
aaggtgggat cggcgattgg gacgaagtcg taacaaggta gccgtaccgg aaggtgcggc    1620
tggatcacct cctttctaag gagcaccacg aaaacgcccc aactggtggg gcgtaggccg    1680 tgagggggttc ttgtctgtag tgggcgagag ccgggtgcat gacaacaaag ttggcca     1737
```

<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 93

```
tggccgtttg ttttgtcagg at                                             22
```

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 94

```
tacagacaag aacccctcac gg                                             22
```

<210> SEQ ID NO 95
<211> LENGTH: 1773
<212> TYPE: DNA
<213> ORGANISM: Mycobacterium tuberculosis

<400> SEQUENCE: 95

```
gatccggaca gatcgttcgc cggccgaaac cgacaaaatt atcgcggcga acgggcccgt    60
gggcaccgct cctctaaggg ctctcgttgg tcgcatgaag tgctggaagg atgcatcttg   120
gcagattccc gccagagcaa aacagccgct agtcctagtc cgagtcgccc gcaaagttcc   180
tcgaataact ccgtacccgg agcgccaaac cgggtctcct tcgctaagct gcgcgaacca   240
cttgaggttc cgggactcct tgacgtccag accgattcgt tcgagtggct gatcggttcg   300
ccgcgctggc gcgaatccgc cgccgagcgg ggtgatgtca acccagtggg tggcctggaa   360
gaggtgctct acgagctgtc tccgatcgag gacttctccg gtcgatgtc gttgtcgttc    420 tctgacctc gtttcgacga tgtcaaggca cccgtcgacg agtgcaaaga caaggacatg   480
acgtacgcgg ctccactgtt cgtcaccgcc gagttcatca acaacaacac cggtgagatc   540
aagagtcaga cggtgttcat gggtgacttc ccgatgatga ccgagaaggg cacgttcatc   600
atcaacggga ccgagcgtgt ggtggtcagc cagctggtgc ggtcgcccgg ggtgtacttc   660
gacgagacca ttgacaagtc caccgacaag acgctgcaca gcgtcaaggt gatcccgagc   720
cgcggcgcgt ggctcgagtt tgacgtcgac aagcgcgaca ccgtcggcgt gcgcatcgac   780
cgcaaacgcc ggcaaccggt caccgtgctg ctcaaggcgc tgggctggac cagcgagcag   840
attgtcgagc ggttcgggtt ctccgagatc atgcgatcga cgctggagaa ggacaacacc   900
gtcggcaccg acgaggcgct gttggacatc taccgcaagc tgcgtccggg cgagcccccg   960
accaaagagt cagcgcagac gctgttggaa aacttgttct tcaaggagaa gcgctacgac   1020
```

```
ctggcccgcg tcggtcgcta taaggtcaac aagaagctcg ggctgcatgt cggcgagccc    1080
atcacgtcgt cgacgctgac cgaagaagac gtcgtggcca ccatcgaata tctggtccgc    1140
ttgcacgagg gtcagaccac gatgaccgtt ccgggcggcg tcgaggtgcc ggtggaaacc    1200
gacgacatcg accacttcgg caaccgccgc ctgcgtacgg tcggcgagct gatccaaaac    1260
cagatccggg tcggcatgtc gcggatggag cgggtggtcc gggagcggat gaccacccag    1320
gacgtggagg cgatcacacc gcagacgttg atcaacatcc ggccggtggt cgccgcgatc    1380
aaggagttct tcggcaccag ccagctgagc caattcatgg accagaacaa cccgctgtcg    1440
gggttgaccc acaagcgccg actgtcggcg ctggggcccg gcggtctgtc acgtgagcgt    1500
gccgggctgg aggtccgcga cgtgcacccg tcgcactacg gccggatgtg cccgatcgaa    1560 accccctgagg ggcccaacat cggtctgatc ggctcgctgt cggtgtacgc gcgggtcaac    1620
ccgttcgggt tcatcgaaac gccgtaccgc aaggtggtca acggcgtggt tagcgacgag    1680
atcgtgtacc tgaccgccga cgaggaggac cgccacgtgg tggcacaggc caattcgccg    1740
atcgatgcgg acggtcgctt cgtcgagccg cgc                                1773

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
accgacaaaa ttatcgcggc ga                                              22

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
atcgatcggc gaattggcct gt                                              22

<210> SEQ ID NO 98
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
tcgccgcgat caaggagt                                                   18

<210> SEQ ID NO 99
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
tggaggtccg cgacgtgca                                                  19
```

```
<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
aatatctggt ccgcttgcac ga                                            22

<210> SEQ ID NO 101
<211> LENGTH: 2717
<212> TYPE: DNA
<213> ORGANISM: Mycobacterium tuberculosis

<400> SEQUENCE: 101
gacgtcgacg cgcggcgcag ctttatcacc cgcaacgcca aggatgttcg gttcctggat    60
gtctaacgca accctgcgtt cgattgcaaa cgaggaatag atgacagaca cgacgttgcc   120
gcctgacgac tcgctcgacc ggatcgaacc ggttgacatc gagcaggaga tgcagcgcag   180
ctacatcgac tatgcgatga gcgtgatcgt cggccgcgcg ctgccggagg tgcgcgacgg   240
gctcaagccc gtgcatcgcc gggtgctcta tgcaatgttc gattccggct ccgcccgga    300 ccgcagccac gccaagtcgg cccggtcggt tgccgagacc atgggcaact accacccgca   360
cggcgacgcg tcgatctacg acagcctggt gcgcatggcc cagccctggt cgctgcgcta   420
cccgctggtg gacggccagg gcaacttcgg ctcgccaggc aatgacccac cggcggcgat   480
gaggtacacc gaagcccggc tgaccccgtt ggcgatggaa tgctgagggg aaatcgacga   540
ggagacagtc gatttcatcc ctaactacga cggccgggtg caagagccga cggtgctacc   600
cagccggttc cccaacctgc tggccaacgg gtcaggcggc atcgcggtcg gcatggcaac   660
caatatcccg ccgcacaacc tgcgtgagct ggccgacgcg gtgttctggg cgctggagaa   720
tcacgacgcc gacgaagagg agaccctggc cgcggtcatg gggcgggtta aaggcccgga   780
cttcccgacc gccggactga tcgtcggatc ccagggcacc gctgatgcct acaaaactgg   840
ccgcggctcc attcgaatgc gcggagttgt tgaggtagaa gaggattccc gcggtcgtac   900
ctcgctggtg atcaccgagt tgccgtatca ggtcaaccac gacaacttca tcacttcgat   960
cgccgaacag gtccgagacg gcaagctggc cggcatttcc aacattgagg accagtctag  1020
cgatcgggtc ggtttacgca tcgtcatcga gatcaagcgc gatgcggtgg ccaaggtggt  1080
gatcaataac ctttacaagc acacccagct gcagaccagc tttggcgcca acatgctagc  1140
gatcgtcgac ggggtgccgc gcacgctgcg gctggaccag ctgatccgct attacgttga  1200
ccaccaactc gacgtcattg tgcggcgcac cacctaccgg ctgcgcaagg caaacgagcg  1260
agcccacatt ctgcgcggcc tggttaaagc gctcgacgcg ctggacgagg tcattgcact  1320
gatccgggcg tcggagaccg tcgatatcgc ccggccgga ctgatcgagc tgctcgacat  1380
cgacgagatc caggcccagg caatcctgga catgcagttg cggcgcctgg ccgcactgga  1440
acgccagcgc atcatcgacg acctggccaa atcgaggcc gagatcgccg atctggaaga  1500
catcctggca aaaccgagc ggcagcgtgg gatcgtgcgc gacgaactcg ccgaaatcgt  1560
ggacaggcac ggcgacgacc ggcgtacccg gatcatcgcg gccgacggag acgtcagcga  1620
cgaggatttg atcgcccgcg aggacgtcgt tgtcactatc accgaaacgg gatacgccaa  1680
gcgcaccaag accgatctgt atcgcagcca gaaacgcggc ggcaagggcg tgcagggtgc  1740
ggggttgaag caggacgaca tcgtcgcgca cttcttcgtg tgctccaccc acgatttgat  1800
```

```
cctgttcttc accacccagg gacgggttta tcgggccaag gcctacgact tgcccgaggc    1860
ctcccggacg gcgcgcgggc agcacgtggc caacctgtta gccttccagc ccgaggaacg    1920
catcgcccag gtcatccaga ttcgcggcta caccgacgcc ccgtacctgg tgctggccac    1980
tcgcaacggg ctggtgaaaa agtccaagct gaccgacttc gactccaatc gctcgggcgg    2040
aatcgtggcg gtcaacctgc gcgacaacga cgagctggtc ggtgcggtgc tgtgttcggc    2100
cggcgacgac ctgctgctgg tctcggccaa cgggcagtcc atcaggttct cggcgaccga    2160
cgaggcgctg cggccaatgg gtcgtgccac ctcgggtgtg cagggcatgc ggttcaatat    2220
cgacgaccgc ctgctgtcgc tgaacgtcgt gcgtgaaggc acctatctgc tggtggcgac    2280 gtcaggggc tatgcgaaac gtaccgcgat cgaggaatac ccggtacagg ccgcggcgg     2340 taaaggtgtg ctgacggtca tgtacgaccg ccggcgcggc aggttggttg gggcgttgat    2400
tgtcgacgac gacagcgagc tgtatgccgt cacttccggc ggtggcgtga tccgcaccgc    2460
ggcacgccag gttcgcaagg cgggacggca gaccaagggt gttcggttga tgaatctggg    2520
cgagggcgac acactgttgg ccatcgcgcg caacgccgaa gaaagtggcg acgataatgc    2580
cgtggacgcc aacggcgcag accagacggg caattaatca ggctcgcccg acgacgatgc    2640
ggatcgcgta gcgatctgag gaggaatcgg gcagctaggc tcggcagccg ggtacgagtg    2700
ttaggagtcg gggtgac                                                   2717

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
ctaacgcaac cctgcgttcg at                                               22

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
attcctcctc agatcgctac g                                                21

<210> SEQ ID NO 104
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
cgtcgtagtt agggatgaaa tc                                               22

<210> SEQ ID NO 105
<211> LENGTH: 2640
<212> TYPE: DNA
<213> ORGANISM: Mycobacterium tuberculosis

<400> SEQUENCE: 105
```

```
gtcttgcggg gttatcgccg atgtcgactg tgctgttggc gaggcaccct gtctgacggc    60
ctcggaccat aacggcttcc tgttggacga ggcggaggtc atctactggg gtctatgtcc   120
tgattgttcg atatccgaca cttcgcgatc acatccgtga tcacagcccg ataacaccaa   180
ctcctggaag gaatgctgtg cccgagcaac acccacccat tacagaaacc accaccggag   240
ccgctagcaa cggctgtccc gtcgtgggtc atatgaaata ccccgtcgag ggcggcggaa   300
accaggactg gtggcccaac cggctcaatc tgaaggtact gcaccaaaac ccggccgtcg   360
ctgacccgat gggtgcggcg ttcgactatg ccgcggaggt cgcgaccatc gacgttgacg   420
ccctgacgcg ggacatcgag gaagtgatga ccacctcgca gccgtggtgg cccgccgact   480
acggccacta cgggccgctg tttatccgga tggcgtggca cgctgccggc acctaccgca   540
tccacgacgg ccgcggcggc gccgggggcg gcatgcagcg gttcgcgccg cttaacagct   600
ggcccgacaa cgccagcttg gacaaggcgc gccggctgct gtggccggtc aagaagaagt   660
acggcaagaa gctctcatgg gcggacctga ttgttttcgc cggcaactgc gcgctggaat   720
cgatgggctt caagacgttc gggttcggct tcggccgggt cgaccagtgg gagcccgatg   780
aggtctattg gggcaaggaa gccacctggc tcggcgatga cgttacagc ggtaagcggg    840
atctggagaa cccgctggcc gcggtgcaga tggggctgat ctacgtgaac ccggagggc    900
cgaacggcaa cccggacccc atggccgcgg cggtcgacat cgcgagacg tttcggcgca    960
tggccatgaa cgacgtcgaa acagcggcgc tgatcgtcgg cggtcacact ttcggtaaga  1020
cccatggcgc cggcccggcc gatctggtcg gccccgaacc cgaggctgct ccgctggagc  1080
agatgggctt gggctggaag agctcgtatg gcaccggaac cggtaaggac gcgatcacca  1140
gcggcatcga ggtcgtatgg acgaacaccc cgacgaaatg ggacaacagt ttcctcgaga  1200
tcctgtacgg ctacgagtgg gagctgacga agagccctgc tggcgcttgg caatacaccg  1260
ccaaggacgg cgccggtgcc ggcaccatcc cggacccgtt cggcgggcca gggcgctccc  1320
cgacgatgct ggccactgac ctctcgctgc gggtggatcc gatctatgag cggatcacgc  1380
gtcgctggct ggaacacccc gaggaattgg ccgacgagtt cgccaaggcc tggtacaagc  1440
tgatccaccg agacatgggt cccgttgcga gataccttgg gccgctggtc cccaagcaga  1500
ccctgctgtg gcaggatccg gtccctgcgg tcagccacga cctcgtcggc gaagccgaga  1560
ttgccagcct taagagccag atccgggcat cgggattgac tgtctcacag ctagtttcga  1620
ccgcatgggc ggcggcgtcg tcgttccgtg gtagcgacaa gcgcggcggc gccaacggtg  1680
gtcgcatccg cctgcagcca caagtcgggt gggaggtcaa cgaccccgac ggggatctgc  1740
gcaaggtcat tcgcaccctg gaagagatcc aggagtcatt caactccgcg gcgccgggga  1800
acatcaaagt gtccttcgcc gacctcgtcg tgctcggtgg ctgtgccgcc atagagaaag  1860
cagcaaaggc ggctggccac aacatcacgg tgcccttcac cccgggccgc acggatgcgt  1920
cgcaggaaca aaccgacgtg gaatcctttg ccgtgctgga gcccaaggca gatgccttcc  1980
gaaactacct cggaaagggc aacccgttgc cggccgagta catgctgctc gacaaggcga  2040
acctgcttac gctcagtgcc cctgagatga cggtgctggt aggtggcctg cgcgtcctcg  2100
gcgcaaacta caagcgctta ccgctgggcg tgttcaccga ggcctccgag tcactgacca  2160
acgacttctt cgtgaacctg ctcgacatgg gtatcacctg ggagccctcg ccagcagatg  2220
acgggaccta ccagggcaag gatggcagtg gcaaggtgaa gtggaccggc agccgcgtgg  2280
acctggtctt cggggtccaac tcggagttgc gggcgcttgt cgaggtctat ggcgccgatg  2340
```

```
acgcgcagcc gaagttcgtg caggacttcg tcgctgcctg ggacaaggtg atgaacctcg    2400
acaggttcga cgtgcgctga ttcgggttga tcggccctgc ccgccgatca accacaaccc    2460
gccgcagcac cccgcgagct gaccggctcg cggggtgctg gtgtttgccc ggcgcgattt    2520
gtcagacccc gcgtgcatgg tggtcgcagg cacgacgaga cggggatgac gagacgggga    2580
tgaggagaaa gggcgccgaa atgtgctgga tgtgcgatca cccggaagcc accgccgagg    2640
```

<210> SEQ ID NO 106
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
tcgcgatcac atccgtgatc ac                                              22

<210> SEQ ID NO 107
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
atgcacgcgg ggtctgacaa at                                              22

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
acaccaactc ctggaaggaa t                                               21

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
ttacagcggt aagcgggatc t                                               21

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
ttggcgaact cgtcggccaa tt                                              22

<210> SEQ ID NO 111
<211> LENGTH: 22
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 111
attatattca gtatggaaag aa                                              22

<210> SEQ ID NO 112
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
atatatccac agcttgttc                                                  19

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
gatccactag catctttatt                                                 20

<210> SEQ ID NO 114
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gtacgtctct catttgtt                                                   18

<210> SEQ ID NO 115
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
aaggcatttt cagaaagat                                                  19

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
gtcgttttta aactattcag c                                               21

<210> SEQ ID NO 117
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 117
accatttgaa tggatgtc                                                     18

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
ttgattcttt gtgatgtatg t                                                 21

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
aatgatgact aattcacaag                                                   20

<210> SEQ ID NO 120
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
ataattctca tccatcagc                                                    19

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
aaatacacca agacaacata                                                   20

<210> SEQ ID NO 122
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
catgaaggac aagctaaat                                                    19

<210> SEQ ID NO 123
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 123
attttgaatg gatgtcaatc                                                 20

<210> SEQ ID NO 124
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
gtgattgtga aagaaagct                                                  19

<210> SEQ ID NO 125
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
ctgattcgaa atggaaga                                                   18

<210> SEQ ID NO 126
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
cgtgtggttt gactatat                                                   18

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gatcaagtgc ataaaaacat                                                 20

<210> SEQ ID NO 128
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
atagagtcct acagacttt                                                  19

<210> SEQ ID NO 129
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 129
tgacgaacct gaattaag                                                 18

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
gtacggataa caaatagtag                                               20

<210> SEQ ID NO 131
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
taattctatt aaccatgaag ac                                            22

<210> SEQ ID NO 132
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
gcatctgatc tcattattg                                                19

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133 catactttg attaacagca                                                20

<210> SEQ ID NO 134
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
ttaatgcact caaatgca                                                 18

<210> SEQ ID NO 135
<211> LENGTH: 19
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 135
aataatcact cactgagtg                                                  19

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
aatatgagat cttcgatctc                                                 20

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
acaagaagtg cttatgag                                                   18

<210> SEQ ID NO 138
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
ttccttaatt gtcgtactc                                                  19

<210> SEQ ID NO 139
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
ctgagtgaca tcaaaatca                                                  19

<210> SEQ ID NO 140
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
gcagctgttt gaaattttc                                                  19

<210> SEQ ID NO 141
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
aagatgaatc caaaccaa                                                    18

<210> SEQ ID NO 142
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
gtatcagctt ttcctgaa                                                    18

<210> SEQ ID NO 143
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
gatagtgttg tttcatgg                                                    18

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
ctaaaattgc gaaagcttat a                                                21

<210> SEQ ID NO 145
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
atattgaaag atgagcctt                                                   19

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146 tagttttta ctccaactct a                                                 21

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147

-continued acaaagacat aatggattct                                           20

<210> SEQ ID NO 148
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148 ggtgttttt atcatcaaat aag                                        23

<210> SEQ ID NO 149
<211> LENGTH: 960
<212> TYPE: DNA
<213> ORGANISM: Mycobacterium tuberculosis

<400> SEQUENCE: 149
gacggatttg tcgctcacta catcaccggc gtgatctatc ccgccggttg ggtggccgcc    60
gctcagctgg tcatgttcgc gatcgtcgcg gcgtcatgga ccctatatct gtggctgccg   120
cgtcggtagg caaactgccc gggcagtcgc ccgaacgtat ggtggacgta tgcgggcgtt   180
gatcatcgtc gacgtgcaga acgacttctg cgagggtggc tcgctggcgg taaccggtgg   240
cgccgcgctg gcccgcgcca tcagcgacta cctggccgaa gcggcggact accatcacgt   300
cgtggcaacc aaggacttcc acatcgaccc gggtgaccac ttctccggca caccggacta   360
ttcctcgtcg tggccaccgc attgcgtcag cggtactccc ggcgcggact ccatcccag    420 tctggacacg tcggcaatcg aggcggtgtt ctacaagggt gcctacaccg agcgtacag    480 cggcttcgaa ggagtcgacg agaacggcac gccactgctg aattggctgc ggcaacgcgg   540
cgtcgatgag gtcgatgtgg tcggtattgc caccgatcat tgtgtgcgcc agacggccga   600
ggacgcggta cgcaatggct tggccaccag ggtgctggtg gacctgacag cgggtgtgtc   660
ggccgatacc accgtcgccg cgctggagga gatgcgcacc gccagcgtcg agttggtttg   720
cagctcctga tggcaccgcc gaaccgggat gaactgttgg cggcggtgga gcgctcgccg   780
caagcggccg ccgcgcacga ccgcgccggc tgggtcgggt tgttcaccgg tgacgcgcgg   840
gtcgaagacc cggtgggttc gcagccgcag gtggggcatg aggccatcgg ccgcttctac   900
gacaccttca tcgggccgcg ggatatcacg ttccatcgcg atctggatat cgtctccggc   960

<210> SEQ ID NO 150
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
gacggatttg tcgctcac                                             18

<210> SEQ ID NO 151
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
agccaccctc gcagaa                                                      16

<210> SEQ ID NO 152
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
catcgtcgac gtgcagaa                                                    18

<210> SEQ ID NO 153
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
tgtccagact gggatggaa                                                   19

<210> SEQ ID NO 154
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
attgcgtcag cggtact                                                     17

<210> SEQ ID NO 155
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
tggccaagcc attgcgta                                                    18

<210> SEQ ID NO 156
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
atcattgtgt gcgccaga                                                    18

<210> SEQ ID NO 157
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157

```
caacagttca tcccggtt                                                 18

<210> SEQ ID NO 158
<211> LENGTH: 221
<212> TYPE: DNA
<213> ORGANISM: Mycobacterium tuberculosis

<400> SEQUENCE: 158
gacggatttg tcgctcacta catcaccggc gtgatctatc ccgccggttg ggtggccgcc   60
gctcagctgg tcatgttcgc gatcgtcgcg gcgtcatgga ccctatatct gtggctgccg  120
cgtcggtagg caaactgccc gggcagtcgc ccgaacgtat ggtggacgta tgcgggcgtt  180
gatcatcgtc gacgtgcaga acgacttctg cgagggtggc t                      221

<210> SEQ ID NO 159
<211> LENGTH: 245
<212> TYPE: DNA
<213> ORGANISM: Mycobacterium tuberculosis

<400> SEQUENCE: 159
catcgtcgac gtgcagaacg acttctgcga gggtggctcg ctggcggtaa ccggtggcgc   60
cgcgctggcc cgcgccatca gcgactacct ggccgaagcg gcggactacc atcacgtcgt  120
ggcaaccaag gacttccaca tcgacccggg tgaccacttc tccggcacac cggactattc  180
ctcgtcgtgg ccaccgcatt gcgtcagcgg tactcccggc gcggacttcc atcccagtct  240
ggaca                                                              245

<210> SEQ ID NO 160
<211> LENGTH: 246
<212> TYPE: DNA
<213> ORGANISM: Mycobacterium tuberculosis

<400> SEQUENCE: 160
attgcgtcag cggtactccc ggcgcggact tccatcccag tctggacacg tcggcaatcg   60
aggcggtgtt ctacaagggt gcctacaccg gagcgtacag cggcttcgaa ggagtcgacg  120
agaacggcac gccactgctg aattggctgc ggcaacgcgg cgtcgatgag gtcgatgtgg  180
tcggtattgc caccgatcat tgtgtgcgcc agacggccga ggacgcggta cgcaatggct  240
tggcca                                                             246

<210> SEQ ID NO 161
<211> LENGTH: 184
<212> TYPE: DNA
<213> ORGANISM: Mycobacterium tuberculosis

<400> SEQUENCE: 161
atcattgtgt gcgccagacg gccgaggacg cggtacgcaa tggcttggcc accagggtgc   60
tggtggacct gacagcgggt gtgtcggccg ataccaccgt cgccgcgctg gaggagatgc  120
gcaccgccag cgtcgagttg gtttgcagct cctgatggca ccgccgaacc gggatgaact  180
gttg                                                               184

<210> SEQ ID NO 162
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 162
accaccagca cctaaccggc tgtgggta                                              28
```

PCR READY COMPOSITIONS AND METHODS FOR DETECTING AND IDENTIFYING NUCLEIC ACID SEQUENCES

REFERENCE TO RELATED APPLICATIONS

This application is a continuation-in-part of U.S. application Ser. No. 14/048,905 entitled "Compositions and Methods for Detecting and Identifying Nucleic Acid Sequences in Biological Samples" filed Oct. 8, 2013, which issued at U.S. Pat. No. 9,481,912 on Nov. 1, 2016, and claims priority to U.S. Provisional Application No. 61/746,962 entitled "Noninterfering Multipurpose Compositions for Collecting, Transporting and Storing Biological Samples" filed Dec. 28, 2012, which is;

a continuation of International Application No. PCT/US2012/35253 entitled "Compositions and Methods for Detecting and Identifying Nucleic Acid Sequences in Biological Samples" filed Apr. 26, 2012, which claims priority to U.S. application Ser. No. 13/094,809 entitled "Compositions and Methods for Detecting, Identifying and Quantitating Mycobacterial-Specific Nucleic Acid" filed Apr. 26, 2011, which issued as U.S. Pat. No. 8,652,782 on Feb. 18, 2014;

a continuation-in-part of U.S. application Ser. No. 13/839,847 entitled "Compositions and Methods for the Collection and Isolation of Nucleic Acids from Biological Specimens" filed Mar. 15, 2013, presently pending, which claims priority to U.S. Provisional Application No. 61/616,676 filed Mar. 28, 2012;

a continuation-in-part of U.S. application Ser. No. 13/750,771 entitled "Composite Antigenic Sequences and Vaccines" filed Jan. 25, 2013, presently pending, which claims priority to U.S. Provisional Application No. 61/591,113 filed Jan. 26, 2012, which is;

a continuation-in-part of U.S. application Ser. No. 13/094,809 entitled "Compositions and Methods for Detecting, Identifying and Quantitating Mycobacterial-Specific Nucleic Acid" filed Apr. 26, 2011, which issued as U.S. Pat. No. 8,652,782 on Feb. 18, 2014, which is a continuation-in-part of U.S. application Ser. No. 12/916,263 entitled "Disposable, Rapid Extraction Apparatus and Methods" filed Oct. 29, 2010, presently pending;

a continuation-in-part of U.S. application Ser. No. 13/341,314 entitled "Compositions and Method for Rapid, Real-Time Detection of Influenza A Virus (H1N1) Swine 2009" filed Dec. 30, 2011, which issued as U.S. Pat. No. 9,080,204 on Jul. 14, 2015, which is a continuation of U.S. application Ser. No. 12/510,968 filed Jul. 28, 2009, which issued as U.S. Pat. No. 8,097,419 on Jan. 17, 2012; and a continuation-in-part of U.S. application Ser. No. 13/847,202 entitled "Biological Specimen Collection and Transport System and Method of Use" filed Mar. 19, 2013, which issued as U.S. Pat. No. 8,669,240 on Mar. 11, 2014, which is a continuation of U.S. application Ser. No. 13/632,272 filed Oct. 1, 2012, which issued as U.S. Pat. No. 8,415,330 on Apr. 9, 2013, which is a continuation of U.S. application Ser. No. 13/332,204 filed Dec. 20, 2011, which issued as U.S. Pat. No. 8,293,467 on Oct. 23, 2012, which is a continuation of U.S. application Ser. No. 12/243,949 filed Oct. 1, 2008, which issued as U.S. Pat. No. 8,084,443 on Dec. 27, 2011, which claims priority to U.S. Provisional Application No. 60/976,728 filed Oct. 1, 2007, and which is a continuation-in-part of U.S. application Ser. No. 11/844,933 entitled "Biological Organism Identification Product and Method" filed Aug. 24, 2007, now abandoned, which claims priority to U.S. Provisional Application No. 60/843,711 filed Sep. 12, 2006; and a continuation-in-part of U.S. application Ser. No. 14/969,339 entitled "Biological Specimen Collection/Transport Compositions and Methods" filed Dec. 15, 2015, presently pending, which is a continuation of U.S. application Ser. No. 13/328,992 filed Dec. 16, 2011, which issued as U.S. Pat. No. 9,416,416 on Aug. 16, 2016, which is a continuation of U.S. application Ser. No. 12/426,890 filed Apr. 20, 2009, which issued as U.S. Pat. No. 8,080,645 on Dec. 20, 2011, and a continuation-in-part of U.S. application Ser. No. 14/527,281 entitled "Next Generation Genomic Sequencing Methods" filed Oct. 29, 2014, presently pending, which claims priority to U.S. Provisional Application No. 61/897,015 filed Oct. 29, 2013, which is a continuation of U.S. application Ser. No. 13/890,512 filed May 9, 2013, which issued as U.S. Pat. No. 9,365,904 on Jun. 14, 2016, which claims priority to U.S. Provisional Application No. 61/737,250 filed Dec. 14, 2012, U.S. Provisional Application No. 61/695,960 filed Aug. 31, 2012, U.S. Provisional Application No. 61/646,060 filed May 11, 2012, and U.S. Provisional Application No. 61/644,876 filed May 9, 2012;

wherein all of the aforesaid patents and applications are specifically and entirely incorporated by reference.

SEQUENCE LISTING

This application contains a Sequence Listing which has been submitted in ASCII format and is hereby incorporated by reference in its entirety. Said ASCII copy, created on Oct. 25, 2016, is named 3022_008_USCP03_SL.txt and is 61,646 bytes in size.

FIELD OF THE INVENTION

The present invention generally relates to compositions and methods for detecting, identifying and optionally quantitating nucleic acid segments within a population of isolated polynucleotides such as obtained from a biological sample. In particular, the compositions and methods of the invention can be maintained for long periods of time at ambient temperatures without compromising the integrity of the components or the fidelity of the analysis.

BACKGROUND

Mycobacteria are unicellular, aerobic, Gram-positive bacteria. Typically, mycobacteria have a thick hydrophobic cell wall and lack an outer cell membrane. Infections caused by mycobacteria can be active within a host, or latent and asymptomatic. The emergence of multi-drug resistant strains, the need for prolonged antibacterial therapy, and poor patient compliance, has made treatment of mycobacterial infections difficult, particularly in developing nations. The emergence of multidrug resistant (MDR) strains of *M. tuberculosis*, in particular, has made diagnosis and treatment of TB a high priority in developing African populations.

Mycobacteria are typically classified as acid-fast Gram-positive bacteria due to their lack of an outer cell membrane. Acid-fast staining methods that are frequently used are the Ziehl-Neelsen stain or the Kinyoun method. They do not, generally, retain the crystal violet stain well and so are not considered a typical representative of Gram-positive bacteria. They do, however, contain a unique cell wall structure, which is thicker than that present in most other bacterial species. Typically, rod shaped, the cell wall consists of a hydrophobic mycolate layer (containing mycolic acids) and a peptidoglycan layer which is held together by arabinogalactan, a polysaccharide. This cell wall structure aids the mycobacteria in their ability to survive drastic environmental changes and contributes to the hardiness of the *Mycobacterium* species, as well in the difficulty in treating *tuberculosis* and leprosy patients, both of which are caused by different *Mycobacterium* species. Mycolic acids are strong hydrophobic molecules that form a lipid shell around the organism and affect permeability properties at the cell surface. Mycolic acids are thought to be a significant determinant of virulence in some *Mycobacterium* species. Most likely, they prevent attack of the mycobacteria by cationic proteins, lysozyme, and oxygen radicals in the phagocytic granule. They also protect extracellular mycobacteria from complement deposition in serum.

Additionally, Mycobacteria are typically slow growing organisms, contributing to the difficulty of culturing the species. Due to their unique cell wall, they can survive long exposure to acids, alkalis, detergents, oxidative bursts, lysis by complement, and many antibiotics. Most mycobacteria are susceptible to the antibiotics clarithromycin and rifamycin, but antibiotic-resistant strains have emerged.

Members of the *Mycobacterium tuberculosis* complex, i.e., *M. tuberculosis, M. bovis, M. africanum, M. microti, M. cannetti, M. caprae* and *M. pinnipedi*, the causative agents of *tuberculosis*, have all of the above stated characteristics of mycobacteria. The primary consequence of mycobacterial infection (and particularly, infection by one or more species of *Mycobacterium* genus) in humans is *tuberculosis* (TB or MTB), a contagious infection caused by members of the "*M. tuberculosis* complex," which include, e.g., pathogenic strains of the species *M. tuberculosis, M. bovis, M. africanum, M. microti, M. cannetti, M. caprae* and *M. pinnipedi*. TB typically attacks the lungs in mammalian hosts, but can also spread to other organs and regions of the body including, for example, bone, joints, kidneys, and the abdomen, etc. Members of the *M. tuberculosis* complex are closely related genetically, and possess highly-conserved 16S rRNA sequences across the genus.

TB can be acquired by breathing in air droplets from a cough or sneeze of an infected person. Accordingly, collection of biological samples suspected of containing members of the *M. tuberculosis* complex involves the collection of sputum from patients suspected of being infected with the same. Sputum is coughed up expectorate from the airways and ideally contains little to no saliva or nasal secretion, so as to avoid contamination of the sputum sample with oral bacteria. Sputum mainly contains mucus, a viscous colloid which is rich in glycoproteins. Patients suspected of having *tuberculosis* typically have an increased mucus viscosity, as well as increased production of mucus. In addition to mucus, sputum may contain blood, i.e., hemoptysis may occur, and/or pus, i.e., be purulent in nature. Symptoms of an active tubercular infection can include chronic cough (typically with blood-tinged sputum), fever, nocturnal hyperhidrosis, chronic fatigue, pallor, weight loss, and cachectic wasting ("consumption"). Other symptoms can include breathing difficulties, thoracic pain and wheezing ("Pulmonary *Tuberculosis*," PubMed Health). If an inhaled tubercle *bacillus* settles in a lung alveolus, infection occurs, followed by alveolocapillary dilation, and endothelial cell swelling. Alveolitis results with intracellular replication of the tubercle bacilli, and an influx of polymorphonuclear leukocytes to the alveoli. The organisms then spread through the lymph system to the circulatory system, and then throughout the body.

Although *M. tuberculosis* infects less than 200,000 people annually in the United States, according to the World Health Organization (WHO) nearly two billion people worldwide may be infected, 90% of whom can remain asymptomatic for years following infection. Left untreated, TB is fatal in >50% of the infected population, and in disseminated forms of the disease, the mortality rate approaches 90%.

Because of the chronic and debilitating persistence of TB infection, co-infection with one or more secondary pathogens, including in particular, human immunodeficiency virus (HIV), is also widespread. In 2007, there were at least 1.37 million cases of HIV-positive TB, concentrated primarily in emerging populations where diagnosis and treatment are often limited, ineffective, and/or cost-prohibitive.

Conventional diagnosis of a TB infection typically relies on a combination of physical examination (e.g., chronic persistent cough, enlarged or tender lymph nodes, pleural effusion, unusual breath sounds, and, in later stages of the disease, characteristic "clubbing" of the fingers or toes) and diagnostic testing (e.g., sputum examination, microbial culture and nucleic acid testing of specimens, bronchoscopy, CT scan or X-ray of the chest, pulmonary biopsy, thoracentesis, interferon-γ (gamma) blood test, and tuberculin skin test).

The "standard" of TB diagnostics, cell culturing of mycobacterial organisms, is difficult, due in part to their long generation times, i.e., twenty-four hours for *M. tuberculosis*. In addition, mycobacteria are typically present at low levels in infected individuals. Culturing from a clinical specimen can therefore take anywhere between four to eight weeks, during which time a patient may become seriously ill and contagious to others. In addition, cell culturing requires the collection, transport and maintenance of viable mycobacterial organisms in a sample until such time as the sample can be analyzed in a lab setting. In countries where TB is prevalent, and health care is minimal, this may not be an option, thus increasing the risk of spreading infection.

Unfortunately for regions with limited access to medical care, the whole blood must be analyzed within 12 hours of obtaining the sample, and the effectiveness of the test has not been analyzed on patients with other medical conditions such as HIV, AIDS, diabetes, silicosis, chronic renal failure, hematological disorders, individuals that have been treated for TB infection, nor has it been tested on pregnant individuals or minors ("Clinicians Guide to QuantiFERON®-TB Gold," Cellestis). Other non-culture methods such as radioimmunoassays, latex agglutination, and enzyme-linked immunosorbent assays (ELISAs) have been used with limited degrees of success to confirm the presence of tubercle bacilli in biological samples.

The majority of clinical diagnostic laboratories employed traditional culture for pathogen identification that typically requires 3-7 days for most viruses and longer for some bacterial strains, including up to about 21 days for the culturing of *M. tuberculosis*. Traditional culture requires specimen collection of viable microbes, frozen transport, and propagation and handling of potentially infectious and often unknown biological microbes. Furthermore, many infectious agents, e.g., highly pathogenic avian influenza, SARS, *M. tuberculosis* complex, etc., are BSL-3 level pathogens that require specialized facilities and precautions for analysis. There are challenges in obtaining, shipping and maintaining high-quality, viable biological specimens for culture. Specimens must be shipped using a cold chain, most often dry ice. Transporting potentially infectious samples from remote sites or across international borders using commercial transit can be costly and tedious, particularly when specimens must be received frozen.

Collection is the first step in diagnostic platforms or molecular protocols requiring the detection of potentially minute amounts of nucleic acids from microbes. Regardless of the nucleic acid test used or the RNA/DNA extraction protocol, specimen collection, specifically the inactivation of potentially infectious agents and the preservation and stability of pathogen RNA/DNA remains a critical gap in clinical diagnostics, especially for use around the world.

Typically, patients suspected of having *tuberculosis* are asked to cough hard and then expectorate into a specimen cup in order to obtain a sputum sample. Usually, this procedure is done in a well ventilated area so as to minimize the potential for spreading infective mycobacteria. Patients may be asked to repeat this procedure in order to collect enough sputum for analysis, typically in amounts from about 5 mL to about 20 mL. Typically, collected sputum samples are refrigerated until further analytic procedures, such as cell culturing or decontamination procedures to inactivate or kill any microorganisms contained within the sample, can be performed. In order to detect *Mycobacterium tuberculosis* in a sputum sample, an excess of 10,000 organisms per mL of sputum are needed to visualize the bacilli with a 100× microscope objective (1000× magnification). Direct smear microscopy of sputum samples from *tuberculosis* patients is typically regarded as an effective tool for monitoring patient response to treatment. Typically, more acid fast bacilli will be found in the purulent portions of the sputum. The field of clinical molecular diagnostics changed drastically with the advent of polymerase chain reaction (PCR), and subsequently, real-time PCR. Real-time (RT-PCR) and real-time reverse transcription PCR (rRT-PCR) can deliver superior sensitivity and specificity results in hours. Thus, the majority of current diagnostic laboratories have transitioned from traditional culture to nucleic acid testing (NAT) such as real-time PCR.

Nucleic acid amplification testing for TB includes the use of standard polymerase chain reaction (PCR) techniques to detect mycobacterial DNA in patient specimens, nucleic acid probes to identify mycobacteria in culture, restriction fragment length polymorphism (RFLP) analysis to compare different strains of TB for epidemiological studies, and genetic-based susceptibility testing to identify drug-resistant strains of mycobacteria. The complete genome of *M. tuberculosis* has been sequenced and published; currently two nucleic acid amplification-based tests for TB have been approved for use in the United States by the Food and Drug Administration (FDA). The first, known as the "Enhanced Amplified *Mycobacterium Tuberculosis* Direct Test" (E-MTD, Gen-Probe, San Diego, Calif., USA), is approved for detection of *M. tuberculosis* complex bacteria in acid-fast bacilli in both smear-positive and smear-negative respiratory specimens from patients suspected of having TB. The E-MTD test combines isothermal transcription-mediated amplification of a portion of the 16S rRNA with a detection method that uses a hybridization probe specific for *M. tuberculosis* complex bacteria. The second, known as the AMPLICOR® *Mycobacterium tuberculosis* Test (AMPLICOR®, Roche Diagnostics, Basel, Switzerland), has been approved for the detection of *M. tuberculosis* complex bacteria only in smear-positive respiratory specimens from patients suspected of having TB. This test uses PCR to amplify a portion of the 16S rRNA gene that contains a sequence that hybridizes with an oligonucleotide probe specific for *M. tuberculosis* complex bacteria. ("Report of an Expert Consultation on the Uses of Nucleic Acid Amplification Tests for the Diagnosis of *Tuberculosis*," Centers for Disease Control and Prevention).

Results have indicated that the sensitivity and specificity of these tests tends to vary depending on geographical location and risk factors. In addition, these techniques require complex laboratory conditions and equipment to be performed, thus reducing the speed and sensitivity of the test. For these and other reasons, there remains a need in the art for reliable and accurate methods for detection of Mycobacterial pathogens in clinical samples, and in particular, methods for rapidly identifying such pathogens in field applications, remote locations, and in developing countries where conventional laboratories are lacking, and financial resources are limited. In particular, compositions for the safe collection, handling, and transport of pathogenic specimens, as well as molecular biology-based methods for the rapid detection and accurate identification of TB-specific nucleic acids in such specimens are highly desired.

SUMMARY OF THE INVENTION

The present invention overcomes the problems and disadvantages associated with current strategies and designs, and provides new composition, tools and methods for detecting and identifying nucleic acid sequences.

One embodiment of the invention is directed to PCR-ready compositions for detection of a microorganism in a biological sample comprising as components: a heat-stable polymerase present in an amount from about 0.05 U to about 1 U; a mix of deoxynucleotide tri phosphates comprising about equivalent amounts of dATP, dCTP, dGTP and dTTP, collectively present in the composition at a concentration of about 0.1 mM to about 1 mM; a chelating agent selected from the group consisting of ethylene glycol tetraacetic acid, hydroxyethylethylenediamine triacetic acid, diethylene triamine pentaacetic acid, N,N-bis(carboxymethyl)glycine, ethylenediaminetetraacetic, citrate anhydrous, sodium citrate, calcium citrate, ammonium citrate, ammonium bicitrate, citric acid, diammonium citrate, potassium citrate, magnesium citrate, ferric ammonium citrate, lithium citrate, and any combination thereof, present in the composition at a concentration of about 0.01 mM to about 1 mM; a PCR osmolarity agent selected from the group consisting of N,N,N-trimethylglycine (betaine), dimethyl sulfoxide (DMSO), foramide, glycerol, non-ionic detergents, polyethylene glycol, tetramethylammonium chloride, and any combination thereof, present in the composition at a concentration of about 1 mM to about 1 M; an albumin selected from the group consisting of bovine serum albumin, human serum albumin, goat serum albumin, mammalian albumin, and any combination thereof, present in the composition at a concentration of about 5 ng/ml to about 100 ng/ml; at least two salts, the first being a potassium salt selected from the group consisting of potassium chloride and potassium glutamate and the second being a magnesium salt selected from the group consisting of magnesium chloride and magnesium sulfate, collectively present in the composition at a concentration of about 50 mM to about 1 M; and a buffer selected from the group consisting of tris(hydroxymethyl) aminomethane (Tris), citrate, 2-(N-morpholino)ethanesulfonic acid (MES), N,N-Bis(2-hydroxyethyl)-2-aminoethanesulfonic acid (BES), 1,3-bis(tris(hydroxymethyl) methylamino) propane (Bis-Tris), 4-(2-hydroxyethyl)-1-piperazineethanesulfonic acid (HEPES), 3-(N-morpholino)propanesulfonic acid (MOPS), N,N-bis(2-hydroxyethyl) glycine (Bicine), N-[tris(hydroxymethyl)methyl]glycine (Tricine), N-2-acetamido-2-iminodiacetic acid (ADA), N-(2-acetamido)-2-aminoethanesulfonic acid (ACES), piperazine-1,4-bis(2-ethanesulfonic acid) (PIPES), bicarbonate, phosphate, and any combination thereof, present in the composition at a concentration of about 1 mM to about 1 M and with a pH of about 6.5 to about 9.0, wherein the pKa of the buffer (or average pKa for buffers with multiple buffering moieties) of the composition is within about one unit of the pH of the composition at a selected temperature. As the pH can be adjusted by the skilled individual, the more preferred buffer is one wherein the largest buffering capacity of the buffer overlaps the actual and/or eventual or desired pH of the composition. Also preferably the components are combined with nuclease-free water (RNase-free and/or DNase free).

Preferably the heat-stable polymerase is a Taq polymerase, a high fidelity polymerase, a Pfu polymerase, a hot start polymerase, or a next gen polymerase. Preferably the composition further comprises one or more dyes selected from the group consisting of fluorescein, 5-carboxy-X-rhodamine and ROX. Preferably the pH of the buffer or the overall composition is from about 6.5 to about 7.5, and the pKa of the buffer is within 0.5 of the pH of the buffer at ambient temperature, more preferably the pKa of the buffer is within 0.2 of the pH of the buffer at ambient temperature. Preferably the composition further comprises a pair of PCR primers configured to amplify by PCR a nucleic acid sequence that is specific for the microorganism, collectively present in the composition at a concentration of about 0.5 µM to about 50 µM, wherein each PCR primer is from about 5 to about 50 nucleotides in length. More preferably each primer of the pair of PCR primers is from about 18 to 35 nucleotides in length. Preferably the microorganism to be detected is a pathogen which may be a bacterial, viral, fungal or parasitic pathogen. More preferably the bacteria is mycobacteria or the virus is influenza virus such as, for example, influenza virus strain H1N1, H2N2, H3N3 or H5N1. Preferably the composition further comprises a control nucleic acid present in the concentration at a concentration of about 1 fg to about 1 ng which provides a qualitative or quantitative measure of PCR amplification. Preferred control nucleic acid comprises, for example, the sequence of SEQ ID NO 8, the sequence of SEQ ID NO 12, or the sequence of SEQ ID NO 21. Preferably the composition may further contain a detection probe, such as, for example, a detection probe that specifically binds to a PCR amplified nucleic acid sequence that is specific to the microorganism. A preferred composition of the invention contains about 50 mM of TRIS; about 70 mM of potassium chloride; about 3 mM of magnesium sulfate; about 45 mM of betaine; about 0.03 µg/mL of bovine serum albumin; about 0.1 mM of EDTA; about 0.05 µM of dye; about 8 µM of the pair of PCR primers. Preferably one primer of the pair of PCR primers comprises the nucleic acid sequence of SEQ ID NO 2 or SEQ ID NO 5, and the other primer of the pair of PCR primers comprises the nucleic acid sequence of SEQ ID NO 3 or SEQ ID NO 6. Also preferred is the composition wherein the detection probe is a *Mycobacterium*-specific sequence of about 20 to about 35 nucleotides in length and comprises the sequence of SEQ ID NO 4 or SEQ ID NO 7.

Another embodiment of the invention comprises PCR-ready compositions for detection of a microorganism in a biological sample comprising as components: a heat-stable polymerase; a mix of deoxynucleotide tri phosphates comprising about equivalent amounts of dATP, dCTP, dGTP and dTTP; a chelating agent; a PCR osmolarity agent; an albumin; at least two salts; and a buffer which is present in the composition at a concentration of at least 50 mM and has a pH of about 6.5 to about 9.0, wherein the pKa of the buffer is within about one unit of the pH at a selected temperature, wherein the components are combined with nuclease-free water. Preferably the heat-stable polymerase is present in an amount from about 0.05 U to about 10 U; the mix of deoxynucleotide tri phosphates is present in the composition at a concentration of about 0.1 mM to about 10 mM; the chelating agent is present in the composition at a concentration of about 0.01 mM to about 10 mM; the PCR osmolarity agent is present in the composition at a concentration of about 1 mM to about 10 M; the albumin is present in the composition at a concentration of about 5 ng/ml to about 1 mg/ml; the at least two salts are collectively present in the composition at a concentration of about 50 mM to about 10 M; and the buffer is present in the composition at a concentration of about 1 mM to about 10 M.

Another embodiment of the invention is directed to methods for detection of a microorganism in a biological sample comprising: contacting the biological sample to the composition of any one of claims 1-22 to form a mixture; performing multiple thermal cycling steps on the mixture to form an amplification product that is derived from the nucleic acid that is specific for the microorganism; detecting the presence or absence of the amplification product to determine the presence or absence of the microorganism in the biological sample. Preferably the method further comprises detecting an amplified sequence of a control nucleic acid and determining the quality or quantity of amplification which occurred from the multiple thermal cycling steps. Also preferably, the biological sample comprises biological material obtained from an individual, one or more chaotropes, one or more detergents, one or more reducing agents, one or more chelators, and one or more buffers.

Another embodiment of the invention is directed to methods of providing for detection of a microorganism in a biological sample comprising providing a PCR-ready composition containing as components: a heat-stable polymerase present in an amount from about 0.05 U to about 1 U and/or a reverse transcriptase sufficient to generate DNA sequences from RNA sequences of interest; a mix of deoxynucleotide tri phosphates comprising about equivalent amounts of dATP, dCTP, dGTP and dTTP, collectively present in the composition at a concentration of about 0.1 mM to about 1 mM; one or more chelating agents present in the composition at a concentration of about 0.01 mM to about 1 mM; one or more PCR osmolarity agents present in the composition at a concentration of about 1 mM to about 1 M; one or more albumin proteins present in the composition at a concentration of about 5 ng/ml to about 100 ng/ml; one or more salts present in the composition at a concentration of about 50 mM to about 1 M; and one or more buffers present in the composition at a concentration of about 1 mM to about 1 M and with a pH of about 6.5 to about 9.0, wherein the pKa of the buffer is within about one unit of the pH at a selected temperature, wherein the components are combined with nuclease-free water. Preferably the pH of the buffer is from about 6.5 to 7.5 and the pKa is within about 0.5 units of the pH at an ambient temperature. Preferably the method further comprises contacting the biological sample with the composition and performing a thermal cycling reaction on the mixture. Preferably the one or more chelating agents comprise ethylene glycol tetraacetic acid, hydroxyethylethylenediaminetriacetic acid, diethylene triamine pentaacetic acid, N,N-bis(carboxymethyl)glycine, ethylenediaminetetraacetic, citrate anhydrous, sodium citrate, calcium citrate, ammonium citrate, ammonium bicitrate, citric acid, diammonium citrate, potassium citrate, magnesium citrate, ferric ammonium citrate, lithium citrate, or any combination thereof, the one or more PCR osmolarity agents comprise N,N,N-trimethylglycine (betaine), dimethyl sulfoxide (DMSO), foramide, glycerol, non-ionic detergents, deoxyinosine, glycerine, 7-deaza deoxyguanosine triphosphate, sodium hydroxide, polyethylene glycol, tetramethylammonium chloride, or any combination thereof, the one or more albumins comprises bovine serum albumin, human serum albumin, goat serum albumin, mammalian albumin or any combination thereof, the one or more salts comprise potassium chloride, potassium glutamate, magnesium chloride, magnesium sulfate, and any combination thereof, the one or more buffers comprise tris(hydroxymethyl) aminomethane (Tris), citrate, 2-(N-morpholino)ethanesulfonic acid (MES), N,N-Bis(2-hydroxyethyl)-2-aminoethanesulfonic acid (BES), 1,3-bis(tris(hydroxymethyl) methylamino) propane (Bis-Tris), 4-(2-hydroxyethyl)-1-piperazineethanesulfonic acid (HEPES), 3-(N-morpholino)propanesulfonic acid (MOPS), N,N-bis(2-hydroxyethyl) glycine (Bicine), N-[tris(hydroxymethyl)methyl]glycine (Tricine), N-2-acetamido-2-iminodiacetic acid (ADA), N-(2-acetamido)-2-aminoethanesulfonic acid (ACES), piperazine-1,4-bis(2-ethanesulfonic acid) (PIPES), bicarbonate, phosphate, or any combination thereof.

Another embodiment of the invention is directed to kits comprising the composition of the invention contained within a sterile vessel configured for addition of a biological sample and thermal cycling, and instructions for determining the presence or absence of a pathogen from the results of the thermal cycling.

Other embodiments and advantages of the invention are set forth in part in the description, which follows, and in part, may be obvious from this description, or may be learned from the practice of the invention.

DESCRIPTION OF THE INVENTION

Figure 1:
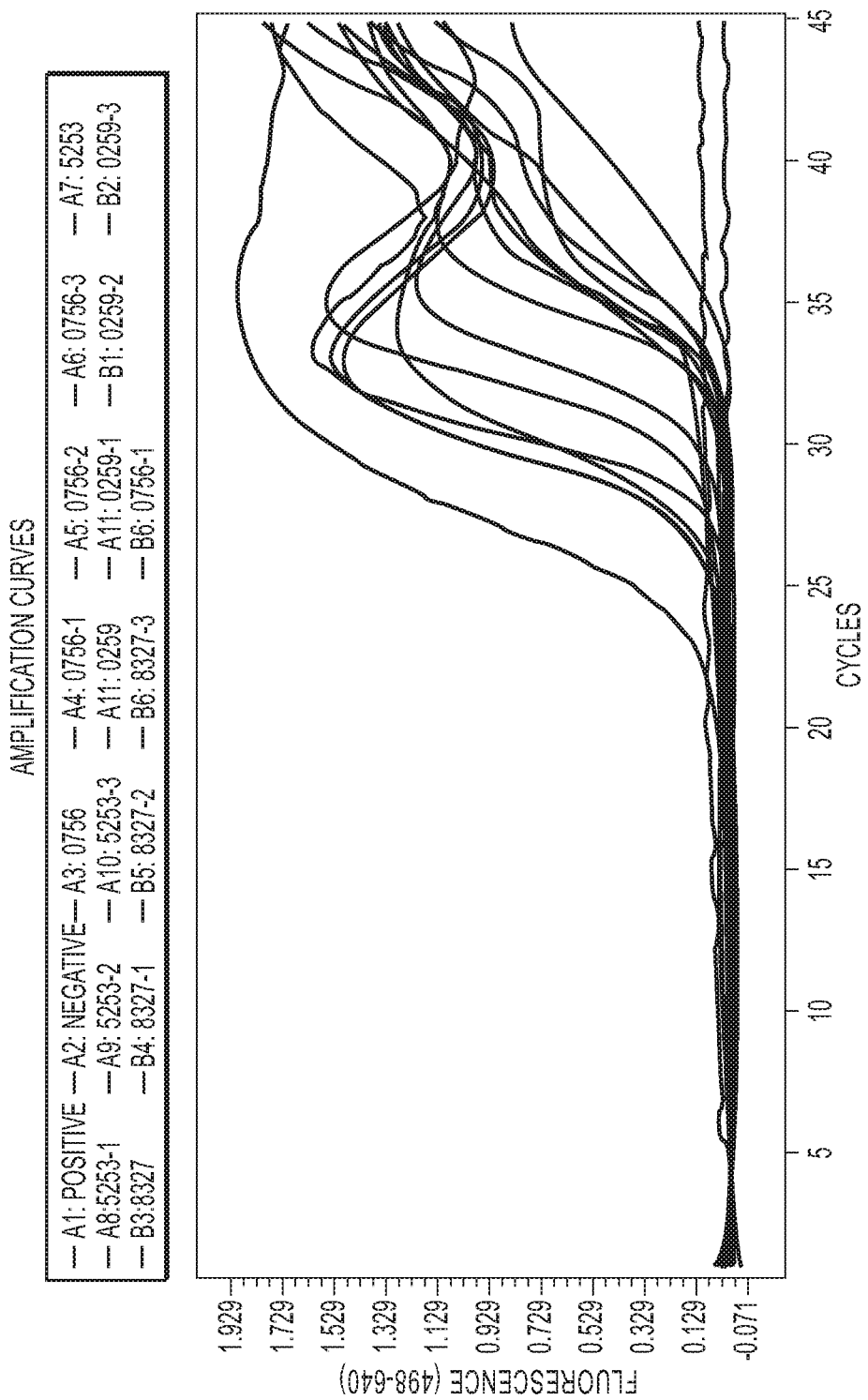
FIG. 1 illustrates the real time (RT) PCR analysis of tuberculin DNA from positive smear sputum samples preserved in PrimeStore® in a 1:1 ratio. In addition, the same smear positive sputum samples were swabbed, resulting in about 50 to about 400 microliters of sample on the swab, and the swabs placed in 1.5 mL of PrimeStore®. DNA was extracted from each sputum sample in PrimeStore® using the AMPLICOR® Respiratory Specimen Preparation Kit (AMPLICOR®, Roche Diagnostics, Basel, Switzerland) according to manufacturer's instructions. Four microliters of extracted DNA was used for real-time PCR using the LightCycler® Mycobacterium detection kit, according to the manufacturer's instructions. The resulting Cτ values for each of the samples is shown in Table 2.

The present invention overcomes these and other inherent limitations in the prior art by providing useful, non-obvious, and novel compositions to safely collect, handle and transport biological samples suspected of containing pathogenic organisms, as well as methods for rapidly detecting, identifying and quantitating those pathogens through molecular biology-based nucleic acid testing. In particular, methods are provided for specifically detecting one or more strains of pathogenic microorganisms such as bacteria, viruses, fungus and parasites. In particular applications, the invention encompasses a diagnostic product that permits the collection of a target specimen, preparation of the target specimen for assaying, isolation of genomic material from the specimen, and subsequent processing of the genomic material to identify one or more organisms, if present, in the biological sample. When coupled with one or more specimen collection devices, the compositions disclosed herein permit safe, collection, transport and storage of biological specimens, even for those collected in remote or "field" applications, wherein the time from sample collection to sample assay may be hours to days, or even weeks.

The invention further encompasses compositions and methods that simplify and expedite specimen collection, preparation and molecular detection of microorganisms, specifically those microorganisms that are the causative agents of influenza and *tuberculosis*. In particular applications, the invention encompasses a diagnostic product whereby the specimen is collected, transported and rapidly prepared for downstream PCR without the need for a cold chain or costly and time-consuming sample decontamination and specimen emulsification. The molecular diagnostic product includes a thermo-stabile, all-inclusive PCR mixture of primers, probes and enzymes in a ready-to-use solution or suspension. This diagnostic product can be used in central labs and with high through-put systems or in rural or mobile clinics with minimal capabilities and in the absence of reliable community electric power, or even with a hand-held device. The invention also encompasses a method for epidemiologic and outbreak surveillance, pandemic and epidemic tracking and microbial sequencing directly from field samples at the site of collection or by using inexpensive, simplified, safe shipping through standard mail at ambient temperature. This invention also encompasses a diagnostic molecular detection kit for safe site of care collection, rapid extraction and rapid PCR detection of microbes, specifically pathogens.

Using the pathogen-specific nucleic acid detection probes and amplification primers disclosed herein, the present invention also provides facile identification of pathogens in collected samples, and permits a safe, cost-effective, and near-term assessment of infection, including, for example, as a tool in surveillance against potential epidemics, monitoring of outbreaks, assessment of disease progression in affected or at-risk populations, and/or identification of particular species and/or strains of the microorganism for diagnostic testing or determining particular therapeutic modalities.

In one embodiment, the invention provides a method for obtaining a population of specific polynucleotides from a sample suspected of containing one or more pathogenic microorganisms, or pathogenic or pathogen infected cells (collectively "pathogens"). In an overall sense, this method generally involves contacting a sample suspected of containing one or more pathogens for an effective amount of time and with a sufficient amount of a composition that includes: a) one or more chaotropes; b) one or more detergents; c) one or more reducing agents; d) one or more chelators; and e) one or more surfactants, to kill substantially all, and preferably to kill all of the pathogenic organisms therein, including, for example, pathogenic bacteria, fungi, and viruses (if present in the sample). In the practice of the method, substantially all (and preferably, all) of the cells and microorganisms contained therein are lysed, and their cellular contents liberated into the solution. Preferably, substantially all (and more preferably, all) of the cellular enzymes, proteins, peptides, lipoproteins, and other cellular contents are denatured and/or inactivated, including any exogenous or endogenous nucleases that may be present in the sample, such that the resulting mixture is rendered substantially safe (and preferably, safe) for handling, storage, and/or transport by workers without undue effects, and without the need for concern over pathogenicity, toxicity, or danger of handling the sample now that it has been decontaminated and any pathogenic organisms originally present therein, destroyed, inactivated, killed, and/or lysed to render them harmless. Compositions for the collection of biological samples may be maintained in ready-to-use concentrations, or in concentrated forms such as, for example, 2×, 5×, 10×, 20× 25×, 30×, or greater as convenient or necessary for the particular application.

Preferably the population of polynucleotides so obtained from the method will preferably be substantially stable, such that the nucleic acids do not substantially degrade, and the integrity of the obtained population of polynucleotides will preferably be at least substantially maintained, so that the obtained polynucleotides are substantially intact, and present in the sample in the form that they were in when the cells containing them were initially liberated/lysed by the action of the components present in the composition. As noted herein, in preferred applications of the invention, the population of pathogen-specific polynucleotides obtained using the disclosed methods are substantially stable and non-degraded such that they can be maintained for significant periods of time even at less-than-ideal ambient temperatures (e.g., at a temperature of about 0° C. to even about 40° C. or more) for extended periods of time (e.g., for periods of several hours to several days to several week or months even) without significantly degrading the liberated nucleic acids, thereby making them suitable for downstream molecular analysis (e.g., template-dependent amplification reactions et al.) days to weeks after extraction of the nucleic acids takes place, even when it is not possible to store the populations of polynucleotides extracted from the samples frozen, on ice, or refrigerated between initial sample collection and subsequent molecular analysis.

As noted herein, in preferred embodiments, the (i) the one or more chaotropes preferably include guanidine thiocyanate, guanidine isocyanate, guanidine hydrochloride, or any combination thereof; (ii) the one or more detergents preferably include sodium dodecyl sulfate, lithium dodecyl sulfate, sodium taurodeoxycholate, sodium taurocholate, sodium glycocholate, sodium deoxycholate, sodium cholate, sodium alkylbenzene sulfonate, N-lauroyl sarcosine, or any combination thereof; (iii) the one or more reducing agents preferably include 2-mercaptoethanol, tris(2-carboxyethyl) phosphine, dithiothreitol, dimethylsulfoxide, or any combination thereof; (iv) the one or more chelators preferably include ethylene glycol tetraacetic acid, hydroxyethylethylenediaminetriacetic acid, diethylene triamine pentaacetic acid, N,N-bis(carboxymethyl)glycine, ethylenediaminetetraacetic, citrate anhydrous, sodium citrate, calcium citrate, ammonium citrate, ammonium bicitrate, citric acid, diammonium citrate, ferric ammonium citrate, lithium citrate, or any combination thereof; or (v) the one or more buffers preferably include tris(hydroxymethyl) aminomethane, citrate, 2-(N-morpholino)ethanesulfonic acid, N,N-Bis(2-hydroxyethyl)-2-aminoethanesulfonic acid, 1,3-bis(tris(hydroxymethyl)methyl amino)propane, 4-(2-hydroxyethyl)-1-piperazine ethanesulfonic acid, 3-(N-morpholino) propanesulfonic acid, bicarbonate, phosphate, or any combination thereof.

Preferred formulations that are at ready-to-use concentrations include: (a)(i) about 3 M guanidine thiocyanate; (ii) about 1 mM TCEP; (iii) about 10 mM sodium citrate; (iv) about 0.5% N-lauroyl sarcosine; (v) about 0.0002% silicone polymer; (vi) about 100 mM 2-amino-2-hydroxymethyl-propane-1,3-diol (TRIS); and (vii) about 0.1 mM EDTA; or (b) (i) about 3 M guanidine thiocyanate; (ii) 1 mM TCEP; about 10 mM sodium citrate; (iii) about 0.5% N-lauroyl sarcosine, sodium salt; (iv) about 0.0002% of a silicone polymer; (v) about 100 mM TRIS; (vi) about 0.1 mM EDTA; and (vii) about 10% to about 25% ethanol (vol./vol.).

Because of the remarkable effectiveness of the disclosed formulations in readily killing, and lysing the cells, denaturing the proteinaceous cellular components and inactivating enzymes such as endogenous and exogenous nucleases that are deleterious to the preservation of intact nucleic acids, the inventors have demonstrated that in certain instances, substantially all of the microorganisms present in a sample are killed and/or lysed within the first few minutes it is contacted with the composition. In some instances, the killing and lysing of the cells is substantially complete within about 3 or about 4 or about 5 or so minutes of contacting the sample with the composition. Likewise, in other instances, contacting the sample with the composition for a period of about 6, or about 7, or about 8, or about 9, or about 10 minutes or so is sufficient to substantially kill and/or lyse all of the pathogens that may be present in the collected sample. Likewise, substantially all of the proteins, enzymes, nucleases, and the like liberated from the lysed cells present in a sample are substantially all inactivated and/or denatured within only a few minutes of contacting the sample with the composition.

Preferably the samples will be of biological, clinical, veterinary, or environmental origin, and in certain embodiments, the samples are preferably of human origin, and in particular, from humans that have, are suspected of having, or are at risk for developing a microbial infection, such as a tubercular infection caused by one or more strains or species of the genus *Mycobacterium*. The individuals from which the samples are taken may be patients that also have, are suspected of having, or are at risk for developing one or more secondary or tertiary medical conditions, and in particular, a secondary and/or tertiary infection by one or more non-pathogenic species of bacteria, or one or more pathogenic species of fungal or viral origin, or any combination thereof.

Preferably the population of nucleic acid segments contained with the plurality of isolated and purified polynucleotides obtained from a sample will be suitable for primer-dependent amplification, and particularly so, when the polynucleotides are stored in the composition for a period of about 1 to about 90 days between the time of sample collection and molecular analysis, even when stored at less-than-ideal storage conditions, including, for example, storage under ambient temperature of about 0° C. to about 40° C., preferably at ambient temperatures.

In some embodiments, the method further includes the step of detecting within the obtained population of pathogen-specific polynucleotides the presence of at least a first pathogen-specific nucleic acid segment by contacting the population with a labeled oligonucleotide detection probe, wherein the presence of a labeled hybridization product is indicative of the presence of one or more pathogen-specific nucleic acid segments in the obtained population of polynucleotides. For RNA nucleic acids, reverse transcriptase may be included before or with a heat-stable polymerase to create DNA sequences for PCR amplification.

In exemplary embodiments, the labeled oligonucleotide detection probe includes at least a first sequence region that consists of the sequence of SEQ ID NO:4 or SEQ ID NO:7. The composition may further initially include a known quantity of at least a first internal positive control nucleic acid segment of about 50 to about 500, alternatively, about 70 to about 250, or alternatively still, about 90 to about 150 nucleotides in length, wherein the internal positive control nucleic acid segment does not substantially hybridize to genomic nucleic acids of the host from which the sample was obtained, nor to genomic nucleic acids of a pathogen. Such IPCs are disclosed herein in detail, and may include a single-stranded DNA, a double-stranded DNA, a single-stranded RNA, a double-stranded RNA, or a double-stranded DNA:RNA hybrid. In certain embodiments, the IPC nucleic acid segment includes an at least 40-contiguous nucleotide sequence, an at least 50-contiguous nucleotide sequence, an at least 60-contiguous nucleotide sequence, an at least 70-contiguous nucleotide sequence, or an at least 80-contiguous nucleotide sequence from SEQ ID NO: 8, or the complement thereof.

In exemplary embodiments, the IPC includes: (a) a first sequence domain that specifically binds to a labeled oligonucleotide detection probe of from about 15 to about 40 nucleotides in length, from about 18 to about 35 nucleotides in length, or from about 20 to about 30 nucleotides in length, that is specific for the first internal positive control nucleic acid segment; (b) a second sequence domain that specifically binds to a forward PCR amplification primer of about 15 to about 45 nucleotides in length, about 25 to about 35 nucleotides in length, or about 20 to about 30 nucleotides in length; and (c) a third sequence domain that specifically binds to a reverse PCR amplification primer of about 15 to about 45 nucleotides in length, about 18 to about 40 nucleotides in length, about 21 to about 35 nucleotides in length, or about 24 to about 30 nucleotides in length, wherein the second and third sequence domains are operably positioned upstream, and downstream, respectively, of the first sequence domain to facilitate a PCR-directed amplification of at least a first portion of the internal positive control nucleic acid segment from the forward and reverse primers under conditions effective to amplify the at least a first portion.

The method may also preferably further include at least the steps of (a) performing at least one thermal cycling step, wherein the cycling comprises at least a first amplifying step and at least a first hybridizing step, wherein the at least a first amplifying step comprises contacting the obtained population of polynucleotides with a composition that comprises at least a pair of distinct, independently-selected, specific amplification primers, a thermostable polymerase, a first osmolarity agent comprising betaine or another cationic functionalized zwitterionic compound, at least a first reference dye, and a plurality of deoxynucleoside triphosphates to produce at least a first pathogen-specific amplification product; and (b) detecting the presence of the amplification product so produced by contacting it with a first labeled pathogen-specific oligonucleotide detection probe, wherein the presence of a labeled hybridization product is indicative of the presence of one or more pathogen-specific nucleic acid segments in the obtained population of polynucleotides. In such embodiments, the pair of distinct, independently-selected, pathogen-specific amplification primers may preferably include a first oligonucleotide primer of 18 to about 30 nucleotides in length, and a second oligonucleotide primer of 18 to about 30 nucleotides in length, wherein each of the first and second primers specifically hybridize to a first, and a second distinct sequence region, respectively. For the detection and identification of Mycobacteria, preferably the pair of primers amplify at least a portion of the sequence of SEQ ID NO:1 or the complement thereof.

In related embodiments, the method of the present invention may further optionally include the step of performing a primer-dependent amplification of at least a first sequence region of the internal positive control nucleic acid segment in the obtained population of polynucleotides, and quantitating the amount of the internal positive control nucleic acid segment present in the obtained population of polynucleotides.

Likewise, the method may further optionally include the step of comparing the amount of the internal positive control nucleic acid segment present in the composition at one or more steps along the analytical process, to the amount of IPC that was present in the original composition before the sample was initially added to the lysis/storage/transport medium, or to the amount of target nucleic acids that were present in the original composition. Such comparison may serve to demonstrate that the amount of IPC still contained in the sample in a downstream point of assay is comparable to, or substantially the same as, the known amount of IPC that was present in the MTM composition before the sample was added to it, and may serve to quantitate the amount of target nucleic acids of interest in the collected samples, or downstream assayed components. Such information may also be indicative of the amount of the nucleic acids remaining in the sample as compared to what was originally present, and may provide an estimate of the degree of sample degradation of the polynucleotides originally present over time.

In some applications of the present technology, the primer-dependent amplification of the least a first sequence region of the internal positive control nucleic acid segment is performed subsequent to the amplification of the pathogen-specific nucleic acid segment, while in other aspects, the primer-dependent amplification of the least a first sequence region of the internal positive control nucleic acid segment is performed substantially simultaneously with the amplification of the pathogen-specific nucleic acid segment.

The amplification product of the internal positive control nucleic acid segment may be detected with a suitable oligonucleotide detection probe comprising a first detectable label, and the amplification product of the pathogen-specific nucleic acid segment is detected with an oligonucleotide detection probe comprising a second distinct detectable label.

Such method may also further optionally include detecting the presence of one or more drug resistance genes within the population of obtained polynucleotides.

The invention also provides a primer-dependent amplification reaction-compatible composition that preferably includes (a) one or more buffers; (b) one or more osmolarity agents; (c) one or more albumin proteins; (d) one or more chelators; (e) one or more salts; (f) at least a pair of distinct, independently-selected, pathogen-specific amplification primers, wherein each of the first and second primers specifically hybridize to a first, and a second distinct sequence region; (g) a pathogen-specific oligonucleotide detection probe comprising a first detectable label, that specifically hybridizes to a third sequence region; (h) at least one primer-dependent amplification reaction-capable thermostable polymerase; and (i) a plurality of deoxynucleoside triphosphates, each present in an amount sufficient to enable the amplification of at least a first pathogen-specific amplification product. Compositions that are thermal-cycling ready (e.g., PCR ready) may be maintained in ready-to-use concentrations, or in concentrated forms such as, for example, 2×, 5×, 10×, 20× 25×, 30×, or greater as convenient or necessary for the particular application.

In illustrative embodiments, (a) the one or more buffers preferably include tris(hydroxymethyl)aminomethane (TRIS); (b) the one or more polymerase chain reaction osmolarity agents preferably include N,N,N-trimethylglycine (betaine), dimethyl sulfoxide (DMSO), foramide, glycerol, non-ionic detergents, bovine serum albumin (BSA), polyethylene glycol, tetramethylammonium chloride, or any combination thereof; (c) one or more albumin proteins preferably BSA, HAS or any mammalian albumin; (d) the one or more chelators preferably include ethylene glycol tetraacetic acid, hydroxyethylethylenediaminetriacetic acid, diethylene triamine pentaacetic acid, N,N-bis(carboxymethyl)glycine, ethylenediaminetetraacetic, citrate anhydrous, sodium citrate, calcium citrate, ammonium citrate, ammonium bicitrate, citric acid, diammonium citrate, ferric ammonium citrate, lithium citrate, or any combination thereof; and (e) the one or more salts preferably include potassium chloride, magnesium sulfate, potassium glutamate, or any combination thereof, and the pair of primers preferably includes: (i) a first oligonucleotide primer of 18 to about 30 nucleotides in length that preferably includes at least a first sequence region that consists of a sequence that is at least 95% identical to the pathogen-specific nucleic acid sequence; and (ii) a second oligonucleotide primer of 18 to about 30 nucleotides in length that preferably includes at least a first sequence region that consists of a sequence that is at least about 90% identical, preferably at least about 95% identical to, and more preferably, at least about 98% identical the pathogen-specific nucleic acid sequence, or a complement thereof. Preferred compositions contain a non-ionic detergent, a glycerol and betaine collectively present in the composition at a concentration of about 1 mM to about 1 M.

The pathogen-specific oligonucleotide detection probe preferably is from 24 to about 35 nucleotides in length, and more preferably includes at least a first sequence region that consists of a sequence that is at least 85% identical, at least 90% identical, at least 95% identical, or at least 98% or greater identical to at least a first contiguous nucleic acid sequence from a pathogen-specific sequence, or a complement thereof. The composition may further optionally include one or more internal reference dyes compatible with a polymerase chain reaction, such as those that include one or more fluorophores, one or more quenchers, one or more reporter molecules, one or more nucleic acid intercalating agents, or any combination thereof.

In illustrative embodiments, the composition at ready-to-use concentrations preferably includes (a) about 50 mM of TRIS; (b) about 70 mM of potassium chloride; (c) about 3 mM of magnesium sulfate; (d) about 45 mM betaine; (e) about 0.03 µg/mL of bovine serum albumin; (f) about 0.1 mM of EDTA; (g) about 0.01 µM to about 1 µM of dye; (h) about 4 µM of a first oligonucleotide primer of 18 to about 30 nucleotides in length; (i) about 4 µM of a second oligonucleotide primer of 18 to about 30 nucleotides in length; (j) about 6 µM of a pathogen-specific oligonucleotide detection probe of 24 to about 35 nucleotides in length; (k) about 1 unit of Taq polymerase; and (1) about 0.2 mM of deoxynucleoside triphosphates.

The detectable label may preferably include one or more radioactive labels, one or more luminescent labels, one or more chemiluminescent labels, one or more fluorescent labels, one or more phosphorescent labels, one or more magnetic labels, one or more spin-resonance labels, one or more enzymatic labels, or any combination thereof. Exemplary detectable labels include, without limitation, fluorescein, 6-carboxyfluorescein (6-FAM), 6-carboxyfluorescein-N-succinimidyl ester (6-FAMSE), a VIC dye, or any combination thereof.

As noted herein, the invention also provides diagnostic kits that preferably include one or more of the compositions disclosed herein, and instructions for using the kit in the detection of a pathogen-specific nucleic acid segment in an aqueous sample; optionally the kit may further include (typically in a separate, distinct container), a first MTM composition that comprises: a) one or more chaotropes; b) one or more detergents; c) one or more reducing agents; d) one or more chelators; and e) one or more surfactants, each present in an amount to substantially kill or lyse one or more pathogenic or infected cells, or to denature or inactivate one or more proteins, enzymes, or nucleases liberated there from when placed in the composition for an effective amount of time. In certain embodiments, the kit may also further include (preferably within the MTM composition) a known quantity of at least a first internal positive control nucleic acid segment (and preferably one of from about 50 to about 500 nucleotides in length), wherein the internal positive control nucleic acid segment does not substantially hybridize (and preferably, does not specifically hybridize) to the genomic nucleic acids of the host from which the sample was obtained, nor to genomic nucleic acids of the one or more microbiological pathogens suspected within the sample. As noted herein, such kits may also further optionally include one or more extraction apparatuses for isolating and purifying the population of polynucleotides from the lysed/liberated/denatured sample contacted with the MTM formulation. Such an extraction apparatus may be a portable, bench-top, or even a handheld device that preferably includes: (i) a filtration vessel that has at least one receiving end and that comprises a membrane filter adapted to bind the population of polynucleotides thereto, wherein the membrane filter is disposed at least substantially across a width of the filtration vessel and at least partially therein; and (ii) a volume-dispensing mechanism adapted to controllably dispense and forcibly inject an amount of liquid operably associated with the filtration vessel to filter the liquid there through; and b) instructions for using the extraction apparatus to obtain the population of purified polynucleotides from an aqueous sample suspected of comprising at least a first pathogen.

The present invention advantageously improves conventional specimen collection, ensures lysis of any microbial pathogens contained therein, and facilitates safe and effective transport and storage of such samples from the point of collection to the point of identification and assay. Moreover, the molecular transport media compositions disclosed herein facilitate stabilization of nucleic acids liberated from the collected microorganisms, as well as maintain the fidelity and preserve the integrity of the liberated nucleic acids for extended periods of time, even under ambient, or less-than-ideal storage conditions.

Accordingly, the present invention advantageously provides a collection and preservation formulation that lyses biological pathogens, stabilizes the liberated nucleic acids (both RNAs and DNAs), and preferably at least substantially maintains, and preferably entirely maintains, the integrity of the collected polynucleotides such that at least a first portion of which is readily available, and ideally suited for downstream molecular diagnostic analysis of the nucleic acids contained within the collected specimen.

The "one-step" isolation/storage/transport formulations disclosed herein advantageously accomplish at least one or more, and preferably, all of, the following principal functions: inactivation or killing of pathogens within the sample; lysis of cells and release of nucleic acids from within the cells; inactivation of cellular enzymes, including endogenous and exogenous nucleases, to prevent degradation of the liberated nucleic acids; facilitation of facile collection and safe handling/transport of the sample of isolated polynucleotides at ambient temperatures for extended periods of time without the need for refrigeration or conventional sub-zero storage temperatures; effective stabilization of the nucleic acids during subsequent handling, transport and/or storage of the sample; and preservation and/or maintenance of the integrity of at least a first portion of the population of polynucleotides contained therein for a time sufficient to permit molecular characterization and identification of at least a first nucleic acid segment contained therein.

In particular aspects as described herein, and particularly when performing the method for the analysis of specimens that are acquired in either remote or "field" sites, the molecular transport medium (MTM) compositions of the present invention preferably stabilize the collected biological sample for at least a period of time sufficient to facilitate subsequent molecular analysis, without substantial degradation or loss of at least a first population of nucleic acids obtained from the collected sample. Preferably, the MTM compositions herein facilitate collection/transport/storage of the biological specimens collected therein for extended periods of time (from a few hours to a few days, or even a few weeks or months or more) at ambient environmental temperatures, such that the collected samples do not require refrigeration and/or freezing in order to preserve them for subsequent molecular testing. More preferably still, the MTM formulations disclosed herein stabilize and preserve the collected nucleic acids in sufficient fashion to permit subsequent amplification and identification of at least a first nucleic acid sequence from at least a first microbial pathogen present in the collected sample.

In illustrative embodiments, the MTM formulations described herein further optionally include at least a first internal positive control (IPC) to facilitate improved recovery of the microbial-specific polynucleotides, and to permit determination of sequence fidelity and preservation of the collected specimen. Exemplary known polynucleotide sequences may be present in the collection reagent at the time of specimen collection, and the subsequent analysis of this known quantity of IPC may be used to accurately monitor the fidelity of the population of polynucleotides throughout the collection/transport/analysis phases of the described identification methods.

In the practice of the invention, exemplary pathogens to be identified using the transport media disclosed herein include, but are not limited to, one or more mycobacteria, including, without limitation, one or more species or strains of the genus *Mycobacterium*, including one or more causal agents of *tuberculosis*.

The integrity of the population of polynucleotides is at least substantially maintained, and the population of polynucleotides remains substantially non-degraded, when the population of polynucleotides is stored at a temperature of about 10° C. to about 40° C. for a period of about 1 to about 30 days prior to the step of thermal cycling in the composition that includes (a)(i) about 3 M guanidine thiocyanate; (ii) about 1 mM TCEP; (iii) about 10 mM sodium citrate; (iv) about 0.5% N-lauroyl sarcosine; (v) about 0.0002% silicone polymer; (vi) about 100 mM 2-amino-2-hydroxymethyl-propane-1,3-diol (TRIS); and (vii) about 0.1 mM EDTA; or (b) (i) about 3 M guanidine thiocyanate; (ii) 1 mM TCEP; about 10 mM sodium citrate; (iii) about 0.5% N-lauroyl sarcosine, sodium salt; (iv) about 0.0002% of a silicone polymer; (v) about 100 mM TRIS; (vi) about 0.1 mM EDTA; and (vii) about 10% to about 25% ethanol (vol./vol.). In some embodiments, the integrity of the population of polynucleotides is at least substantially maintained, and the population of polynucleotides remains substantially non-degraded, when the composition containing the population of polynucleotides is stored at a temperature of from about 10° C. to about 40° C. for a period of from about 1 to about 7 days or from a period from about 7 days to about 14 days, or 14 days to about 28 days.

In particular embodiments, the integrity of the polynucleotides within the population is substantially maintained such that at least about 75%, or at least about 80%, at least about 85% or at least about 90%, at least about 95%, at least about 98% and in some instances at least about 99%, of the initial polynucleotides remain at least substantially full-length upon storage of the composition at a temperature of about 10° C. to about 40° C. for a period of about 1 to about 30 days, and, in some embodiments for a period about 1 to 14 days.

In the practice of the invention, the population of polynucleotides so analyzed will preferably be obtained from a biological sample, with biological samples obtained from a mammal (including e.g., humans, non-human primates, domesticated livestock, and the like). Samples may be obtained at any suitable time prior to the amplification protocol, and subsequent detection of amplification products, but in particular aspects, the time between sample collection, isolation of a population of polynucleotides from the sample, and the amplification/detection analysis of the target nucleic acids of interest is quite short, such as, on the order of minutes to hours from specimen collection to amplification product detection, while in other embodiments, the amplification/detection analysis of the target nucleic acids of interest may be longer.

In one embodiment, a method of collecting a biological sample suspected of containing at least a first population of polynucleotides isolated from a pathogen includes: placing the biological sample in a first collection device that contains at least a first solution comprising a) one or more chaotropes; b) one or more detergents; c) one or more reducing agents; d) one or more chelators; and e) one or more surfactants, each present in an amount sufficient to denature one or more proteins, or inactivate one or more nucleases; wherein the collection solution kills, inactivates or decontaminates any pathogens that are present in the specimen for safe handling and transport; and wherein the integrity of the population of polynucleotides is at least substantially maintained and the population of polynucleotides remains substantially non-degraded when the collection solution containing the population of polynucleotides is stored at a temperature of about 10° C. to about 40° C. for a period of about 1 to about 42 days prior to extracting the population of polynucleotides from the collection solution.

In a further embodiment, the killing, inactivation or decontamination occurs within about five minutes or less of coming into contact with the collection solution. In some embodiments, the killing, inactivation or decontamination occurs within about two minutes of coming into contact with the collection solution. In other embodiments, the killing, inactivation or decontamination occurs within about one minute of coming into contact with the collection solution.

In some embodiments, the population of polynucleotides obtained from the biological sample is further analyzed. The invention also encompasses a reagent mix for detection of a microbial sequence, the reagent mix including one or more microbe-specific primers, probes, or enzymes, or a combination thereof, present in a mixture that is at least substantially stable at ambient temperature and is adapted and configured for use with a polymerase chain reaction (PCR) device. In one embodiment, the reagent mix is substantially stable at ambient temperature for at least about 5 days and up to two weeks. In another embodiment, the detection of the microbial sequence occurs within about 90 minutes after the microbial sequence is extracted from a sample. The reagent mix can be used to identify a microbial sequence, such as a pathogen, bacterial or viral sequence, or combination thereof. The reagent mix of the present invention, also referred to herein as a "PrimeMix®," and in some instances "PrimeMix® Universal MTB," can also be used to identify strains of a viral or bacterial sequence, or even species-specific tuberculin strains.

A further embodiment can include a composition including at least one microbial-specific nucleic acid sequence or a biological sample suspected of containing at least one microbial-specific nucleic acid sequence; a solution comprising: (i) one or more buffers (each preferably present in the composition in an amount from about 1 mM to about 1M); (ii) one or more osmolarity agents or albumin proteins at least one of which comprises betaine (each preferably present in the composition in an amount from about 1 mM to about 1M); (iii) one or more chelators (each preferably present in the composition in an amount from about 0.01 mM to about 1 mM); (iv) one or more reference dyes (each preferably present in the composition in an amount from about 0.01 µM to about 50 mM, more preferably about 0.02 µM to about 1 µM); and (v) one or more salts (each preferably present in the composition in an amount from about 50 mM to about 1 M); and a first pair of pathogen-specific amplification primers. In some embodiments, the composition further includes a pathogen-specific probe. In one embodiment, the reference dye is present in an amount of about 0.01 µM to about 1 µM. Preferably the composition includes one or more salts. The salts are preferably potassium chloride, magnesium chloride, magnesium sulfate, potassium glutamate, or any combination thereof. Preferably, the concentration of salt in the composition is between about 0.5 mM and about 50 mM.

The inclusion of one or more buffers is desirable to control the pH of the formulations which stabilizes the nucleic acids and the enzymes. A preferred pH range is from about 6.0 to about 9.5, preferably between about 6.5 and about 8.0, and more preferably between bout 6.5 and about 7.5. Preferably, the pH of the buffer and/or the overall composition is within one unit of the pKa of the buffer, more preferably within about 0.5 units, more preferably within about 0.2 units and more preferably within about 0.1 units, all as measured at a selected temperature, preferably an ambient temperature. As the pH can be adjusted by the skilled individual, the more preferred buffer is one wherein the largest buffering capacity overlaps the desired pH of the composition. By way of a non-limiting example—wherein there are two buffer options for a composition at pH 7.5, and one buffer has a pKa of 7.0 and another has a pKa of 8.0, the preferred buffer is the buffer with a pKa of 8.0 for buffering hydrogen ion producing compositions and the buffer with a pKa of 7 for buffering hydrogen ion absorbing compositions. The stronger buffers have a ratio [A]/[HA] as close as possible to 1:1. It is preferred to utilize a buffer with the strongest buffering capacity and under conditions that utilize that capacity such as, for example, pH and pKa.

Exemplary buffers include, without limitation, tris(hydroxymethyl) aminomethane (Tris), citrate, 2-(N-morpholino)ethanesulfonic acid (MES), N,N-Bis(2-hydroxyethyl)-2-aminoethanesulfonic acid (BES), 1,3-bis(tris (hydroxymethyl) methylamino)propane (Bis-Tris), 4-(2-hydroxyethyl)-1-piperazineethanesulfonic acid (HEPES), 3-(N-morpholino)propanesulfonic acid (MOPS), N,N-bis(2-hydroxyethyl) glycine (Bicine), N-[tris(hydroxymethyl) methyl]glycine (Tricine), N-2-acetamido-2-iminodiacetic acid (ADA), N-(2-acetamido)-2-aminoethanesulfonic acid (ACES), piperazine-1,4-bis(2-ethanesulfonic acid) (PIPES), bicarbonate, phosphate, or any combination thereof. In a preferred embodiment, the buffer includes TRIS.

At least a first osmolarity agent can be used within the method to optimize reaction conditions, especially when a high content of guanine and cytosine are present in the sequences, and can include, without limitation, betaine, trimethylglycine, glycine betaine, dimethylsulfoxide (DMSO), foramide, deoxyinosine, glycerine, 7-deaza deoxyguanosine triphosphate, or sodium hydroxide, or any combination thereof.

Exemplary chelators include, without limitation, ethylene glycol tetraacetic acid (EGTA), hydroxyethylethylenediaminetriacetic acid (HEDTA), diethylene triamine pentaacetic acid (DTPA), N,N-bis(carboxymethyl)glycine (NTA), ethylenediaminetetraacetic (EDTA), citrate anhydrous, sodium citrate, calcium citrate, ammonium citrate, ammonium bicitrate, citric acid, diammonium citrate, potassium citrate, magnesium citrate, ferric ammonium citrate, lithium citrate, or any combination thereof. In preferred embodiments, the chelator includes EDTA, a citrate, or a combination thereof. In a more preferred embodiment, the chelator includes EDTA.

At least a first reference dye, preferably an inert chemical, can optionally be used within the method to normalize the results obtained when using fluorescent compounds, such as those used in FRET technologies. The reference dye, when included, can provide an internal reference to which the reporter dye signal can be normalized. Such a reference dye can include, without limitation, passive reference dyes such as fluorescein, 5-carboxy-X-rhodamine and commercial formulations such as ROX™, or a combination thereof. In a more preferred embodiment, the reference dye includes ROX™.

Preferably, the compositions further include the addition of deoxynucleotide triphosphates (dNTPs), such as deoxyadenosine triphosphate, deoxyguanosine triphosphate, deoxycytidine triphosphate, deoxythymidine triphosphate, or deoxyurosine triphosphate, or a combination thereof, in an amount from about 0.1 mM to about 50 mM.

The compositions of the invention can further include one or more additional compounds or reagents including, but not limited to, albumin. Albumin refers generally to any protein that is water soluble, is moderately soluble in concentrated salt solutions, and experiences heat denaturation. Albumins are commonly found in blood plasma and are unique from other blood proteins in that they are not glycosylated. Preferably the albumin is bovine serum albumin (BSA), and also preferably the composition includes magnesium sulfate, water (RNase-free and/or DNase free), and acids or bases, such as hydrochloric acid and sodium hydroxide. The acids or bases can be added to the final solution to adjust the pH. Preferably, BSA is added in a concentration of about 0.01 µg/µL to about 0.5 µg/µL.

The compositions of the invention can further include one or more polymerases. The one or more polymerases can include, but are not limited to, Taq polymerase, and high fidelity polymerases. Preferably, the one or more polymerases are present in an amount of about 1 U of enzyme to about 10 through about 50 µL of final solution.

In particular embodiments, the composition will further preferably include at least a first oligonucleotide detection probe that includes a radioactive, luminescent, chemiluminescent, fluorescent, enzymatic, magnetic, or spin-resonance label, or combination thereof. Fluorescent labels can include fluorescein (FAM), 6-carboxyfluorescein (6-FAM), or 6-carboxyfluorescein-N-succinimidyl ester (6-FAMSE), or the like, or a combination thereof. Preferred primer and/or probe concentration for each nucleic acid is between about 1 pmol and about 10 µM.

The invention further provides for a method for detecting the presence or absence of a pathogen-specific nucleic acid segment in a population of polynucleotides obtained from a biological sample, the method including: (a) performing at least one thermal cycling step, wherein the cycling comprises at least a first amplifying step and at least a first hybridizing step, wherein the at least a first amplifying step comprises contacting a population of polynucleotides obtained from a biological sample suspected of containing a pathogen-specific nucleic acid segment with a composition that comprises at least a pair of distinct, independently-selected, pathogen-specific amplification primers, a polymerase, a first osmolarity agent comprising betaine, optionally (but preferably) at least a first reference dye, and a plurality of deoxynucleoside triphosphates to produce a pathogen-specific amplification product when a pathogen-specific nucleic acid segment is present in the sample; and (b) detecting the presence of the amplification product by contacting the amplification product with a pathogen-specific oligonucleotide detection probe comprising a first detectable label, wherein the presence of a labeled hybridization product is indicative of the presence of one or more pathogen-specific nucleic acid segments in the population of polynucleotides, wherein the pair of distinct, independently-selected, pathogen-specific amplification primers comprises a first oligonucleotide primer of 18 to about 30 nucleotides in length, and a second oligonucleotide primer of 18 to about 30 nucleotides in length, wherein each of the first and second primers specifically hybridize to a first, and a second distinct sequence region, respectively, within the pathogen-specific sequence, or the complement or reverse complement thereof.

Exemplary formulations of the *Mycobacterium* Prime-Mix® of the invention are described in the examples herein, and include, without limitation, a composition that includes: (a) about 1 U of Taq Polymerase; (b) about 6 µM of the detection probe which includes a nucleic acid sequence that comprises, consists essentially of, or alternatively consists of, the nucleic acid sequence of 5'-ACCAGC-ACCTAACCGGCTGTGGGTA-3' (SEQ ID NO:4), or 5'-AGGGTTCGCCTACGTGGCCTTTGT-3' (SEQ ID NO:7); (c) about 4 µM of a reverse oligonucleotide primer of less than about 50, preferably less than about 40, and more preferably still, less than about 30 nucleotides in length that comprises, consists essentially of, or alternatively, consists of, a nucleic acid sequence that is at least 98% identical to one or more of the sequences of ACAAAGGC-CACGTAGGCGA-3' (SEQ ID NO:3), or 5'-ACCG-ACGCCTACGTCGCA-3' (SEQ ID NO:6), or the complement thereof; (d) about 4 µM of a forward oligonucleotide primer of less than about 50, preferably less than about 40, and more preferably still, less than about 30 nucleotides in length that comprises, consists essentially of, or alternatively, consists of, a nucleic acid sequence that is at least 98% identical to one or more of the sequences of 5'-CTCGTCCAGCGCCGCTTC-3' (SEQ ID NO:2), or 5'-ACCAGCACCTAACCGGCT-3' (SEQ ID NO:5), or the complement thereof; (e) about 50 mM of Tris; (f) about 70 mM of KCl; (g) about 3 mM of MgSO4; (h) about 45 mM of Betaine; (i) about 0.05 µM of ROX or comparable reference dye; (j) about 0.025 µg/µl of ultra pure BSA; (k) about 0.2 mM of dNTPs; and (l) about 0.1 mM of EDTA.

A further embodiment of the invention includes a method for detection of a microbial sequence that includes obtaining genomic nucleic acid from a biological sample and assaying the genomic material by adding the nucleic acid to the reagent mix of one or more microbe-specific primers, probes, or enzymes, or a combination thereof, wherein the mix is substantially stable at room temperature and is adapted for use with a PCR device. In another embodiment, the PCR device includes fluorescence detection equipment for real-time PCR detection.

In a further embodiment, the invention provides a method for detecting the presence or absence of a Mycobacterial-specific nucleic acid segment, and in particular aspects, provides a method for detecting the presence or absence of a particular type, subtype, or strain of *M. tuberculosis*. In exemplary embodiments, the invention provides a method of identifying Mycobacterial species and strains that contain one or more IS6110-specific nucleic acid segments in a population of polynucleotides that is preferably obtained from a biological sample.

In another aspect, the present invention provides a method for rapidly detecting in a biological sample, a particular polynucleotide sequence, such as that of the *Mycobacterium*-specific IS6110 sequence. In an overall and general sense, this method comprises amplification of a population of nucleotides suspected of containing the particular sequence using conventional methods such as PCR and forward and reverse primers that are specific for the target sequence, hybridization of a specific probe set with the resulting single-stranded PCR product, performing melting curve analysis and analyzing the $T_m$ change of the hybrid of the single-stranded PCR product with the hybridization probes.

The label on the probe can include, without limitation, radioactive, luminescent, chemiluminescent, fluorescent, enzymatic, magnetic, or spin-resonance labels known to those of ordinary skill in the molecular arts. In illustrative embodiments, the labeled probe contains at least a first minor groove binder. One such method for the detection of polynucleotides using a labeled "probe" sequence utilizes the process of fluorescence resonance energy transfer (FRET). Exemplary FRET detection methodologies often involve pairs of fluorophores comprising a donor fluorophore and acceptor fluorophore, wherein the donor fluorophore is capable of transferring resonance energy to the acceptor fluorophore. In exemplary FRET assays, the absorption spectrum of the donor fluorophore does not substantially overlap the absorption spectrum of the acceptor fluorophore. As used herein, "a donor oligonucleotide probe" refers to an oligonucleotide that is labeled with a donor fluorophore of a fluorescent resonance energy transfer pair. As used herein, "an acceptor oligonucleotide probe" refers to an oligonucleotide that is labeled with an acceptor fluorophore of a fluorescent resonance energy transfer pair. As used herein, a "FRET oligonucleotide pair" will typically comprise an "anchor" or "donor" oligonucleotide probe and an "acceptor" or "sensor" oligonucleotide probe, and such pair forms a FRET relationship when the donor oligonucleotide probe and the acceptor oligonucleotide probe are both hybridized to their complementary target nucleic acid sequences. Acceptable fluorophore pairs for use as fluorescent resonance energy transfer pairs are well known to those of ordinary skill in the art and include, but are not limited to, fluorescein/rhodamine, phycoerythrin/Cy7, fluorescein/Cy5, fluorescein/Cy5.5, fluorescein/LC Red 640, and fluorescein/LC Red 705, and the like.

In the regular practice of the method, one may also perform the cycling step on one or more "negative" and/or "positive" control sample(s) as is routinely done in the molecular genetic assay arts to ensure integrity, fidelity, and accuracy of the method. The use of such controls is routine to those of ordinary skill in the art and need not be further described herein. Likewise, in the practice of the invention, it may also be desirable to incorporate one or more known "internal positive controls" (IPCs) into the population of polynucleotides to be isolated, to further ensure the integrity, fidelity, and/or accuracy of the disclosed method.

In certain embodiments, the addition of nucleic acids (e.g., RNA and/or DNA) is contemplated to be beneficial for a variety of purposes and applications of the disclosed methods: a) as a "carrier" (The addition of small amounts of supplemental RNA/DNA has been previously been shown to augment/increase the overall yield of samples/specimens, particularly original specimens that may contain low amounts of target, i.e., cells, viruses, bacteria); b) as an IPC for downstream molecular processes and to track or monitor the fidelity of the nucleic acid preparation from sample collection to detection; and c) for comparison to a 'calibrator' for downstream quantitative analysis, e.g., qRT-PCR and the like. In such embodiments, one or more known or "control" nucleic acids could be added to the compositions in a final concentration of from about 1 ag to about 1 mg, more preferably from about 1 fg to about 1 µg, and more preferably still, from about 1 pg to about 1 ng.

In an illustrative embodiment, the invention provides an isolated single-stranded (ss) or double-stranded (ds) RNA, DNA, PNA, or hybrid thereof that is useful: (a) as a carrier molecule for aiding in the recovery of polynucleotides from a biological sample suspected of containing nucleic acids, and/or (b) as an IPC (i.e., a "known," "reporter," "control,"

"standard," or "marker") sequence to monitor the integrity and fidelity of specimen collection and polynucleotide isolation/stabilization. In certain embodiments, the invention provides an isolated ds-RNA, ds-DNA, ds-PNA, or a hybrid thereof that is useful as a carrier molecule and/or an IPC. In other embodiments, the invention provides an isolated ssRNA, ssDNA, ssPNA, or a hybrid thereof that is useful as a carrier molecule and/or as an IPC sequence. In exemplary embodiments, the invention provides an isolated ssRNA molecule that is useful as both a carrier molecule and an IPC sequence.

Such molecules can be isolated from natural sources, prepared in the laboratory, or alternatively, a hybrid containing both native- and non-native sequences. As noted herein, because the compositions of the invention are particularly useful for the isolation and characterization of biological specimens obtained from mammalian (and in particular, human) sources that are suspected of containing polynucleotides of pathogen-origin, it is preferable that the sequence(s) employed as carrier and/or positive control compounds substantially contain a primary nucleotide sequence that is not ordinarily found within the genome of a mammal, or within the genome of an organism that is pathogenic to such a mammal. Exemplary mammals include, without limitation, bovines, ovines, porcines, lupines, canines, equines, felines, ursines, murines, leonines, leporines, hircines, and non-human primates.

Preferably, this non-mammalian, non-pathogen-specific carrier/reporter sequence is not cross-reactive, i.e., does not substantially, or preferably, does not, hybridize to, mammalian or pathogen-specific sequences, and as such, non-coding, non-degenerate (i.e., nonsense) sequences are particularly preferred in the formulation of control/carrier sequences to minimize hybridization of the control/carrier sequence to a member of the isolated population of polynucleotides obtained from the collected specimen. Exemplary carrier/control sequences therefore, do not substantially, or preferably, does not, bind (e.g., hybridize under stringent hybridization conditions) to a population of polynucleotides isolated from a mammalian genome, or to a population of polynucleotides isolated from the genome of a bacterium, fungus, virus that is pathogenic to a mammal. Exemplary stringent hybridization conditions known to those of ordinary skill in the art include, without limitation, (a) pre-washing in a solution containing about 5×SSC, 0.5% SDS, and 1.0 mM EDTA (pH 8.0); (b) hybridizing at a temperature of from about 60° C. to about 70° C. in 5×SSC overnight; and (c) subsequently washing at about 65 to about 70° C. for 20 mm. with each of 2×, 0.5× and 0.2×SSC containing 0.1% SDS), or equivalent hybridization conditions thereto.

Another aspect of the invention provides for a reagent mixture incorporating the aforementioned primers and probes, and kits comprising such compositions for performance of a thermal cycling amplification method. In one embodiment, the invention provides a diagnostic nucleic acid amplification/detection kit that generally includes, in a suitable container, a pathogen-specific oligonucleotide amplification primer set as described herein, and instructions for using the primer set in a PCR amplification of a population of polynucleotides obtained from a biological sample or specimen. Such kits may further optionally include, in the same, or in distinct containers, an oligonucleotide detection probe that specifically binds to the amplification product produced from PCR amplification of a population of polynucleotides obtained from a biological sample or specimen that contains, or is suspected of containing, a pathogen-specific nucleic acid segment. Such kits may also further optionally include, in the same, or in a distinct container, any one or more of the reagents, diluents, enzymes, detectable labels (including without limitation, one or more radioactive, luminescent, chemiluminescent, fluorescent, enzymatic, magnetic, or spin-resonance labels), dNTPs, and such like that may be required to perform one or more thermal cycling amplifications of a population of polynucleotides as described herein.

Another aspect of the invention provides a kit for the collection and/or storage, and/or transport of the biological sample prior to genetic analysis of the population of polynucleotides encompassed therein. The present invention allows for a minimal collection of biological material such as sputum, i.e., about 0.01 mL to about 25 mL may be used, preferably about 0.05 mL to about 10 mL, more preferably 0.1 mL to about 5 mL. In such embodiments, a kit preferably includes one or more buffers, surfactants, chaotropes, DNase and/or RNases inhibitors, or other such nucleic acid isolation and/or purification reagents as may be required to prepare a sample for analysis, such as those described above.

In further embodiments, the kits of the invention may also optionally further include one or more extraction devices or apparatuses, as described above, to facilitate the isolation or separation of the nucleic acids from the collected biological sample. Kits of the invention may also optionally further include one or more portable, ruggedized, or field-employable thermal cycling, PCR amplification systems and/or one or more systems, devices, or instruments to facilitate detection, quantitation, and/or distribution of the detectable label(s) employed for visualization of the amplification products produced during the practice of the method.

The diagnostic reagents and kits of the present invention may be packaged for commercial distribution, and may further optionally include one or more collection, delivery, transportation, or storage devices for sample or specimen collection, handling, or processing. The container(s) for such kits may typically include at least one vial, test tube, flask, bottle, specimen cup, or other container, into which the composition(s) may be placed, and, preferably, suitably aliquotted for individual specimen collection, transport, and storage. The kit may also include a larger container, such as a case, that includes the containers noted above, along with other equipment, instructions, and the like. The kit may also optionally include one or more additional reagents, buffers, or compounds, and may also further optionally include instructions for use of the kit in the collection of a clinical, diagnostic, environmental, or forensic sample, as well as instructions for the storage and transport of such a sample once placed in one or more of the disclosed compositions.

It is contemplated that in certain embodiments, the compositions disclosed herein may be formulated such that the entire specimen collection and nucleic acid amplification/detection process may be accomplished in remote, field, battlefield, rural, or otherwise non-laboratory conditions without significantly limiting the fidelity, accuracy, or efficiency of the amplification/detection methodology. Such aspects of the invention provide particular advantages over conventional laborious isolation/collection/transport/storage/analysis protocols that require several days to several weeks to achieve, and must often be conducted under conditions that require refrigeration or freezing of the sample and/or assay reagents in order to properly complete the analysis. By providing reagent mixtures that include a mixture with all of the necessary isolation, storage, and polynucleotide stabilization components, as well as mixtures with all of the necessary reagents for amplification of selected target nucleotides (including, without limitation, the amplification primers and detection probes described herein, alone or in combination with one or more PCR buffers, diluents, reagents, polymerases, detectable labels, and such like), in a shelf-stable, ambient-temperature facile reagent mix, significant cost savings, time-reduction, and other economies of scale may be achieved using the present invention as compared to many of the conventional oligonucleotide probe-based thermal cycling assays commercially available. When a real-time PCR methodology is employed for the amplification, the detecting may optionally be performed at the end of a given number of cycles, or alternatively, after one or more of each cycling step in the amplification protocol.

The compositions and methods of the present invention are directed to the collection of a clinical or veterinary specimen or a forensic or environmental sample collection system and may include one or more collection tools and one or more reagents for efficiently: 1) obtaining a high yield of suitable specimen beyond what is currently available in the art; 2) inactivating potentially infectious biological pathogens, such as members of the *M. tuberculosis* complex, so that they are no longer viable and can be handled; shipped, or transported with minimal fear of pathogen release or contamination; or 3) effectively stabilizing and preserving lysed 'naked' RNA/DNA polymers from hydrolysis or nuclease degradation for prolonged periods at ambient temperatures until samples can be processed at a diagnostic laboratory, and preferably for achieving two or more, or all three, of these goals. The collection solutions of the present invention provide the following benefits: inactivation, killing, and/or lysis of microbes, viruses, or pathogens; destruction and/or inactivation of exogenous or endogenous nucleases, including, without limitation, RNase and/or DNase inhibitors; compatibility with a variety of conventional nucleic acid extraction, purification, and amplification systems; preservation of RNA and/or DNA integrity within the sample; facilitation of transport and shipping at ambient or tropical temperatures, even over extended periods of time, or extreme temperature variations; and suitability for short- (several hours to several days), intermediate- (several days to several weeks), or long- (several weeks to several months) term storage of the isolated nucleic acids. Suitable compositions (also referred to as "PrimeStore®") and methods can be found in commonly owned U.S. Patent Pub. No. 2009-0312285, filed Oct. 1, 2008 (the entire contents of which is specifically incorporated herein in its entirety by express reference thereto).

In exemplary embodiments, the integrity of a population of polynucleotides in the biological sample, and/or the fidelity of at least a first sequence of at least one of the polynucleotides obtained from the sample is at least substantially maintained (i.e., at least 75%, in some cases about 80%, in other embodiments at least about 85%, or even at least about 90%, at least about 95% or at least about 98% of the nucleotides within the population are substantially full-length) when the composition including the sample is stored at a temperature of from about minus 20° C. to about 40° C., or from about minus 10° C. to about 40° C., or from about 0° C. to about 40° C., or from about 10° C. to about 40° C., for a period of from about 1 to about 7 days or longer; alternatively at a temperature of from about minus 20° C. to about 40° C., or from about minus 10° C. to about 40° C., or from about 0° C. to about 40° C., or from about 10° C. to about 40° C., for a period of from about 7 to about 14 days or longer; or alternatively at a temperature of from about or from about minus 10° C. to about 40° C., or from about 0° C. to about 40° C., or from about 10° C. to about 40° C., or from about 20° C. to about 40° C. for a period of from about 14 to about 42 days or more. In addition, the integrity of the polynucleotides within a population can be substantially maintained such that at least about 80% of the initial polynucleotides remain at least substantially full-length upon storage of the composition at a temperature from about minus 20° C. to about 40° C., preferably about 10° C. to about 40° C., for a period of from about 1 to about 14 days or longer; or alternatively at a temperature of from about minus 20° C. to about 40° C., preferably about 10° C. to about 40° C., for a period of from about 14 to about 42 days or longer.

Alternatively, the integrity of a population of polynucleotides in the biological sample is at least substantially maintained such that at least about 80%, at least about 85%, at least about 90%, or at least about 95%, 96%, 97%, 98% or 99% or more of the nucleotides within the population are present in the solution when compared to the amount present in the solution when the sample was initially collected. In preferred embodiments, the integrity of the sample will be substantially maintained such that all or almost all of the bacteria-specific polynucleotides present in the initial sample will be maintained (i.e., not detectably degraded) over time.

In the practice of the disclosed methods, preferably from the time of collection to the time of isolating, purifying, or characterizing a population of polynucleotides therein, less than about 20% of the population of polynucleotides originally present in the collected sample will be degraded over time during subsequent storage. Preferably, substantially less than about 15% of the population of polynucleotides originally present in the collected sample will be degraded over time during subsequent storage, more preferably, less than about 10% of the population of polynucleotides originally present in the collected sample will be degraded over time during subsequent storage, and more preferably still, less than about 5% of the population of polynucleotides originally present in the collected sample will be degraded over time during subsequent storage. In particularly preferred embodiments, not more than about 5%, about 4%, about 3%, about 2% or about 1% of the population of polynucleotides originally present in the collected sample will be degraded over time during subsequent storage. Such high-integrity preservation of sample quality is preferable, regardless of the conditions under which the sample is stored, and will be substantially maintained for a period of time of at least about 1 day, at least about 5 days, at least about 7 days, at least about 14 days, at least about 21 days, at least about 30 days, at least about 45 days, at least about 60 days, at least about 90 days, or even at least about 120 days or more.

While the presence of, integrity of, or sequence fidelity of, a particular polynucleotide sequence obtained from, or utilized in the practice of the present invention may be determined using any conventional methodology known to those of ordinary skill in the molecular arts, in one embodiment, PCR amplification is utilized. Likewise, determination of the integrity of a polynucleotide of interest may include determination of the PCR cycle threshold (CT) under given conditions, and determination of the sequence fidelity, qualitative integrity of collected nucleic acids may be determined by conventional DNA or RNA sequencing methods, including, without limitation, the chemical-based methods of Maxam-Gilbert, the dideoxy chain termination method of Sanger et al., the dye fluorophore-based method of Mathies et al., or pyrosequencing techniques as described by Nyren and Ronaghi. For example, nucleotide sequencing may be conducted by cloning purified amplicons using a TOPO® 2.0 Cloning Kit (Invitrogen™) and then sequenced using the BigDye® Terminator v3.1 reagent kit. Unincorporated fluorescent nucleotides can be removed using a DyeEx® 96-well plate kit per manufacturer's recommendations (Qiagen®)). Nucleotide sequencing could further be performed using an ABI 3100 Genetic Analyzer (ABI Inc., Foster City, Calif., USA).

Internal Positive Control ("IPC")

In some embodiments, the collection solution and methods may further include at least one internal positive control (IPC) to monitor fidelity of the processed samples, to monitor the integrity and fidelity of specimen collection and polynucleotide isolation/stabilization and/or to monitor downstream molecular processes or analysis. Methods include placing at least one IPC nucleic acid segment into the collection solutions of the present invention or combining the IPC nucleic acid segment with the extracted population of polynucleotides to monitor downstream molecular processing of the sample and/or extracted nucleic acid. In some embodiments, the IPC is present as a component of the PrimeStore® solution and, as such is substantially stable, and substantially non-degraded when stored in the solution for extended time periods at ambient temperatures. In these instances, the IPC may be considered part of the population of polynucleotides when extracted from the collection solution.

Preferably, the IPC sequence is not cross-reactive, i.e., does not substantially, or preferably, do(es) not, hybridize to, mammalian or pathogen-specific sequences, and as such, non-coding, non-degenerate (i.e., nonsense) sequences are particularly preferred in the formulation of control/carrier sequences to minimize hybridization of the control/carrier sequence to a member of the isolated population of polynucleotides obtained from the collected specimen. Exemplary carrier/control sequences therefore, do not substantially, or preferably, do(es) not, bind (e.g., hybridize under stringent hybridization conditions) to a population of polynucleotides isolated from a mammalian genome, or to a population of polynucleotides isolated from the genome of a bacterium, fungus, protozoan, virus that is pathogenic to a mammal.

In certain embodiments, the invention provides an isolated single stranded (ss)-RNA, ssDNA, ss-PNA, double stranded (ds)-RNA, ds-DNA, ds-PNA, or a hybrid thereof, that is useful as an IPC. In preferred embodiments, where the isolation and detection of *M. tuberculosis*-complex specific nucleic acid is desired, a single stranded deoxyribonucleic acid segment is used. In illustrative embodiments, the invention provides for IPC sequences that comprise, consist essentially of, or consists of, nucleic acid sequences that are preferably at least about 80%, at least about 85%, at least about 90%, at least about 95%, at least about 96%, at least about 97%, at least about 98%, or at least about 99% or more identical to any one of SEQ ID NO:8, and SEQ ID NO:12 through SEQ ID NO:21.

Where further molecular processing of the sample or extracted nucleic acid consists of identification of *M. tuberculosis*-complex specific nucleic acids, the IPC sequences of the present invention should contain at least a first sequence domain that specifically hybridizes (i.e., binds) to a suitably-detectable probe, including, without limitation, molecularly-labeled probes and derivatives thereof. Exemplary labeled probes are those that include radioactive, luminescent, chemiluminescent, enzymatic, magnetic, or spin-resonance labels known to those of ordinary skill in the molecular arts. In preferred embodiments, the probe is labeled with 6-FAM or VIC™ dye. In illustrative embodiments, the labeled probe contains at least a first minor groove binder. In further embodiments, wherein amplification strategies such as PCR will be employed, the IPC sequences of the present invention contain at least a second sequence domain that specifically binds to a forward PCR amplification primer and a third sequence domain that specifically binds to a reverse PCR amplification primer.

Extraction of Nucleic Acids from Solutions Containing Biological Samples and the Collection Solution(s) of the Invention Following collection of the population of polynucleotides from a biological sample, any method of nucleic acid extraction or separation from the collection solution and microorganism debris, such as proteins, lipids and carbohydrates, may be performed, as would be known to one of ordinary skill in the art, including, but not limited to, the use of the standard phenol/chloroform purification, silica-based methods, and extraction methods based on magnetic glass particles. Compositions and methods used in the present invention are compatible with most, if not all, commercially available nucleic acid extraction compositions and methods, such as, but not limited to QiaAmp® DNA Mini kit (Qiagen®, Hilden, Germany), MagNA Pure 96 System (Roche Diagnostics, USA), and the NucliSENS® easyMAG® extraction system (bioMérieux, France). Generally, the extracted genomic nucleic acid is present in an amount from about 0.1 microliters to about 10,000 microliters, more preferably from about 1 microliter to about 1000 microliters, and more preferably from about 10 microliters to 100 microliters. An exemplary amount of nucleic acid is 25 microliters.

In exemplary compositions and methods of PrimeMix®, the primers and probes of the invention are added to a particular formulation so that PCR may be performed. Preferably, about 8 µM of forward and reverse primers, about 6 µM of probe and about 1 unit of Taq are present in PrimeMix®. Exemplary concentration ranges of additional components of PrimeMix® can be seen in Table 1A and PrimeStore® in Table 1B.

TABLE 1A

FORMULATION RANGES OF EXEMPLARY COMPONENTS FOR THE PREPARATION OF PRIMEMIX ® COMPOSITIONS

| Reagent | Component Final Concentration Ranges |
|---|---|
| 1. One or more buffers, e.g.: Tris, citrate, MES, BES, Bis-Tris, HEPES, MOPS, Bicine, Tricine, ADA, ACES, PIPES, bicarbonate, phosphate | about 1 mM to about 1M |
| 2. One or more polymerase chain reaction osmolarity agents, cationic functionalized zwitterionic compounds, e.g.: betaine, DMSO, foramide, glycerol, non-ionic detergents, BSA, polyethylene glycol, tetramethylammonium chloride | about 1 mM to about 1M |
| 3. One or more chelators, e.g.: EGTA, HEDTA, DTPA, NTA, EDTA, citrate anhydrous, sodium citrate, calcium citrate, ammonium citrate, ammonium bicitrate, citric acid, diammonium citrate, potassium citrate, magnesium citrate, ferric ammonium citrate, lithium citrate | about 0.01 mM to about 1 mM |
| 4. One or more dyes, e.g.: fluorescein, 5-carboxy-X-rhodamine, ROX ™ | about 0.01 mM to about 50 mM |

TABLE 1A-continued

FORMULATION RANGES OF EXEMPLARY COMPONENTS
FOR THE PREPARATION OF PRIMEMIX ® COMPOSITIONS

| Reagent | Component Final Concentration Ranges |
|---|---|
| 5. One or more salts, e.g.: potassium chloride, magnesium sulfate, potassium glutamate | about 25 mM to about 1M |
| 6. One or more polymerases, e.g.: Taq, Pfu, KOD, reverse transcriptase, Heat stable polymerase, Hot start polymerases, next gen. polymerases | about 0.05U to about 2U |
| 7. Deoxynucleoside triphosphates, e.g.: dATP, dTTP, dGTP, dCTP, dUTP | about 0.1 mM to about 1 mM |

Preferably, to this formulation a sufficient amount of primers and probe are added so as to amplify and detect the desired target.

2-amino-2-hydroxymethyl-propane-1,3-diol (TRIS) was obtained from Applied Biosystems/Ambion (Austin, Tex., USA). 2-[2-(Bis(carboxymethyl)amino)ethyl-(carboxymethyl)aminolacetic acid (EDTA) GIBCO® UltraPure BSA was obtained from Invitrogen™ Corp. (Carlsbad, Calif., USA). All other reagents are available commercially from Sigma-Aldrich or USB Corporation.

In one embodiment, a 10× buffer solution is prepared as follows:

Add 2500 μL of 2 M Tris (pH 8.0) to a sterile 5.0 mL cryovial.
Add 3500 μL of 2 M KCl to the vial.
Add 300 μL of $MgSO_4$ to the vial.
Add 900 μL of 5M Betaine to the vial.
Add 200 μL of ROX™ to the vial.
Add 50 μL of BSA to the vial.
Add 800 μL of dNTP Mix to the vial.
Add 20 μL of 0.5 M EDTA to the vial.
Add 1600 μL+130 μL of nuclease-free water (e.g., RNase-free and/or DNase free) to the vial.
Close the vial and pulse vortex to thoroughly mix the contents.
Adjust the pH of the solution to pH 8.1-8.3 using 38% HCl.
Aliquot or transfer solution to a sterile container. Store at about −20° C. until ready to use.
When used within PrimeMix®, this 10× buffer solution is diluted to about 0.5× to about 2×, preferably, about 1×.

TABLE 1B

FORMULATION RANGES OF EXEMPLARY COMPONENTS FOR THE PREPARATION
OF PRIMESTORE ™ COMPOSITIONS

| Reagent | Component Final Concentration ranges |
|---|---|
| 1. A chaotrope, e.g.: | |
| Guanidine thiocyanate | about 0.5M to about 6M |
| or Guanidine hydrochloride | about 0.5M to about 6M |
| or Guanidine isocyanate | about 0.5M to about 6M |
| 2. An anionic detergent, e.g.: | |
| N-lauroyl sarcosine (inter alia Na salt) | about 0.15% to about 1% (wt./vol.) |
| or Sodium dodecyl sulfate, | Same |
| Lithium dodecyl sulfate, | Same |
| Sodium glycocholate, | Same |
| Sodium deoxycholate, | Same |
| Sodium taurodeoxycholate, or | Same |
| Sodium cholate | about 0.1% to about 1% (wt./vol.) |
| 3. A reducing agent, e.g.: | |
| TCEP | about 0.5 mM to about 30 mM |
| or β-ME, DTT, formamide, or DMSO | about 0.05 mM to about 0.3M |
| 4. A chelator, e.g.: | |
| Sodium citrate | about 0.5 mM to about 50 mM |
| or EDTA, EGTA, HEDTA, DTPA, NTA, or APCA | about 0.01 mM to about 1 mM |
| 5. A buffer (e.g., TRIS, HEPES, MOPS, MES, Bis-Tris, etc.) | about 1 mM to about 1M |
| 6. An acid (e.g., HCl or citric acid) | q.s. to adjust to a pH of about 6 to 8, preferably 6-7 or 6.4 to 6.8 |
| 7. Nuclease-free water (RNase-free and/or DNase free) Optionally one or more of: | q.s. to desired final volume |
| 8. A surfactant/defoaming agent, e.g.: | |
| Antifoam A ® or Tween ® | about 0.0001% to about 0.3% (wt./vol.) |
| 9. An alkanol (e.g., methanol, ethanol, propanol, etc.) | about 1% to about 25% (vol./vol.) |
| 10. RNA or DNA | about 1 pg to about 1 μg/mL |

Compositions and Methods for Multiplex Analysis of Biological Samples

In some embodiments, it may be desirable to provide reagent mixtures that include more than a single pair of amplification primers and a detection probe that is specific for a given target nucleic acid sequence. For example, when it is desirable to determine the presence of two or more different types of pathogens, the composition of the invention may be formulated to contain a first pair of amplification primers that specifically bind to at least a first target region of one pathogen-specific polynucleotide, and a second pair of amplification primers that specifically bind to at least a first target region of another pathogen-specific polynucleotide.

Alternatively, when it is desirable to determine the presence of two or more different strains, the composition of the invention may be formulated to contain a first pair of amplification primers that specifically bind to at least a first target region of a particular pathogen-specific polynucleotide, and a second pair of amplification primers that specifically bind to at least a first target region of a second, distinct pathogen-specific polynucleotide.

Additionally, when it is desirable to determine the presence of one or more additional microorganisms, i.e., to identify whether a patient is co-infected, with other bacterial, or fungal, or viral infections, for example, gram-positive and gram-negative bacteria, human immunodeficiency virus, pneumoccocus, influenza, *Yesinia pestis, Pseudomonas* sp., *Stenotrophomonas maltophilia, Burkholderia cepacia, Streptococcus* sp., *Moraxella catarrhalis,* Enterobacteriaceae, *Haemophilus* sp., *Staphylococcus* sp., Rhinovirus, Respiratory syncytial virus, Coronavirus, Adenovirus, *Chlamydophila pneumoniae, Mycoplasma pneumoniae, Pneumocystis jiroveci,* and the like.

In some instances, it is desirable to test for drug resistance genes or mutations within the *M. tuberculosis* complex-specific polynucleotide. Multi-drug resistant (MDR)-TB strains could arise as a consequence of sequential accumulation of mutations conferring resistance to single agents, or by a single step process such as acquisition of an MDR element. A series of distinct mutations conferring resistance to Rifampin, INH, Streptomycin, Ethambutol, ETH, PZA, Kanamycin, and quinolones has been identified. Some of these MDR isolates arise because random mutations in genes that encode targets for the individual anti-microbial agents are selected by sub-therapeutic drug levels resulting from treatment errors, poor adherence to treatment protocols, or other factors.

In these embodiments, the composition of the invention may be formulated to contain a first pair of amplification primers that specifically bind to at least a first target region of a particular pathogen-specific polynucleotide, and a second pair of amplification primers that specifically bind to at least a first target region of a drug resistance-polynucleotide found within, for example, multi-drug resistant strains or extensively-drug resistance strains. For example, this can include resistance to rifampicin and/or isoniazid (resistance to these first-line anti-TB drugs classically defines a multidrug resistant [MDR] *tuberculosis*), as well as to one or more members of the quinolone family, or kanamycin, capreomycin or amikacin, or any combination thereof.

For detection of the particular amplification product(s) produced from such compositions, the compositions will also further include a first detection probe that specifically binds to the amplification product produced from the first pair of amplification primers, and a second distinct detection probe that specifically binds to the amplification product produced from the second pair of amplification primers. In such compositions, it is preferable that the two, three or four detection probes present in the formulation be distinct, such that each of the probes (if specifically bound to a target in the resulting amplification mixture) may be individually detectable using conventional methodologies. Such probe distinctiveness is readily achievable in the conventional arts, using, for example, detection probes that include detection moieties that fluoresce at two, three or four distinctly-different wavelengths.

In some aspects of the invention, the amplification and/or detection of target nucleic acids may be done sequentially, while in other aspects, it may be desirable to amplify and/or detection multiple target nucleic acids simultaneously. For example, a given biological sample could first be screened for the presence of *M. tuberculosis*-specific target sequence(s), and if none are found, the sample then secondarily screened for the presence of *M. bovis, M. africanum, M. microti, M. cannetti, M. caprae* and *M. pinnipedi*-specific target sequence(s).

Exemplary Definitions

In accordance with long standing patent law convention, the words "a" and "an" when used in this application, including the claims, denotes "one or more."

As used herein, the terms "about" and "approximately" are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range.

As used herein, the term "nucleic acid" includes one or more types of: polydeoxyribonucleotides (containing 2-deoxy-D-ribose), polyribonucleotides (containing D-ribose), and any other type of polynucleotide that is an N-glycoside of a purine or pyrimidine base, or modified purine or pyrimidine bases (including abasic sites). The term "nucleic acid," as used herein, also includes polymers of ribonucleosides or deoxyribonucleosides that are covalently bonded, typically by phosphodiester linkages between subunits, but in some cases by phosphorothioates, methylphosphonates, and the like. "Nucleic acids" include single- and double-stranded DNA, as well as single- and double-stranded RNA. Exemplary nucleic acids include, without limitation, gDNA; hnRNA; mRNA; rRNA, tRNA, micro RNA (miRNA), small interfering RNA (siRNA), small nucleolar RNA (snORNA), small nuclear RNA (snRNA), and small temporal RNA (stRNA), and the like, and any combination thereof.

The phrase "substantially identical," in the context of two nucleic acids refers to two or more sequences or subsequences that have at least about 90%, preferably 91%, most preferably about 92%, 93%, 94%, 95%, 96%, 97%, 98%, 98.5%, 99%, 99.1%, 99.2%, 99.3%, 99.4%, 99.5%, 99.6%, 99.7%, 99.8%, 99.9% or more nucleotide residue identity, when compared and aligned for maximum correspondence, as measured using a sequence comparison algorithm or by visual inspection. Such "substantially identical" sequences are typically considered "homologous," without reference to actual ancestry.

Microorganisms (including, without limitation, prokaryotes such as the archaebacteria and eubacteria; cyanobacteria; fungi, yeasts, molds, actinomycetes; spirochetes, and mycoplasmas); viruses (including, without limitation the Orthohepadnaviruses [including, e.g., hepatitis A, B, and C viruses], human papillomavirus, Flaviviruses [including, e.g., Dengue virus], Lyssaviruses [including, e.g., rabies virus], Morbilliviruses [including, e.g., measles virus], Simplexviruses [including, e.g., herpes simplex virus], Polyomaviruses, Rubulaviruses [including, e.g., mumps virus], Rubiviruses [including, e.g., rubella virus], Varicellovirus [including, e.g., chickenpox virus], rotavirus, coronavirus, cytomegalovirus, adenovirus, adeno-associated virus, baculovirus, parvovirus, retrovirus, vaccinia, poxvirus, and the like), algae, protozoans, protists, plants, bryophytes, and the like, and any combination of any of the foregoing.

The invention may also be used to monitor disease outbreak, progression, spread, or one or more other epidemiological statistics within, among, or between one or more global populations, including, without limitation, the spread of mycobacterial infections, the development of clinical signs of tubercular disease, and/or comorbidity with one or more additional infections such as, without limitation, wasting syndrome, Dengue fever, ebola, HIV, SARS, and one or more bacterial or viral infections, including, without limitation, pneumonias, influenzas, and the like. In certain embodiments, the samples will preferably be of mammalian origin, and more preferably of human origin.

The term "substantially free" or "essentially free," as used herein, typically means that a composition contains less than about 10 weight percent, preferably less than about 5 weight percent, and more preferably less than about 1 weight percent of a compound. In a preferred embodiment, these terms refer to less than about 0.5 weight percent, more preferably less than about 0.1 weight percent or even less than about 0.01 weight percent. The terms encompass a composition being entirely free of a compound or other stated property, as well. With respect to degradation or deterioration, the term "substantial" may also refer to the above-noted weight percentages, such that preventing substantial degradation would refer to less than about 15 weight percent, less than about 10 weight percent, preferably less than about 5 weight percent, etc., being lost to degradation. In other embodiments, these terms refer to mere percentages rather than weight percentages, such as with respect to the term "substantially non-pathogenic" where the term "substantially" refers to leaving less than about 10 percent, less than about 5 percent, etc., of the pathogenic activity.

As used herein, the term "heterologous" is defined in relation to a predetermined referenced nucleic acid sequence. For example, with respect to a structural gene sequence, a heterologous promoter is defined as a promoter that does not naturally occur adjacent to the referenced structural gene, but which is positioned by the hand of man in one or more laboratory manipulations that are routinely employed by those of ordinary skill in the molecular biological arts. Likewise, a heterologous gene or nucleic acid segment is defined as a gene or nucleic acid segment that does not naturally occur adjacent to the referenced sequence, promoter and/or enhancer element(s), etc.

As used herein, "homologous" means, when referring to polynucleotides, sequences that have the same essential nucleotide sequence, despite arising from different origins. Typically, homologous nucleic acid sequences are derived from closely related genes or organisms possessing one or more substantially similar genomic sequences. By contrast, an "analogous" polynucleotide is one that shares the same function with a polynucleotide from a different species or organism, but may have a significantly different primary nucleotide sequence that encodes one or more proteins or polypeptides that accomplish similar functions or possess similar biological activity. Analogous polynucleotides may often be derived from two or more organisms that are not closely related (e.g., either genetically or phylogenetically).

The terms "identical" or percent "identity", in the context of two or more nucleic acid or polynucleotide sequences, refer to two or more sequences or subsequences that are the same or have a specified percentage of nucleotides that are the same, when compared and aligned for maximum correspondence over a comparison window, as measured using a sequence comparison algorithm or by manual alignment and visual inspection.

As used herein, the term "substantially homologous" encompasses two or more biomolecular sequences that are significantly similar to each other at the primary nucleotide sequence level. For example, in the context of two or more nucleic acid sequences, "substantially homologous" can refer to at least about 75%, preferably at least about 80%, and more preferably at least about 85%, or at least about 90% identity, and even more preferably at least about 95%, more preferably at least about 97% identical, more preferably at least about 98% identical, more preferably at least about 99% identical, and even more preferably still, entirely identical (i.e., 100% or "invariant").

Likewise, as used herein, the term "substantially identical" encompasses two or more biomolecular sequences (and in particular polynucleotide sequences) that exhibit a high degree of identity to each other at the nucleotide level. For example, in the context of two or more nucleic acid sequences, "substantially identical" can refer to sequences that at least about 80%, and more preferably at least about 85% or at least about 90% identical to each other, and even more preferably at least about 95%, more preferably at least about 97% identical, more preferably at least about 98% identical, more preferably at least about 99% identical, and even more preferably still, entirely identical (i.e., 100% identical or "non-degenerate").

As used herein, the term "operably linked" refers to a linkage of two or more polynucleotides or two or more nucleic acid sequences in a functional relationship. A nucleic acid is "operably linked" when it is placed into a functional relationship with another nucleic acid sequence. For instance, a promoter or enhancer is operably linked to a coding sequence if it affects the transcription of the coding sequence. "Operably linked" means that the nucleic acid sequences being linked are typically contiguous, or substantially contiguous, and, where necessary to join two protein coding regions, contiguous and in reading frame. Since enhancers generally function when separated from the promoter by several kilobases and intronic sequences may be of variable lengths; however, some polynucleotide elements may be operably linked but not contiguous.

The following examples illustrate embodiments of the invention, but should not be viewed as limiting the scope of the invention.

EXAMPLES

Example 1—Collection of Biological Samples,
Nucleic Acid Extraction and Downstream
Molecular Processing In the practice of the invention, oropharyngeal, nasal, tracheal, and/or bronchial, samples of a subject suspected of having a *tuberculosis* infection are taken, typically in the form of sputum or lavage samples. This example describes the use of PrimeStore® (Longhorn Vaccines & Diagnostics, San Antonio, Tex., USA) (also described in detail in U.S. Patent Appl. Publ. No: 2009/0312285, which is specifically incorporated herein in its entirety by express reference thereto), a clinical or environmental sample collection system specifically formulated for downstream molecular diagnostic testing.

Four smear-positive sputum specimens obtained from a sputum bank (University of Pretoria, South Africa) with qualitative grading of +, ++ or +++, as observed by light microscopy, and differing viscosities were collected by having patients expectorate into a specimen cup. Typical expectorate volumes were about 5 mL to about 20 mL of sputum. The sputum samples were qualitatively observed as to whether they were bloody, purulent, foamy, frothy or salivary. Samples graded "purulent" were those observed to contain pus, while samples graded "salivary" contained larger amounts of saliva than other components such as mucous. Flocked swabs (Copan Italia S.p.A., Brescia, Italy) were then used to collect small quantities of sputum by rotating the swab five times within each sputum specimen container. Sputum specimens were weighed prior to swabbing and after each swab to estimate the volume of sputum taken. Each swab contained approximately 25 mL to 500 mL of sputum. The individual swabs were transferred to collection tubes, each containing 1.5 mL of the collection and preservation formulation of the present invention ("PrimeStore®"). The swabbing procedure was carried out in triplicate for each sputum specimen. PrimeStore® was also added to the remainder of the sputum specimen at a ratio of 1:1 as a control and then placed at −4° C. until processed. The swabs, suspended in PrimeStore® in each collection tube, were kept at room temperature for approximately twelve hours before a sample was removed for nucleic acid processing by nucleic acid extraction and real-time PCR. DNA was extracted from 100 µL aliquots of the control remaining sputum specimens and swab-tubes using the AMPLICOR® MTB Respiratory Kit (Roche) according to the manufacturer's instructions. All specimens were vortexed at maximum speed for 10 seconds to extract nucleic the acids. DNA concentrations after extraction were measured using a NanoDrop® 1000 spectrophotometer (Thermo Scientific, DE, USA), according to the manufacturer's instructions, and the calculated results are shown in Table 2. Four microliters of the extracted DNA were used for real-time PCR using the LightCycler® Mycobacterium Detection Kit (Roche Diagnostics, USA).

PrimeStore® Microbial Inactivation and Preservation of Microbial Nucleic Acid

PrimeStore® was shown to be effective for use in preparing nucleic acids from biological samples for DNA and/or DNA extraction techniques, and downstream molecular analysis. As can be seen in Table 2, the volumes collected after each swabbing ranged from about 0.05 mL to about 0.5 mL. DNA concentration after extraction ranged between about 231 and 281 ng/µL. No significant difference was obtained when comparing the DNA concentration of the control samples with the DNA concentration of the samples obtained by use of the swabs.

TABLE 2

DNA CONCENTRATION OF SPUTUM SAMPLES AFTER COLLECTION AND PRESERVATION IN PRIMESTORE ®

| Specimen | Smear Microscopy Status of Specimen | Quality | Swab Vol. 1 (mL) | Swab Vol. 2 (mL) | Swab Vol. 3 (mL) | Control Vol. (mL) | DNA Concentration (ng/µL) | | | |
|---|---|---|---|---|---|---|---|---|---|---|
| | | | | | | | Control | Swab 1 | Swab 2 | Swab 3 |
| A | + | salivary/bloody | 0.05 | 0.05 | 0.15 | 1.20 | 258.05 | 243.68 | 238.15 | 235.15 |
| B | +++ | purulent | 0.05 | 0.45 | 0.25 | 1.70 | 251.76 | 240.34 | 238.43 | 231.54 |
| C | +++ | purulent | 0.15 | 0.10 | 0.05 | 1.65 | 248.60 | 261.86 | 246.75 | 246.66 |
| D | ++ | purulent/salivary | 0.25 | 0.30 | 0.15 | 17.90 | 258.32 | 281.31 | 241.89 | 246.66 |

Real-time PCR was positive for all specimens, except one in which PCR inhibition occurred.
The results are shown in Table 3 and FIG. 1.

TABLE 3

REAL-TIME PCR RESULTS AFTER IMMERSION IN PRIMESTORE ® AND USE OF THE LIGHTCYCLER ® MYCOBACTERIUM DETECTION KIT

| Specimen | Cτ Value |
|---|---|
| Positve | 27.28 |
| Negative | — |
| A* | 31.54 |
| A-1 | 32.14 |
| A-2 | 32.75 |
| A-3 | 34.97 |
| B* | 31.56 |
| B-1 | 31.77 |
| B-2 | 32.03 |
| B-3 | 32.14 |
| C* | 23.8 |
| C-1 | 26.62 |
| C-2 | 26.56 |
| C-3 | 26.5 |
| D* | 26.64 |
| D-1 | 29.63 |
| D-2 | inhibition |
| D-3 | 28.95 |

*Remaining specimen (control) -1/-2/-3 indicates the order of swabbing.

The swabbing procedure is a useful method for collection of specimens directly from collected sputum specimen for downstream molecular processing. In this study, DNA concentrations after extractions showed similar ranges for both the swabbed and the remaining sputum specimen (control) components. A volume as low as about 50 µL of sputum diluted in 1.5 mL of PrimeStore® was sufficient for PCR analysis. However, in two of the specimens, a delay in Cτ value of ~3 logs has been noted. In case of single inhibition, this might be due to residual PrimeStore® solution being present as a result of carry-over from the DNA extraction process to the PCR.

Simple and rapid molecular diagnostic processing directly from PrimeStore® treated swabbed specimens as well as routine conventional testing was conducted from single sputum collections. Molecular processing results from small quantities of smear-positive TB specimens, obtained by swab-transfer to PrimeStore®, is feasible and accurate.

Example 2—Inactivation of Microbes in Tuberculin Samples Using PrimeStore®

To evaluate the degree of inactivation of tubercle bacteria within sputum samples when exposed to PrimeStore®, three studies were performed:

In the first study, a known MDR strain of *M. tuberculosis* was grown in MGIT® liquid based system (Mycobacteria Growth Indicator Tube, Becton Dickinson, USA). The isolate of the strain was acid-fast (AF) and smear-positive, and multi-drug resistance (MDR) was confirmed using a Line Probe Assay (HaM Lifescience GmbH, Nehren, Germany). 0.15 mL or 0.5 mL inoculum of the known MDR *tuberculosis* strain was placed into 1.5 mL of PrimeStore® for either 2 or 10 minutes' incubation. Each solution was then vortexed, and further cultured in the MGIT® liquid based system, according to manufacturer's instructions. A control sample unexposed to PrimeStore® was also placed in the MGIT® liquid culture.

The second study placed known smear-positive sputum samples (>10 acid fast *bacillus* [AFB]/high-power fields [hpf] each) into 1.5 mL of PrimeStore® for either 1 minute or 5 minutes followed by Auramine O, and Ziehl-Neelsen staining to observe cell wall morphological and integrity.

The third study used $10^5$ to $10^6$ concentration of a reference *mycobacterium* strain, namely H37rv (University of Pretoria, South Africa), to perform a time-kill assay. 0.5 mL inocula of the strain were placed in 1.5 mL of PrimeStore® for either 5 seconds, 10 seconds, 20 seconds, 40 seconds, 80 seconds, or 160 seconds, and then 2 drops of the resulting solutions were each then subcultured onto Middlebrook 7H11 agar (Becton Dickinson, Franklin Lakes, N.J., USA). Control samples unexposed to PrimeStore® were also similarly plated. In one control, 0.5 mL of H37rv strain was placed into 1.5 mL of saline. In another control, 0.5 mL of H37rv inoculum was placed directly onto the Middlebrook 7H11 agar. The plates were kept under ambient conditions for 30 minutes, then sealed, and incubated under aerobic conditions at 37° C. for six weeks. This study was performed in duplicate.

In the first study, no growth was observed in the MGIT® liquid cultures for any of the MDR tubercular samples stored in PrimeStore®, even after 42 days' incubation. The control sample unexposed to PrimeStore® showed positive growth after 9 days. Further extraction and amplification of the two samples that were stored in PrimeStore® demonstrated good banding, and confirmed the stability of the nucleic acid in PrimeStore®.

In the second study, no AFB were observed in any of the PrimeStore®-incubated samples, at either exposure times.

In the third study, no growth was observed after 42 days of incubation at any of the time points. Colony forming units were detected on the control plate after 7 days.

PrimeStore® killed a variety of *M. tuberculosis* strains within a very short period of exposure, thereby confirming PrimeStore® allows for safe and rapid point-of-care collection and transport of biological samples suspected of containing *M. tuberculosis*.

Example 3—Storage, Nucleic Acid Extraction, Molecular Processing of Tuberculin Samples and Diagnosis of *Tuberculosis*

Sputum samples were processed using the same swabbing technique as described in Example 1, as well as using 1:1 ratios of PrimeStore® to sputum. The sputum samples used in these experiments were obtained from the sputum bank as before, and had been previously classified by both smear microscopy and culture results. All samples were initially characterized for acid fastness (i.e., by either +, ++, or +++ indicators on smear microscopy), and subsequently classified as either positive, negative or scanty for *M. tuberculosis*, by culture.

DNA was extracted from the sputum sample in PrimeStore® at various time points ranging from 6 days to 6 weeks. As shown in Table 4, the specimens in PrimeStore® were kept at ambient temperature for different periods of time before nucleic acid extraction was carried out. Extraction via QiaAmp® DNA Mini kit (Qiagen®, Hilden, Germany), and the *MagNA* Pure 96™ System (Roche Diagnostics, USA), were each performed according to the manufacturers' instructions. All nucleic acid extracts were kept at −20° C. until processed for amplification.

DNA extracts were amplified by either the LightCycler® *Mycobacterium* detection kit (Roche), or using the prime mix of the present invention, hereinafter referred to as "Prime Mix Universal TB kit," "PrimeMix Universal TB kit," or simply "PrimeMix." Four microliters of extracted nucleic acid solution was used with the Prime Mix Universal TB kit. All of the above systems are real-time PCR platforms with detection of products onboard. Amplification of the Qiagen® extracts was performed in triplicate to determine the reproducibility of the LightCyler® *Mycobacterium* detection kit, and the Prime Mix Universal TB kit.

As can be seen in Table 4, four samples were smear-positive, seven samples were smear-negative and three samples were scanty.

TABLE 4

DURATION OF SPECIMEN IN PRIMESTORE ® PRIOR TO NUCLEIC ACID EXTRACTION

| | Delay before extraction (days) | |
|---|---|---|
| Extraction procedure | Smear-Negative/ Scanty | Smear-Positive |
| QiaAmp ® DNA Mini Kit (Qiagen ®) | 6 | 28 |
| MagNA Pure ™ 96 (Roche) | 20 | 42 |

TABLE 5A

SMEAR AND REAL-TIME PCR RESULTS ($C_t$ VALUES)
USING VARIOUS EXTRACTION KITS FOR SWABBED SPECIMENS

| Specimen No. | Smear | QiaAmp® Extraction/ PrimeMix® | | | QiaAmp® Extraction/ LightCycler® | | | MagNA Pure™ Extraction/ LightCycler® | MagNA Pure™ Extraction/ PrimeMix |
|---|---|---|---|---|---|---|---|---|---|
| | | 1 | 2 | 3 | 1 | 2 | 3 | | |
| 1 | + | 35.00 | X | X | – | X | X | – | 35.00 |
| 4 | ++ | X | X | X | X | X | X | 30.98 | 28.97 |
| 2 | +++ | 32.18 | X | X | 34.19 | X | X | 34.60 | 35.00 |
| 3 | +++ | X | X | X | X | X | X | 27.94 | 27.12 |
| 5 | Neg | 35.00 | 35.00 | 35.00 | 34.71 | – | – | – | 35.00 |
| 6 | Neg | – | 35.00 | – | – | – | – | – | – |
| 10 | Neg | 35.00 | 35.00 | 35.00 | 36.48 | – | 36.20 | – | 35.00 |
| 11 | Neg | 32.96 | 32.70 | 32.85 | 35.71 | 35.17 | 33.83 | 35.21 | 35.00 |
| 12 | Neg | 34.54 | 35.00 | 34.56 | 34.14 | 34.83 | 34.18 | 33.54 | 35.00 |
| 13 | Neg | – | 35.00 | – | – | – | – | – | – |
| 14 | Neg | 28.15 | 28.07 | 28.60 | 29.56 | 29.61 | 29.10 | 30.34 | 29.34 |
| 8 | scanty 1 | 32.36 | 32.28 | 32.42 | 34.46 | 34.47 | 35.31 | 34.62 | 35.00 |
| 7 | scanty 7 | 31.79 | 31.73 | 31.83 | 32.10 | 32.79 | 32.08 | 32.70 | 33.53 |
| 9 | scanty 9 | 33.15 | 33.51 | 33.43 | 36.10 | 34.53 | 34.56 | 34.27 | 35.00 |

X indicates that the experiment was not conducted;
(–) indicates that the results were negative

TABLE 5B

Summary of Analyzed Results (Number of $C_t$ Values Obtained/Number of Samples Tested)

| Smear | QiaAmp® Extraction/ PrimeMix® | | | QiaAmp® Extraction/ LightCycler® | | | MagNA Pure™ Extraction/ LightCycler® | MagNA Pure™ Extraction/ PrimeMix |
|---|---|---|---|---|---|---|---|---|
| | 1 | 2 | 3 | 1 | 2 | 3 | | |
| Smear-positive | 2/2 | X | X | 1/2 | X | X | 3/4 | 4/4 |
| Smear-negative | 5/7 | 7/7 | 5/7 | 5/7 | 3/7 | 4/7 | 3/3 | 5/7 |
| Scanty | 3/3 | 3/3 | 3/3 | 3/3 | 3/3 | 3/3 | 3/3 | 3/3 |

TABLE 6

SMEAR AND REAL-TIME PCR RESULTS (CT VALUES) USING VARIOUS EXTRACTION KITS FOR SPUTUM SAMPLES IMMERSED IN PRIMESTORE® IN A 1:1 RATIO

| Specimen No. | Smear | MagNA Pure™ Extraction/PrimeMix | MagNA Pure™ Extraction/LightCycler® |
|---|---|---|---|
| 1 | + | 35.00 | 33.02 |
| 2 | +++ | 28.96 | 33.62 |
| 3 | +++ | 23.97 | 25.53 |
| 4 | ++ | 26.30 | 28.27 |
| 5 | neg | 35.00 | 34.00 |
| 6 | neg | — | — |
| 7 | scanty 7 | 30.20 | 30.72 |
| 8 | scanty 1 | 33.59 | 32.85 |
| 9 | scanty 9 | 31.76 | 31.81 |
| 10 | neg | 35.00 | 35.19 |
| 11 | neg | 30.05 | 30.70 |
| 12 | neg | 32.68 | 32.90 |
| 13 | neg | — | — |
| 14 | neg | 26.16 | 26.74 |

(—) indicates no result(s) obtained

As can be seen in Table 5A and Table 5B, for swabbed sputum samples, DNA extracted using either the QiaAmp® DNA mini kit or the MagNA Pure™ 96 System and then processed using the PrimeMix® of the present invention detected the presence of *tuberculosis*-causing bacterial DNA when the smear sample indicated a slightly positive result (i.e., "+"), unlike that of the DNA extracted using the QiaAmp® DNA mini kit or the MagNA Pure™ 96 System and then processed using the LightCycler® *Mycobacterium* detection kit, which did not detect any *tuberculosis* (TB)-causing bacterial-specific nucleic acids. Importantly, PrimeMix® assays were able to detect *tuberculosis*-causing bacterial nucleic acids in more smear-negative, culture-positive specimens, than the LightCycler® *Mycobacterium* kit was able to detect. *Tuberculosis*-causing bacterial DNAs were equally detected using both PrimeMix® and Lightcycler® procedures, when larger amounts of sputum were analyzed.

Overall the performance of the swabbing technique and use of PrimeStore® have shown consistent results with the use of PrimeMix® in comparison to the varying results for the LightCycler® kit. PrimeStore® has shown compatibility with the different extraction systems and in no cases were inhibition of PCR a reason for a negative result.

Example 4—Compatibility of PrimeStore® with Diagnostic Assays

Fifteen smear-positive and fifteen smear-negative sputum samples (as determined by Auramine O staining), were obtained from patients suspected of having pulmonary *tuberculosis*. The smear-positive samples were tested using the Line Probe Assay, followed by culture. The smear-negative samples were also cultured. All raw sputum samples were generally then liquefied, decontaminated and concentrated using the NaLc/NaOH ("DTT/NaOH") procedure, as would be known to one of ordinary skill in the art and as described in Kubica, G. P., et al. (1963) *Sputum Digesting and Decontamination with N-acetyl-L-cysteine as a Sputum Digestant for the Isolation of Mycobacteria*, Amer. Rev. Resp. Dis.; 89:284-286 and Kubica, G. P., et al. (1963) *Sputum Digesting and Decontamination with N-acetyl-L-cysteine-sodium hydroxide for Culture of Mycobacteria*, Amer. Rev. Resp. Dis.; 87:775-779, the entire contents of which are incorporated by express reference thereto. In general, the NaLc/NaOH procedure is used prior to culture methods and nucleic acid testing for *M. tuberculosis*. Aliquots of 0.5 mL of the NaCl/NaOH treated sputum samples were then added to PrimeStore® and stored overnight. A control was also used wherein aliquots of 0.5 mL of the NaCl/NaOH treated sputum samples were not added to PrimeStore®. Extraction was performed via AMPLICOR® Respiratory Specimen Preparation Kit (Roche). Two commercial assays, the LightCycler® *Mycobacterium* Detection kit (Roche) and the Genotype MTBDRplus (HaM Lifesciences GmbH) were used to detect the presence or absence of *M. tuberculosis*-specific nucleic acids. The Genotype MTBDRplus assay was found compatible with the use of PrimeStore® contacting raw sputum samples and drug resistant TB strains were detected in these samples using this assay.

Table 7 demonstrates the results obtained with the LightCycler® *Mycobacterium* Detection kit (LC).

TABLE 7

SUITABILITY OF PRIMESTORE ® FOR MOLECULAR TESTING AFTER DECONTAMINATION

| | DTT/NaOH - No PS | | | DTT/NaOH - with PS | |
|---|---|---|---|---|---|
| | sm+ | sm− | | sm+ | sm− |
| LC pos | 13 | 0 | LC pos | 13 | 1 |
| LC neg | 2 | 15 | LC neg | 2 | 14 |
| | 15 | 15 | | 15 | 15 |

As can be seen in Table 7, after storage in PrimeStore®, the LightCycler® assay tested positive for *M. tuberculosis* in a smear negative sample, which was not obtained when PrimeStore® was not used. Thus, PrimeStore® may have a higher ability to detect lower quantities of *M. tuberculosis*. Otherwise, the results obtained were comparable, and thus PrimeStore® is compatible with commercially-available detection assays.

Example 5—Sensitivity of Detection of *M. tuberculosis* after Storage in PrimeStore®

Seven smear-negative, culture-positive specimens, and three scanty specimens (SC1, SC7 and SC9) from a sputum bank (University of Pretoria, South Africa) were included in this evaluation. Flocked swabs (Copan) were used to collect small quantities of sputum by rotating the swab within each sputum specimen (500 µL in cryovial). The individual swabs were transferred to PrimeStore® collection tubes, each containing 1.2 mL PrimeStore® solution. Sputum specimens were weighed prior to swabbing, and after each swab to estimate the volume of sputum removed from the specimen. PrimeStore® solution was also added to the remainder of the sputum specimen at a ratio of 1:1 as a control. The swabs, suspended in PrimeStore® solution in each collection tube, were kept at room temperature for approximately twelve hours before processing by real-time PCR. DNA was extracted from the remaining sputum specimen (control) and swab-tubes using the AMPLICOR® Respiratory Specimen Preparation Kit. Sputum specimens obtained from the same cultures were also processed according to conventional NaLc/NaOH procedures, and extracted using the AMPLICOR® protocol. An additional extraction method using the Invitrogen™ iPrep™ Purelink™ Virus Kit (Carlsbad, Calif., USA) from raw sputum was also evaluated from these specimens. All specimens were vortexed at maximum speed for 10 seconds and a 100-µL aliquot used for the extraction procedure. DNA concentrations after extraction were determined using the NanoDrop® 1000 instrument. Four microliters of the extracted DNA were used for real-time PCR using the LightCycler® *Mycobacterium* detection kit.

As can be seen in Table 8, the volumes collected after each swabbing ranged from about 0.05 mL to about 0.1 mL. DNA concentration after extraction ranged between about 205 to about 706 ng/µL for the swab, PrimeStore® (1:1) and NaLc/NaOH specimen. Raw sputum extracted from the Invitrogen™ iPrep™ Purelink™ Virus Kit (Carlsbad, Calif., USA) had DNA concentrations ranging from about 7.0 to about 22.6 ng/µL.

TABLE 8

SPUTUM CHARACTERIZATIONS, ESTIMATED SWAB VOLUMES AND DNA CONCENTRATIONS AFTER EXTRACTIONS

| | | | | | | DNA concentration after extraction (ng/µL) | | |
|---|---|---|---|---|---|---|---|---|
| Smear | Culture | Aliquot (500 µL) mg | Aliquot Final mg | Swab vol µL | Remaining Aliquot vol µL | Invitrogen ™ Kit for Extraction of Raw Sputum | PrimeStore ® + swab; Extraction by AMPLICOR ® | PrimeStore ® (1:1)*; Extraction by AMPLICOR ® |
| neg | pos | 300 | 295 | 50 | 450 | 16.8 | 222.9 | 213.8 | 211.7 |
| neg | pos | 305 | 300 | 50 | 450 | 22.6 | 221.6 | 284.4 | 223.4 |
| neg | pos | 305 | 295 | 100 | 400 | 9.9 | 205.7 | 706.4 | 412.7 |
| neg | pos | 305 | 300 | 50 | 450 | 10.9 | 206.9 | 231.7 | 214.9 |
| neg | pos | 310 | 305 | 50 | 450 | 20.4 | 212.9 | 277.2 | 219.3 |
| neg | pos | 250 | 240 | 100 | 400 | 7 | 255.7 | 267 | 239.4 |
| neg | pos | 260 | 250 | 100 | 400 | 9.3 | 226.6 | 276.1 | 217.1 |
| scanty 1 | pos | 300 | 295 | 50 | 450 | 12.7 | 224.9 | 273.4 | 208.7 |
| scanty 7 | pos | 260 | 245 | 50 | 450 | 13.1 | 216.2 | 243.3 | 225.7 |
| scanty 9 | pos | 295 | 290 | 50 | 450 | 6.8 | 222.7 | 233.4 | 225.6 |

Figure 2:
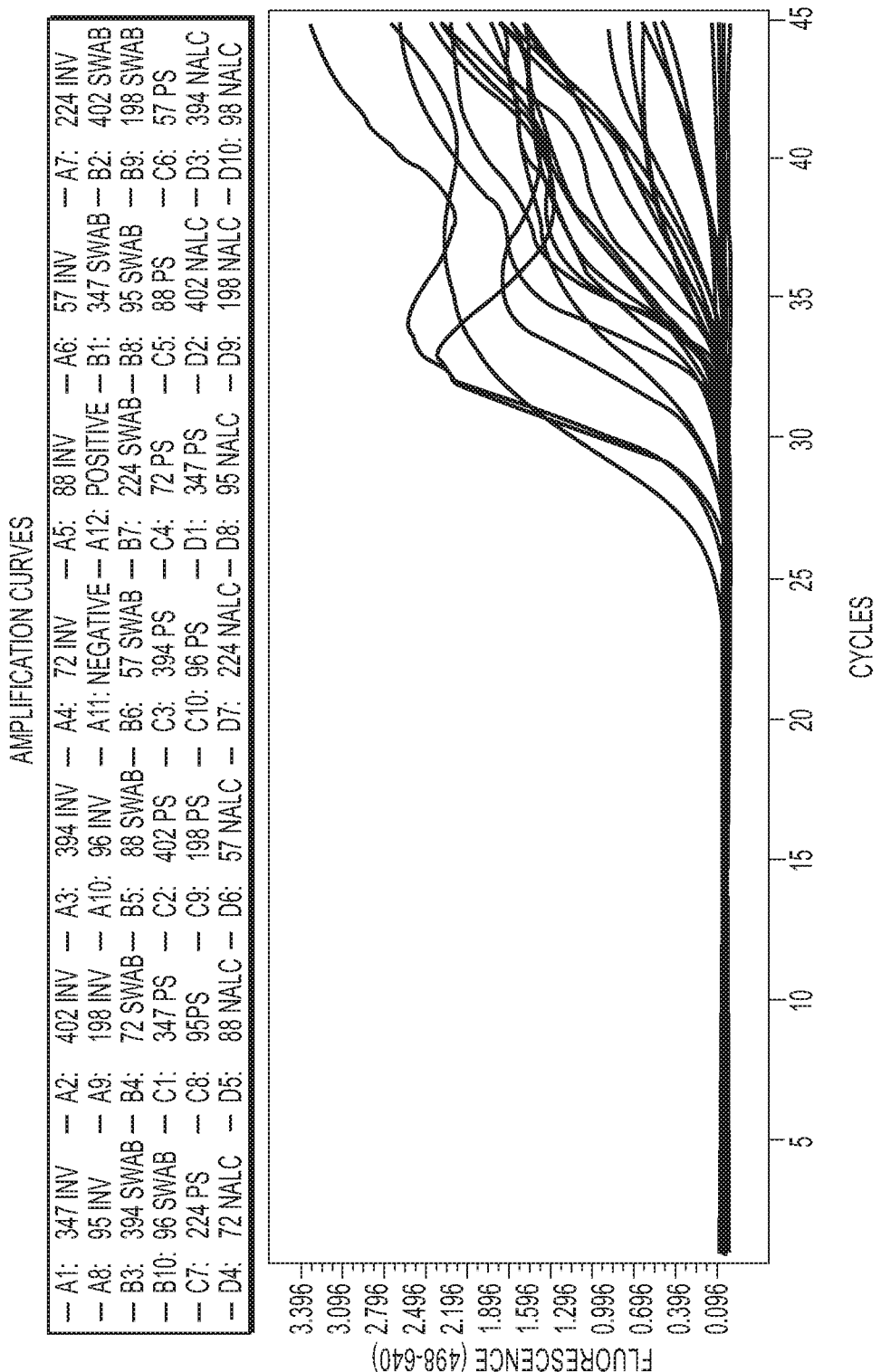
FIG. 2 illustrates the real time (RT) PCR analysis of tuberculin DNA from seven smear negative, culture positive sputum specimens and three scanty, i.e., positive smears results in which the stain was barely visible on the slide, specimen swabs preserved in PrimeStore®. DNA was extracted using the AMPLICOR® Respiratory Specimen Preparation Kit and Invitrogen™ iPrep™ Purelink™ Virus Kit (Carlsbad, Calif., USA), according to the manufacturer's instructions. The LightCycler® Mycobacterium detection kit was used, according to the manufacturer's instructions. The resulting Cτ values for each of the samples is shown in Table 8.

*1:1 is the ratio of PrimeStore to clinical sputum sample
Real-time PCR results can be seen in Table 9 and FIG. 2.

TABLE 9

REAL-TIME PCR RESULTS FOR SAMPLES USING THE LIGHTCYCLER ®
*MYCOBACTERIUM* DETECTION KIT

| Sputum Bank Number | Smear | Culture | ID | Invitrogen ™ Extraction of Raw Sputum | PrimeStore ® swab; Extraction by AMPLICOR ® | PrimeStore ® (1:1); Extraction by AMPLICOR ® | DDT/NaOH; Extraction by AMPLICOR ® |
|---|---|---|---|---|---|---|---|
| 57  | neg      | pos | MTB | 35.33 | —     | —     | —     |
| 95  | neg      | pos | MTB | 32.12 | 39.49 | 32    | 34.79 |
| 96  | neg      | pos | MTB | 27.41 | 29.26 | 37.75 | 26.24 |
| 198 | neg      | pos | MTB | —     | —     | —     | —     |
| 224 | neg      | pos | MTB | 30.77 | 33.28 | 31.87 | —     |
| 347 | neg      | pos | MTB | —     | 37.45 | 33.03 | —     |
| 402 | neg      | pos | MTB | —     | —     | —     | —     |
| 72  | scanty 1 | pos | MTB | 34.3  | —     | 32.11 | 34.25 |
| 394 | scanty 7 | pos | MTB | 31.9  | 34.09 | 29.51 | 31.59 |
| 88  | scanty 9 | pos | MTB | 31.9  | —     | 31.01 | 32.51 |

(—) symbol indicates that no results were obtained.

No amplification was seen in two of the scanty specimens, i.e., scanty 1 and scanty 9, for the swab specimens. A 100% increase in sensitivity for smear-negative, culture-positive samples was observed when using PrimeStore® in a 1:1 ratio or by swabbing in comparison to the conventional NaLc/NaOH methodology. In fact, the use of PrimeStore®, either by swabbing or in a 1:1 ratio, resulted in the detection of two additional smear-negative, culture-positive samples when compared to that of the conventional NaLc/NaOH methodology. In general, Invitrogen™'s kit is more effective than that of AMPLICOR®, therefore any variations between PrimeStore® data and that obtained by using Invitrogen™ could be explained by this discrepancy.

Example 6—PrimeStore® Formulations Containing IPCs

This example describes the use of non-specific exogenous internal positive control (IPC) polynucleotides for tracking the integrity of a specimen from the point of collection to molecular analysis using the PrimeStore® (Longhorn Vaccines & Diagnostics, San Antonio, Tex., USA) collection system.

The membrane filtration method for bacterial and fungal recovery was used to assess the killing ability of Prime-Store®. *Escherichia coli, Pseudomonas aeruginosa, Staphylococcus aureus* [non-methicillin-resistant *Staphylococcus aureus* (MRSA)], *Candida albicans, Bacillus subtilis*, and *Aspergillus brasiliensis* were used to determine whether PrimeStore® could effectively kill and inactivate a panel of bacteria and mould (yeast and filamentous fungi). Positive controls incubated in a water matrix were performed on day 0 only. A population of $1 \times 10^6$ c.f.u. for each bacterial strain was inoculated into 0.5 mL PrimeStore® for each time-point and subsequently incubated at 20-25° C. The containers were enumerated and evaluated at days 0, 1, 7, 14 and 28. The inoculum was aseptically passed through a sterile filtration device and subsequently rinsed three times with 100 mL sterile neutralizing fluid D [1 g peptic digest of animal tissue (peptone) and 1 mL polysorbate 80 dissolved in 1.0 ml of sterile (e.g., distilled, RNase-free and/or DNase free) water (final pH 7.1±0.2)]. Where necessary, dilutions of the inoculated test article were performed to deliver a target count of 25-250 c.f.u. per filter. For each time-point, inoculated negative controls were processed in a similar fashion. Filters inoculated with samples containing bacteria were plated onto tryptic soy agar (TSAP) with lecithin and polysorbate 80 and incubated at 30-35° C. for 72 hr. Filters inoculated with samples containing yeast or mould were plated onto Sabouraud dextrose agar (SAB) and incubated at 20-25° C. for no less than 72 hr but no more than 5 days. Colonies were counted to calculate $\log_{10}$ recoveries and percent (%) kill for each organism used during microbial challenge.

A stock plate containing about $10^8$ cfu MRSA (ATCC 33592) was transferred to TSB, vortexed briefly and incubated at ambient temperature for 10 min. A total of 0.1 mL bacterial suspension was transferred to 0.9 mL PrimeStore® and vortexed for 60 sec. A total of 0.1 mL suspension was transferred to 0.3 mL TSB (1:4 dilution) and 100 µL was transferred to blood agar plates (5% sheep RBCs in TSA) after 0, 5 and 15 mm. Positive controls included equivalent volumes of MRSA and TSB. Plates were allowed to dry, incubated overnight at 37° C. and analyzed for cfu/mL.

PrimeStore® was shown to rapidly inactivate microbes including fungi, Gram-positive and Gram-negative bacteria, and viruses. Antimicrobial effectiveness testing was performed using the membrane filtration technique for the quantitation of bacteria and fungi. At the first test period (24 hr), 100% of bacteria and fungi were killed compared to the positive controls. For these microbes, PrimeStore® met the inactivation criteria as described in USP Category 1 products (injections, emulsions, optic products, sterile nasal products, and ophthalmic products made with aqueous bases or vehicles). Additionally, *Bacillus subtilis* spores were challenged using the method described in USP 51 to further evaluate PrimeStore® inactivation of microbial populations. *B. subtilis* spores were reduced by 99% within 24 hr of exposure. In a time-kill study of MRSA inoculated into PrimeStore®, viable bacteria were not detected (100% killing) at the earliest study time (5 mm post-inoculation) or at any of the later evaluation times. Data also demonstrated that PrimeStore® rapidly kills *M. tuberculosis* from clinical sputum samples.

In illustrative embodiments, a unique IPC ssRNA has been described that can be added in advance (e.g., about $3 \times 10^5$ target copies/0.5 mL) to PrimeStore®, and used as an internal control to verify sample stability from the time of sample collection through extraction and detection. Additionally, the IPC ssRNA is useful as a carrier species (particularly for samples containing very low levels of target nucleic acids), and serves as a control for monitoring the integrity, efficiency, and fidelity of the nucleic acid extraction process from the point of collection to nucleic acid analysis. Exemplary IPCs suitable for formulation in PrimeStore® include, without limitation, exogenous and/or synthetically-produced (in vitro) ssDNAs or ssRNAs, and preferably include those polymers that are non-homologous (e.g., as determined by BLAST computer-based analyses) to polynucleotide sequences founds in the mammalian host or the one or more pathogens or normal bacterial flora contained therein.

PrimeStore® has been shown to facilitate standard sequencing and meta-genomic analysis of original clinical samples by improving the quality of target microbial nucleic acids in the originally-collected specimens, even when they arrive at the analytical laboratory hours, or even days later, including those stored and/or transported under less-than-ideal, or even ambient environmental conditions. Recovery of RT-PCR amplification fragments over 1400 bases has been observed from viral RNA preserved and shipped in PrimeStore® at ambient temperature for several weeks. In harsh conditions, i.e., 38° C. incubation, RT-PCR amplification of 574-bp and 825-bp fragments were observed from PrimeStore® preserved virus where no amplification was observed from stock virus in commercial V™.

Importantly, PrimeStore® has been demonstrated to be compatible with many commercial nucleic acid extraction kits. Nucleic acids are extracted directly from PrimeStore® according to standard manufacturer's protocol with only minor differences noted in $C_\tau$ values between column- or bead-based kits. Moreover, PrimeStore® received FDA-Emergency Use Authorization as part of the complete Longhorn Influenza A/H1N1-09 Prime RRT-PCR Assay™. PrimeStore® is the first molecular transport medium to receive EUA FDA approval, and the first to contain an IPC to control for monitoring specimen degradation from collection to detection.

Example 7—PrimeStore® for Extended Preservation of Microbial Samples and RNA Isolates This example demonstrates the usefulness in PrimeStore® formulations to inactivate pathogenic organisms, yet retain long-term storage and retention of RNA isolated from such inactivated organisms. As an exemplary embodiment, PrimeStore® was used to collect biological samples containing A/Vietnam/1203/2004 (H5N1) influenza virus. Results demonstrated that the formulation not only inactivated H5N1 and A/Mexico/4108/09 (H1N1, clinical isolate) virus in collected samples, but also preserved the microbial RNA for subsequent PCR analysis. The study demonstrated the lack of cytopathic effects (CPE) or CPE-like reactions of PrimeStore® reagent (1:100 dilution) to Madin-Darby canine kidney cell monolayers, the efficacy of PrimeStore® to inactivate viable H5N1 virus ($1.26 \times 10^7$ TCID$_{50}$), and the ability of PrimeStore® to preserve viral RNA from H5N1 and H1N1 for up to 62 days in ambient conditions for real-time PCR analysis that resulted in the detection of an abundance of RNA product.

Part 1 of the study comprised of two sections: (1) In vitro toxicity assessment of PrimeStore® reagent on Madin-Darby canine kidney (MDCK) epithelial cells and (2) efficacy of inactivation testing of PrimeStore® reagent against H5N1. Part 2 of the study assessed the quality of the H5N1 and H1N1 RNA that had been impacted as a direct result of the influenza virus long-term storage in PrimeStore®.

The in vitro toxicity assessment of Part 1 was performed by loading sample collection swabs in triplicate with 0.1-mL viral storage buffer (complete cell culture medium or Minimal Essential Media+10% fetal bovine serum), placed into 5-mL tubes that contained 1.5 mL PrimeStore® and incubated at room temperature (ambient) for 10, 30, or 60 minutes. Following incubation, the swabs were processed using two methods: (1) An aliquot from the viral storage buffer+PrimeStore® sample was removed and serially diluted (10-fold) to $10^{40}$ in complete cell culture media in a 96-well plate that contained a monolayer of MDCK cells. The cells were allowed to incubate for up to 96 hours and then visually examined for the presence of cytopathic effects (CPE) and the dilution that exhibited no observable CPE determined. (2) Each of the viral storage buffer-loaded swabs were removed from PrimeStore® and placed in a 50-mL conical tube that contained 10 mL complete cell culture medium. The swabs were agitated at 200 rpm for 15 min, and an aliquot of each extract was removed and serially diluted (10-fold) in complete cell culture media in a 96-well plate that contained a monolayer of MDCK cells. The cells were allowed to incubate for up to 96 hours and then visually examined for the presence of CPE and the dilution that exhibited no observable CPE determined.

Efficacy of inactivation of Part 1 was conducted based on the results from the in vitro toxicity assessment. Sample collection swabs (n=6) were loaded with 0.1 mL H5N1 ($1-5 \times 10^7$ TCID$_{50}$/mL) or viral storage buffer (negative controls, n=3), placed into 5-mL tubes that contained 1.5 mL PrimeStore® and incubated in ambient conditions for 10, 30, or 60 min Following incubation, the swabs were processed using the most appropriate approach determined from the in vitro toxicity testing. The cells were allowed to incubate for up to 96 hours and then visually examined for the presence of cytopathic effects (CPE) and total TCID$_{50}$ determined. Inactivation efficacy was calculated in terms of a log reduction compared to the untreated controls.

The extended ambient storage study for Part 2 involved the preservation of H5N1 and H1N1 RNA in PrimeStore® for up to 62 days at room temperature. The time-points were at Day 0 (day of H$_5$N$_1$ inoculation into the PrimeStore®), +1, +2, +5, +7, +14, +30, and +62 days from the date of inoculation. The H5N1 and H1N1 viruses were diluted to $1 \times 10^5$ TCID$_{50}$ prior to inoculation into PrimeStore®. At each time-point, RNA isolations using the RNAqueous-Micro Kit (Ambion Cat. No. AM1931, Austin, Tex., USA) were performed on both H5N1 and H1N1 samples stored in PrimeStore®. The resulting RNA were stored at <–80° C. until all of the time-points' RNA were isolated. Real-time PCR was performed on an Applied Biosystems (Forster City, Calif., USA) 7900HT (Fast Real-Time PCR System).

The first method used in the in vitro toxicity assessment of Part 1 (an aliquot from the viral storage buffer+PrimeStore® sample was removed and serially diluted then added to a 96-well plate) resulted in the observation of CPE or CPE-like reaction in the IVIDCK cell monolayer at 1:10,000 for all time-points (10, 30, and 60 min). The second method used in the in vitro toxicity assessment of Part 1 (each of the viral storage buffer-loaded swabs were removed from PrimeStore® and placed in a 50-mL conical tube that contained 10 mL complete cell culture medium, the swabs were agitated for 15 min, and an aliquot of each extract was removed and serially diluted) resulted in the observation of CPE or CPE-like reaction in the MDCK cell monolayer at 1:100 for all time-points. Therefore, the in vitro toxicity assessment of Part 1 determined that the second method of sample extraction resulted in CPE or CPE-like reaction to the MDCK cells by PrimeStore®, and this second method was deemed suitable for efficacy of inactivation testing of Part 1. The 60-min time point (i.e., the longest time point recorded) was chosen for the efficacy test since it did not determine whether CPE or CPE-like reactions corresponded with any time-point. The CPE or CPE-like reactions for the longest time-point were equivalent to the shortest time-point (10 min), this clearly demonstrated that CPE or CPE-like reactions were dilution (1:100)- and extraction method (second method)-dependent.

The efficacy of inactivation testing of Part 1 resulted in no detectable, viable $H_5N_1$ since the virus recovery was equivalent to the negative control (i.e., PrimeStore® with no virus added). Whereas, the positive control (i.e., no PrimeStore® added, cell culture media used in lieu of PrimeStore® reagent, virus added) resulted in excellent recovery (67.59% average recovery) of H5N1 as expected. The results indicate that PrimeStore® reagent was capable of inactivating a high titer of H5N1 ($1.26\times10^7$ $TCID_{50}$) at 60 min down to the level of the negative control.

The real-time PCR from the extended ambient storage study for Part 2 showed that target detection to all four assays (BBRC H1N1, BBRC H5N1, Longhorn H1N1, and Longhorn H5N1) from the RNA extracted from the longest time-point at 62 days proved to be just as sensitive (all average $C_\tau<26.00$) as the shortest time-point at Day 0 (day of inoculation). The results indicate that PrimeStore® reagent did not have deleterious effects on the RNA during extended storage durations in ambient conditions.

Example 8—Analysis of Specimens Containing Mycobacterial-Specific Nucleic Acids

Universal species-specific assays target a highly conserved region of the IS6110 gene, an insertion element found almost exclusively within the members of the *Mycobacterium tuberculosis* complex. Multiple copies of the IS6110 element can be found at differing locations in the genomes of the members of the *M. tuberculosis* complex, so these primers can also aid in genotyping strains. All primers and probes were procured from Applied Biosystems (Foster City, Calif., USA).

The laboratory-based LightCycler® 2.0 instrument (Roche Molecular Diagnostics, Indianapolis, Ind., USA), and its lightweight portable (50-lb) version, the Ruggedized Advanced Pathogen Identification Device (R.A.P.I.D., Idaho Technologies, Salt Lake City, Utah, USA), are both 32-well capillary, real-time instruments which employ similar components and operational software. The R.A.P.I.D. is configured within a hardened case, and can be employed remotely (e.g., in the field, or at the point-of-care).

Primer and probe sequences are shown above. Primer pair melting points are within 2° C. and anneal/extend at 58-60° C. The respective probes anneal/extend 8-10° C. higher than that of the primers. Thermocycling operates in a rapid, 2-temperature format with annealing and extension, each at 60° C. for at least about 30 seconds total, facilitated by the short nature of the respective amplicons.

Real-time amplification was performed in a single-step, single-reaction-vessel format. Using the PrimeMix® Universal MTB Assay (Longhorn Vaccines & Diagnostics, USA), either 2 µL, 3 µL, 4 µL or 5 µL of nucleic acids was added to either 18 µL, 17 µL, 16 µL or 15 µL, respectively, of master mix (i.e., PrimeMix®) containing the following components at the indicated final concentrations: (a) 1× reaction buffer containing 50 mM of Tris, pH8.0, 70 mM of KCl, 3 mM of $MgSO_4$, 45 mM of Betaine, 0.05 µM of ROX™, 0.025 µg/µL of ultra pure BSA, 0.2 mM of dNTPs, and 0.1 mM of EDTA; (b) 1× enzyme mixture containing 20 µM of each primer, 1 unit of Taq polymerase, and 20 µM labeled probe. The forward primer for amplifying the *M. tuberculosis* target sequence consisted of the following sequence: 5'-CTCGTCCAGCGCCGCTTC-3' (SEQ ID NO:2). The reverse primer for amplifying the *M. tuberculosis* target sequence consisted of the following sequence: 5'-ACAAAGGCCACGTAGGCGA-3' (SEQ ID NO:3). The labeled probe for detecting the presence of the *M. tuberculosis* target sequence consisted of the following sequence: 5'-6FAM-ACCAGCACCTAACCGGCTGTGGGTA-MGBNFQ-3' (SEQ ID NO:4). FIG. 5 shows that the addition of more template *M. tuberculosis* DNA, i.e., 5 µL rather than 2 µL of extracted patient DNA, results in slightly better RT-PCR amplification and detection results, i.e., an average Cτ value of 25.1 for 2 µL versus an average Cτ value of 23.4 for 5 µL.

Thermocycling was performed as follows: an initial hot-start at 95° C. for 5 min, followed with 40 cycles of denaturation at 95° C. for 10 sec, and a combined annealing and extension at 60° C. for 32 sec. Amplification efficiency was determined using the Cτ slope method according to the equation: $E=[10^{(-1/Slope)}-1]\times100$. All assays described here exhibited greater than 98.5% amplification efficiency.

For each analysis, 'no template' and 'positive' controls were included. Baseline fluorescence for each analysis was manually adjusted to that of the respective 'no template' control reaction. The 'positive' control gives rise to an increase in fluorescence intensity relative to the no template baseline. A 'positive' unknown is defined as amplification exceeding baseline fluorescence with a corresponding Cτ value not exceeding 36 in a 40-cycle run.

Samples were collected by swirling a Copan swab five times around a sputum specimen and immersed in a PrimeStore® collection tube containing 1.5 mL of PrimeStore® solution. A 1:1 ratio of sample to PrimeStore® was also used, as described above. Prior to this evaluation the swabbed material was extracted using the AMPLICOR® Respiratory Specimen Preparation Kit and amplified using the LightCycler® *Mycobacterium* Detection Kit. The specimens were kept at ambient temperatures for approximately 6-30 days prior to nucleic acid extraction and amplification using the PrimeMix™ Universal MTB Assay as described above. The PrimeMix™ Universal MTB Assay was shipped to the lab from the United States at 4° C. (4 days) and once received remained at ambient temperature for 48 hours before being stored at minus 20° C.

Nucleic acid extraction was carried out using the QIAamp® DNA Mini Kit (Qiagen®, Hilden, Germany) according to manufactures' instructions. 200 µl of the swabbed material in PrimeStore® was vortexed briefly (e.g., 5 to 10 sec) and used as starting material for the extraction procedure.

Nucleic acid amplification was carried out using the PrimeMix™ Universal MTB Assay. The forward primer for amplifying the *M. tuberculosis* target sequence consisted of the following sequence: 5'-CTCGTCCAGCGCCGCTTC-3' (SEQ ID NO:2). The reverse primer for amplifying the *M. tuberculosis* target sequence consisted of the following sequence: 5'-ACAAAGGCCACGTAGGCGA-3' (SEQ ID NO:3). The labeled probe for detecting the presence of the *M. tuberculosis* target sequence consisted of the following sequence: 5'-6FAM-ACCAGCACCTAACCGGCTGTG-GGTA-MGBNFQ-3' (SEQ ID NO:4). The PCR reaction contained 18 μl of PrimeMix™ Universal MTB and 2 μL of extracted nucleic acids. The amplification profile consisted of an initial hot-start at 95° C. for 5 mm, followed with 40 cycles of denaturation at 95° C. for 10 sec and a combined annealing and extension at 60° C. for 32 sec, as described above. Amplification was carried out on the LightCycler® 480 platform (Roche) and the amplicon was detected due to FAM labeling of the probe.

Similar to the Examples described above, comparative studies were performed using the following protocols: (1) NaLc/NaOH decontamination procedure followed by extraction by use of the AMPLICOR® Respiratory Specimen Preparation Kit and amplification using the LightCycler® *Mycobacterium* Detection (MTB) kit; (2) the swabbing procedure of the culture into PrimeStore®, followed by extraction by use of the AMPLICOR® Respiratory Specimen Preparation Kit and amplification using the LightCycler® MTB kit; (3) a 1:1 ratio of specimen to PrimeStore®, followed by extraction by use of the AMPLICOR® Respiratory Specimen Preparation Kit and amplification using the LightCycler® MTB kit; (4) the swabbing procedure of the culture into PrimeStore®, followed by extraction by use of the AMPLICOR® Respiratory Specimen Preparation Kit and amplification using the PrimeMix® Universal MTB Assay; and (5) the swabbing procedure of the culture into PrimeStore®, followed by extraction by use of the QIAamp® DNA Mini Kit and amplification using the LightCycler® MTB kit.

Results of the PrimeMix® Universal MTB Assay can be seen in Tables 10 and 11.

TABLE 10

SPECIMEN INFORMATION

| Specimen No. | Smear | Culture ID | Volume of specimen on swab (μL) | Duration (days) of swab sample in PrimeStore® at ambient temp prior to amplification |
|---|---|---|---|---|
| 1 | + | *M. tuberculosis* | 50 | 28 |
| 2 | +++ | *M. tuberculosis* | 50 | 28 |
| 3 | +++ | *M. tuberculosis* | 150 | 28 |
| 4 | ++ | *M. tuberculosis* | 250 | 28 |
| 5 | Negative | *M. tuberculosis* | 100 | 6 |
| 6 | Negative | *M. tuberculosis* | 100 | 6 |
| 7 | Scanty 7 | *M. tuberculosis* | 50 | 6 |
| 8 | Scanty 1 | *M. tuberculosis* | 50 | 6 |
| 9 | Scanty 9 | *M. tuberculosis* | 50 | 6 |
| 10 | Negative | *M. tuberculosis* | 50 | 6 |
| 11 | Negative | *M. tuberculosis* | 50 | 6 |
| 12 | Negative | *M. tuberculosis* | 50 | 6 |
| 13 | Negative | *M. tuberculosis* | 50 | 6 |
| 14 | Negative | *M. tuberculosis* | 100 | 6 |

TABLE 11

COMPARISON OF PCR RESULTS USING DIFFERENT PROCESSING METHODS

| Specimen No. | Smear | NaLc/NaOH; LightCycler® MTB Kit $C_\tau$ Value | Swab in PrimeStore®; LightCycler® MTB Kit $C_\tau$ Value | Specimen to PrimeStore® (1:1); LightCycler® MTB Kit $C_\tau$ Value | Swab in PrimeStore®; PrimeMix® Universal MTB Assay $C_\tau$ Value | Swab in PrimeStore®; Qiagen®; LightCycler® Mtb Kit $C_\tau$ Value |
|---|---|---|---|---|---|---|
| 1 | + | 27.00 | 31.34 | 31.54 | 35.00 | 31.67 |
| 2 | +++ | 28.82 | 31.77 | 31.56 | 33.43 | 32.74 |
| 3 | +++ | 29.21 | 26.62 | 23.80 | 26.24 | 26.56 |
| 4 | ++ | 28.04 | 29.63 | 26.64 | 27.51 | 28.96 |
| 5 | neg | — | 37.45 | 33.03 | 35.00 | 33.11 |
| 6 | neg | — | — | — | — | — |
| 7 | scanty 7 | 34.25 | 34.09 | 29.51 | 33.03 | 31.85 |
| 8 | scanty 1 | 31.59 | — | 32.11 | 35.00 | 34.21 |
| 9 | scanty 9 | 32.51 | — | 31.01 | 35.00 | 33.75 |
| 10 | neg | — | — | — | 35.00 | 33.89 |
| 11 | neg | — | 33.28 | 31.87 | 35.00 | 33.59 |
| 12 | neg | 34.79 | 39.49 | 32.00 | 35.00 | 32.72 |
| 13 | neg | — | — | — | — | 34.47 |
| 14 | neg | 26.24 | 29.26 | 37.75 | 35.00 | 29.19 |

(—) symbol indicates that no results were obtained.

The PrimeMix™ Universal MTB Assay detected 71% of the smear negative cases as well as a 100% of the smear positive ones. The PrimeMix™ Universal MTB Assay detected a higher number of culture positive samples than use of the LightCycler® MTB. The PrimeMix™ Universal MTB Assay was compatible with the use of the PrimeStore® solution.

Example 9—Stability of the PrimeMix® Universal MTB Assay

PrimeMix® Universal MTB Assay components as described above were removed from storage in minus 20° C. temperature and placed at room temperature a varying number of times, i.e., one, three, five and ten times, to determine the stability of the combined reagents and whether repeated thawing and freezing would inhibit the performance of the PrimeMix® Universal MTB Assay in detecting *M. tuberculosis* complex in nucleic acid samples. All of the assay components in a single tube and were thawed at room temperature for about three to about five minutes. The tube was then placed in minus 20° C. temperature for about one hour to start the next freeze-thaw cycle. After the final freeze-thaw cycle, RT-PCR was carried out as described above for the PrimeMix® Universal MTB Assay using a previously-identified MDR-TB strain (University of Pretoria, South Africa). Experiments were carried out in triplicate for each number of freeze-thaw cycles and the resulting $C_\tau$ values were averaged.

Figure 3:
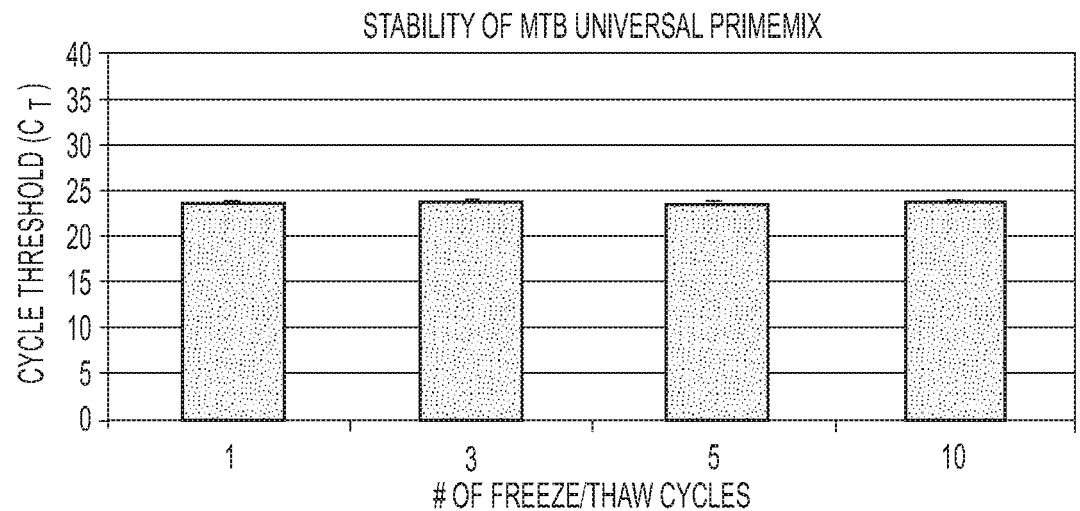
FIG. 3 shows a graph of the RT-PCR analysis of PrimeMix® Universal MTB Assay components that were removed from storage in −20° C. temperature and placed at room temperature a varying number of times, i.e., one, three, five and ten times and then used in the PrimeMix® Universal MTB Assay.

Results of the PrimeMix® Universal MTB Assay after being placed in a number of freeze/thaw cycles can be seen in FIG. 3. As can be seen from this graph, the PrimeMix® Universal MTB Assay showed no reduction in PCR amplification, as indicated by the resulting $C_\tau$ values, which do not vary significantly from one another, even when the PrimeMix® Universal MTB Assay components are thawed and re-frozen ten times. The average Cτ values after one freeze-thaw cycle ($C_\tau$=23.6) and after ten freeze-thaw cycles ($C_\tau$=23.7) did not vary significantly. Thus, the PrimeMix® Universal MTB Assay contains stable components which do not degrade under varying temperature conditions making it particularly suitable for use in the field, away from traditional laboratory settings.

Example 10—Detection of IPC(s) to Monitor Sample Integrity/Nucleic Acid Fidelity in PrimeMix Assays Design of Internal Positive Control to be Placed into PrimeStore®, Along with Primers and Probes to Detect the Same As noted herein, in certain embodiments it is desirable to include a nucleic acid carrier molecule and/or an IPC sequence to aid in preparation, stabilization, and quantitation of the isolated polynucleotides. The IPCs of the invention may be directly chemically synthesized using conventional methods, or alternatively, prepared using recombinant DNA technology. It is desirable to formulate an IPC sequence that is both non-genomic, and that does not significantly hybridize to a mammalian genome, or to the genome of pathogenic species of interest. Particular compositions and methods of use can be found in Applicant's co-pending U.S. Patent Appl. Publ. No. 2009/0233309 (filed Apr. 20, 2009), the contents of which is specifically incorporated herein by reference in its entirety.

In one embodiment, the inventors have employed a single-stranded DNA molecule comprising the sequence of SEQ ID NO: 8 (5'-GGGATCGTATAATCGTCGTGC-AGTCAGTCCCTCGGTTAAAGTCTCGAGTCGCTCTG-T CAAAATATCCGTACCGTAGTCGATGCGAGCGA- G-TCCGATCAGTCCAGGTTTCAAAGT CAAATGACTA-3') as an internal positive control to monitor the fidelity and integrity of the nucleic acids being assayed. Typically, about 0.02 pg/mL of single stranded DNA target was placed into PrimeStore®. In exemplary embodiments, the selected amplification primers and labeled oligonucleotide detection probes preferably each bind to at least a first isolated nucleotide sequence of SEQ ID NO:8. Using the following specific amplification primers, the resulting amplification product is about 100-bp in length:

(SEQ ID NO: 9)
Forward primer: 5'-GTGCAGTCAGTCCCTCGGTTA-3'

(SEQ ID NO: 10)
Reverse primer: 5'-TTGACTTTGAAACCTGGACTGATC-3'

As an illustrative oligonucleotide detection probe specific for this amplification product, the inventors selected the sequence of SEQ ID NO:11 (5'[FAM]-AAATA-TCCGTACCGTAGTCG-[MGB]-3').

IPCs useful in the practice of the present invention need not include one of the illustrative sequences described herein, nor do the IPCs even need be substantially homologous to any of the IPC sequences enclosed herein. To illustrate this point, the following sequences represent variants of SEQ ID NO:8 that are also functional as carrier DNA/IPC sequences, despite having sequence degeneracy:

The IPCs of the present invention need not be prepared from the precise illustrative DNA amplicon disclosed herein as SEQ ID NO: 8. Additional examples of DNA sequences useful in the in vitro preparation of suitable carrier RNA molecules include, without limitation, one or more of the following sequences. In each instance, the polymerase transcription site is shown in single underline, while the sequences of exemplary forward and reverse PCR primer binding domains are shown in double underline. Exemplary sequence domains to which suitable labeled molecular probes are bound are shown in bold.

(SEQ ID NO: 12)
5'-X$_n$TATTAATACGACTCACTATAGGGX$_n$GTGCAGTCAGTCCCTCGGTT

AAAGTCTCGAGTCGCTCTGTCAAAATATCCGTACCGTAGTCGATGCGAGC

GAGTCCGATCAGTCCAGGTTTCAAAGTCAAX$_n$-3', wherin X is any nucleotide and $_n$ is any integer from 0 to about 500.

(SEQ ID NO: 13)
5'-ATCGTATTAATACGACTCACTATAGGGAATCGTCGTGCAGTCAGTCC

CTCGGTTAAAGTCTCGAGTCGCTCTGTCAAAATATCCGTACCGTAGTCGA

TGCGAGCGAGTCCGATCAGTCCAGGTTTCAAAGTCAAATGACTA-3'.

(SEQ ID NO: 14)
5'-ATCGTATTAATACGACTCACTATAGGGAATCGTCGTGCAGTCAGTCC

CTCGGTTAAAGTCTCGAGTCGCTCTGTCAAAATATCCGTACCGTAGTCGA

TGCGAGCGAGTCCGATCAGTCCAGGTTTCAAAGTCAAATGACTA-3'.

(SEQ ID NO: 15)
5'-ATCGTATTAATACGACTCACTATAGGGAATCGTCGTGCAGTCAGTCC

CTCGGTTAAAGTCTCGAGTCGCTCTGTCAAAATATCCGTACCGTAGTCGA

TGCGAGTCCGATCAGTCCAGGTTTCAAAGTCAAATGACTA-3'.

-continued (SEQ ID NO: 16)
5'-ATATTAATACGACTCACTATAGGGAGTGCAGTCAGTCCCTCGGTTAA

AGTCTGAGTCGCTCTGTCAAAATATCCGTACCGTAGTCGATGCGAGCGAG

TCCGATCAGTCCAGGTTTCAAAGTCAAAT-3'.

(SEQ ID NO: 17)
5'-ATATTAATACGACTCACTATAGGGAGTGCAGTCAGTCCCTCGGTTAA

AGTCTGAGTCGCTCTGTCAAAATATCCGTACCGTAGTCGATGCGAGCGA

GTCCGATCAGTCCAGGTTTCAAAGTCAAAT-3'.

(SEQ ID NO: 18)
5'-ATATTAATACGACTCACTATAGGGAGTGCAGTCAGTCCCTCGGTTAA

AGTCTGAGTCGCTCTGTCAAAATATCCGTACCGTAGTCGATGCGAGCGA

GTCCGATCAGTCCAGGTTTCAAAGTCAAAT-3'.

(SEQ ID NO: 19)
5'-TATTAATACGACTCACTATAGGGGTGCAGTCAGTCCCTCGGTTAAAG

TCTCGAGTCGCTCTGTCAAAATATCCGTACCGTAGTCGATGCGAGCGAGT

CCGATCAGTCCAGGTTTCAAAGTCAA-3'.

(SEQ ID NO: 20)
5'-TATTAATACGACTCACTATAGGGGTGCAGTCAGTCCCTCGGTTAAAG

TCTCGAGTCGCTCTGTCAAAATATCCGTACCGTAGTCGATGCGAGCGAGT

CCGATCAGTCCAGGTTTCAAAGTCAA-3'.

(SEQ ID NO: 21)
5'-TATTAATACGACTCACTATAGGGGTGCAGTCAGTCCCTCGGTTAAAG

TCTCGAGTCGCTCTGTCAAAATATCCGTACCGTAGTCGATGCGAGCGAGT

CCGATCAGTCCAGGTTTCAAAGTCAA-3'.

Example 11—IPC DNA Fluorescent Probe Detection

IPC detection probe(s) may include a radioactive, luminescent, chemiluminescent, fluorescent, enzymatic, magnetic, or spin-resonance label, or combination thereof. Fluorescent labels can include fluorescein (FAM), 6-carboxyfluorescein (6-FAM), or 6-carboxyfluorescein-N-succinimidyl ester (6-FAMSE), VIC™ dye, or the like, or a combination thereof.

Figure 4:
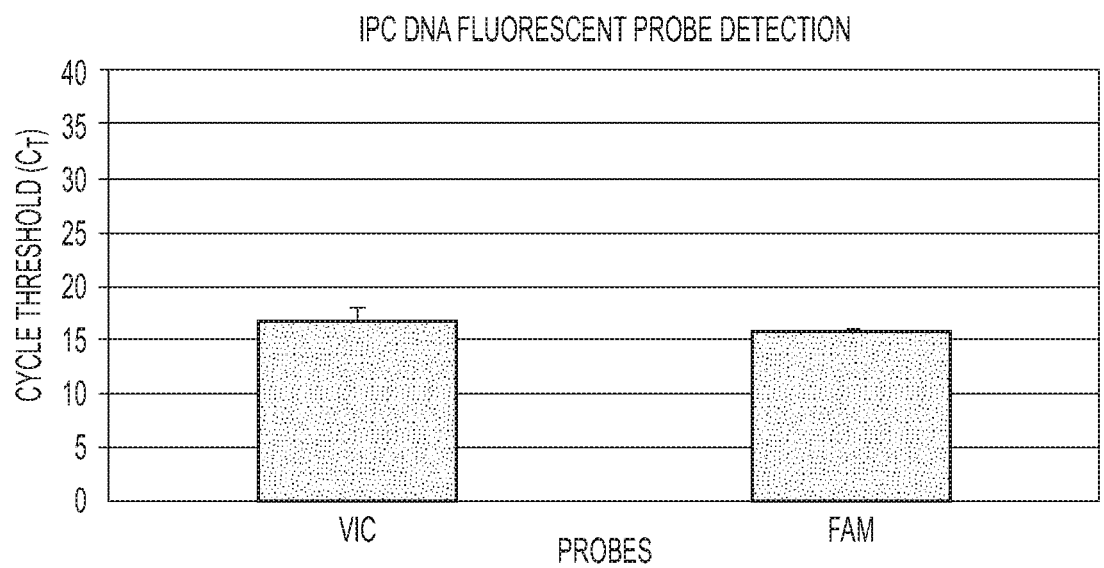
FIG. 4 shows a graph of the RT-PCR analysis when a single stranded DNA internal positive control (IPC) was detected in a PrimeMix® assay using detection probes that were labeled with either 6-FAM (FAM) or VIC™ dye.
Figure 5:
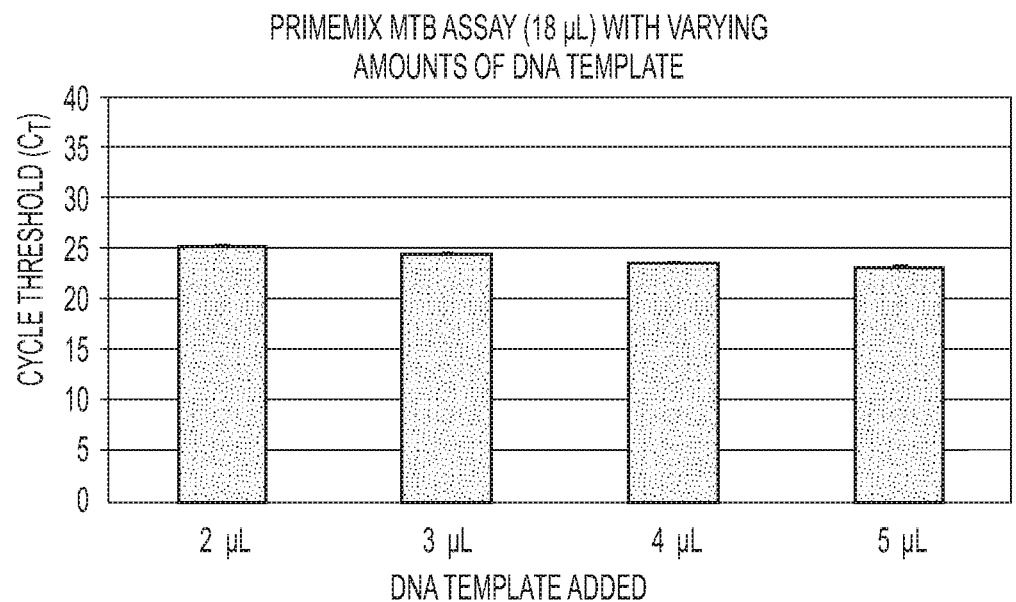
FIG. 5 shows a graph of the RT-PCR analysis when varying amounts of extracted *tuberculosis* patient DNA, i.e., 2 µl, 3 µl, 4 µl, and 5 µl of template DNA, were used in the PrimeMix® Universal MTB Assay.

IPC detection probe (SEQ ID NO:11) was labeled with either 6-FAM (FAM) or VIC™ dye by methods known to one of ordinary skill in the art, in order to evaluate their effect on detection of the IPC in samples, once RT-PCR was performed. PrimeMix® containing these probes as well as the IPC primers (SEQ ID NO:9 and SEQ ID NO:10) was used to amplify and then detect the presence of the IPC. The experiment was performed four times for each type of labeled probe. Detection was performed using the ABI 7500 Fast Real-Time PCR System (Applied Biosystems™, Life Technologies Corporation, Carlsbad, Calif., USA). As can be seen in FIG. 4, there was no significant difference between the $C_\tau$ values for the IPC detection probe labeled with VIC™ dye ($C_\tau$ value=32.5) and that labeled with 6-FAM ($C_\tau$ value=31.5). Thus, the type of probe label used has minimal to no effect in performing the analysis and evaluation of the presence and quantity of the IPC.

Example 12—Multiplex Assay: Internal Positive Control in Combination with the PrimeMix® Universal MTB Assay As noted above, it is desirable to formulate an IPC sequence that is both non-genomic, and that does not significantly hybridize to a mammalian genome, or to the genome of pathogenic species of interest. This is to avoid the possibility of the IPC primers and probes detecting other nucleic acid(s) present in an extracted patient sample, such as DNA from the patient themselves or from other microorganisms that are not of interest that may be present in the sample.

Figure 6:
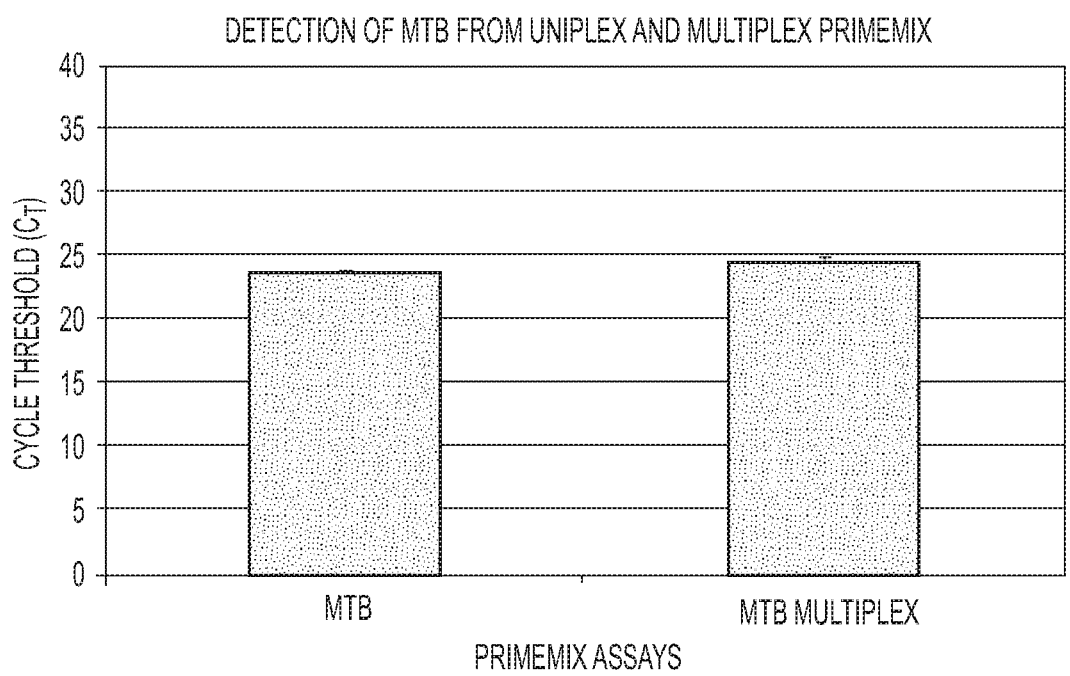
FIG. 6 shows a graph of the RT-PCR analysis when a multiplex PrimeMix® Universal MTB Assay is performed wherein a single stranded DNA internal positive control (IPC) is added to the solution containing the tuberculin sample, as compared to a uniplex assay wherein the initial solution solely contains the biological sample obtained from the patient and the storage solution, i.e., PrimeStore®.

In order to ensure that the IPC, IPC primers and IPC probes of the present invention would not affect or inhibit the amplification or detection of the *M. tuberculosis* sequence in samples, the single stranded DNA IPC was placed into PrimeStore® containing about 33 ng/μL of previously-identified MDR-*M. tuberculosis* DNA. The nucleic acid was then extracted using the QIAamp® DNA Mini Kit (Qiagen®) and PrimeMix® containing both primers and probes for *M. tuberculosis* and the IPC, as described above, were used in a multiplex PrimeMix® Universal MTB Assay. As a comparison, the same procedure was carried out on the same *M. tuberculosis* strain but no IPC, IPC primers or probes were added. This experiment was carried out in triplicate for both the multiplex and uniplex procedure. As can be seen in FIG. 6, the amplification and detection of *M. tuberculosis* nucleic acid was not significantly affected by the multiplex procedure, i.e., the average $C_\tau$ value for the multiplex procedure ("MTB Multiplex") was 24.6 whereas the $C_\tau$ value for the uniplex procedure ("MTB") was 23.6.

In addition to other sequences noted herein, sequences that can be included in preparation of PrimeMix® and/or PrimeStore® include:

SEQ ID NO: 22
TAACCGAGGTCGAAACGTA (Influenza A Forward Primer)

SEQ ID NO: 23
GCACGGTGAGCGTGAA (Influenza A Reverse Primer)

SEQ ID NO: 24
TCAGGCCCCCTCAAAGC (Influenza A Probe)

SEQ ID NO: 25
GGAATTGCAAAGGATGTAATGGAA (Influenza B Forward Primer)

SEQ ID NO: 26
AGAACAAATTGAAAGAATCTGAAATGGT (Influenza B Reverse Primer)

SEQ ID NO: 27
ATGGGAAATTCAGCTCT (Influenza B Probe)

SEQ ID NO: 28
CTCGTCCAGCGCCGCTTC (MTB IS-6110 Forward Primer)

SEQ ID NO: 29
ACAAAGGCCACGTAGGCGA (MTB IS-6100 Reverse Primer)

SEQ ID NO: 30
ACCAGCACCTAACCGGCTGTGGGT (MTB IS-6100 Probe)

SEQ ID NO: 31
AGCGATGAGCGGTCCAATC (MTB IS-1081 Forward Primer)

SEQ ID NO: 32
TGCCCTGGCGCAGCTT (MTB IS-1081 Reverse Primer)

SEQ ID NO: 33
CCGCAACCATCGAC (MTB IS-1081 Probe)

Example 13—Uniplex and Multiplex Assays: Varying Concentrations of IPC

Figure 7:
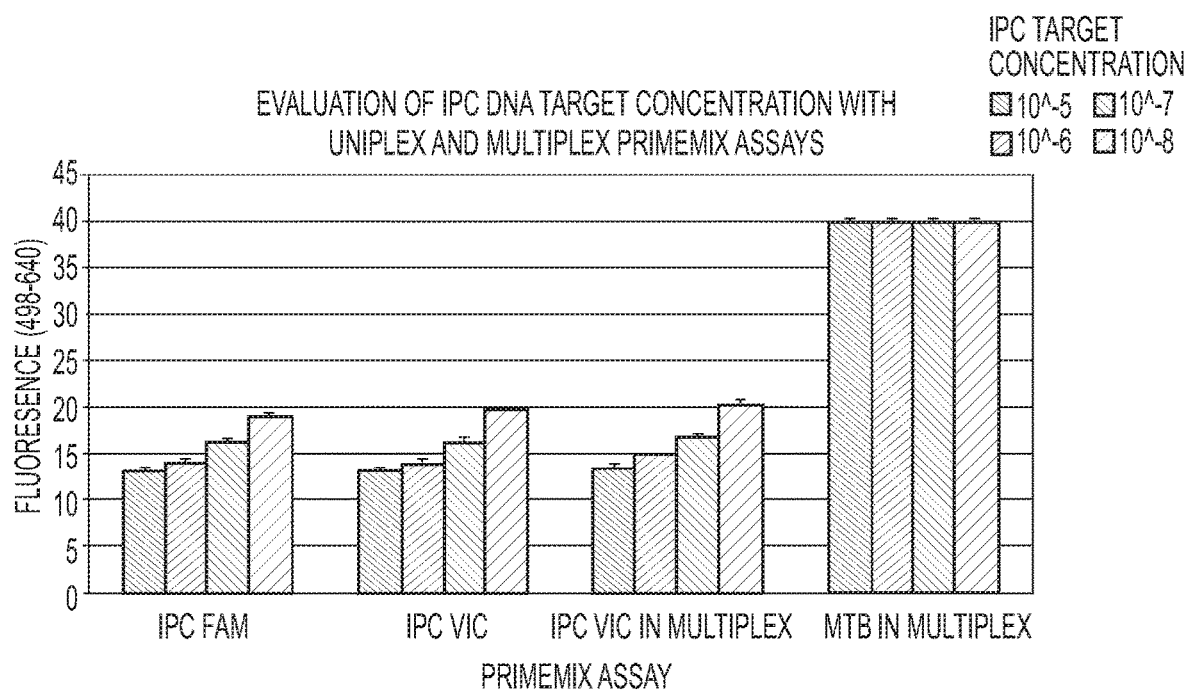
FIG. 7 shows a graph of the RT-PCR analysis when the concentration of the internal positive control ("IPC") placed in PrimeStore® was varied, i.e., $10^{-5}$, $10^{-6}$, $10^{-7}$, and $10^{-8}$ ng/µL of IPC were placed into the same amount of PrimeStore®. The probes for the IPC were either labeled with 6-FAM ("IPC Fam") or VIC™ dye ("IPC Vic"). A multiplex reaction was also carried out, in which *M. tuberculosis* complex-specific primers and probes were also added to the PrimeMix® (results shown in column labeled "MTB in Multiplex"), along with the IPC primers and probes (results shown in column labeled "IPC Vic in Multiplex")
Figure 8:
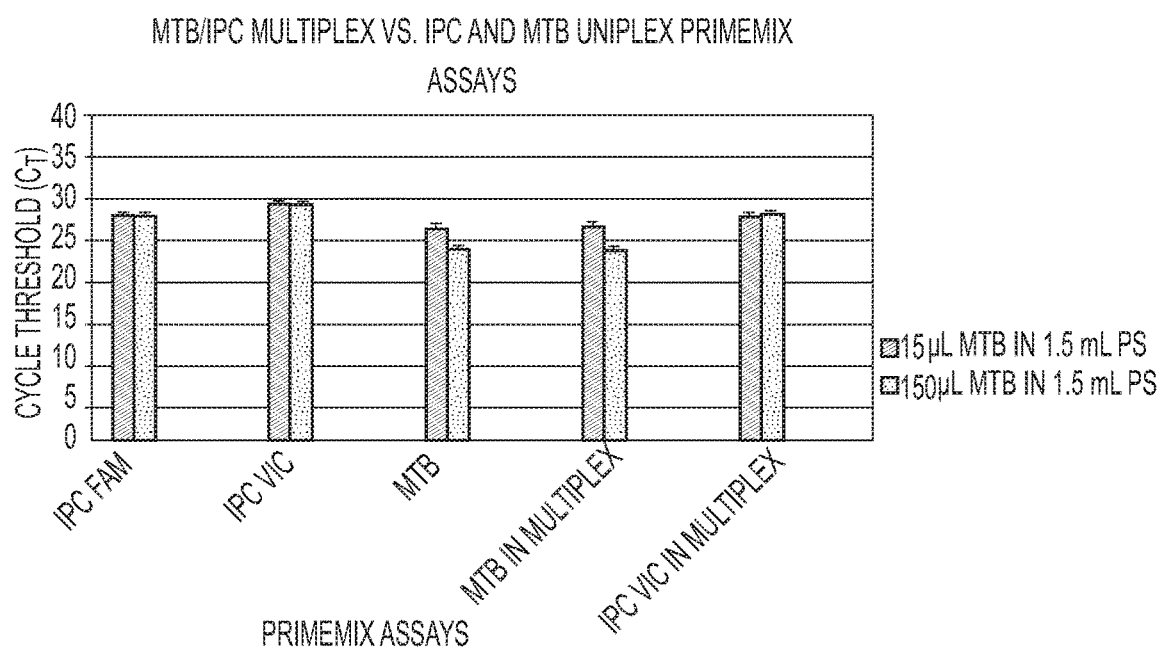
FIG. 8 shows a graph of the RT-PCR analysis when the initial amount of an *M. tuberculosis* sample is 15 µl and 150 µl (a 10-fold difference) when each is initially stored in 1.5 mL of PrimeStore®. This was performed for IPC probes labeled with 6-FAM ("IPC Fam") and VIC™ dye ("IPC Vic"), as well as for uniplex detection of *M. tuberculosis* ("MTB") and multiplex detection of *M. tuberculosis* ("MTB in Multiplex") and the IPC wherein the probe is labeled with VIC™ dye ("IPC Vic in Multiplex")
Figure 9:
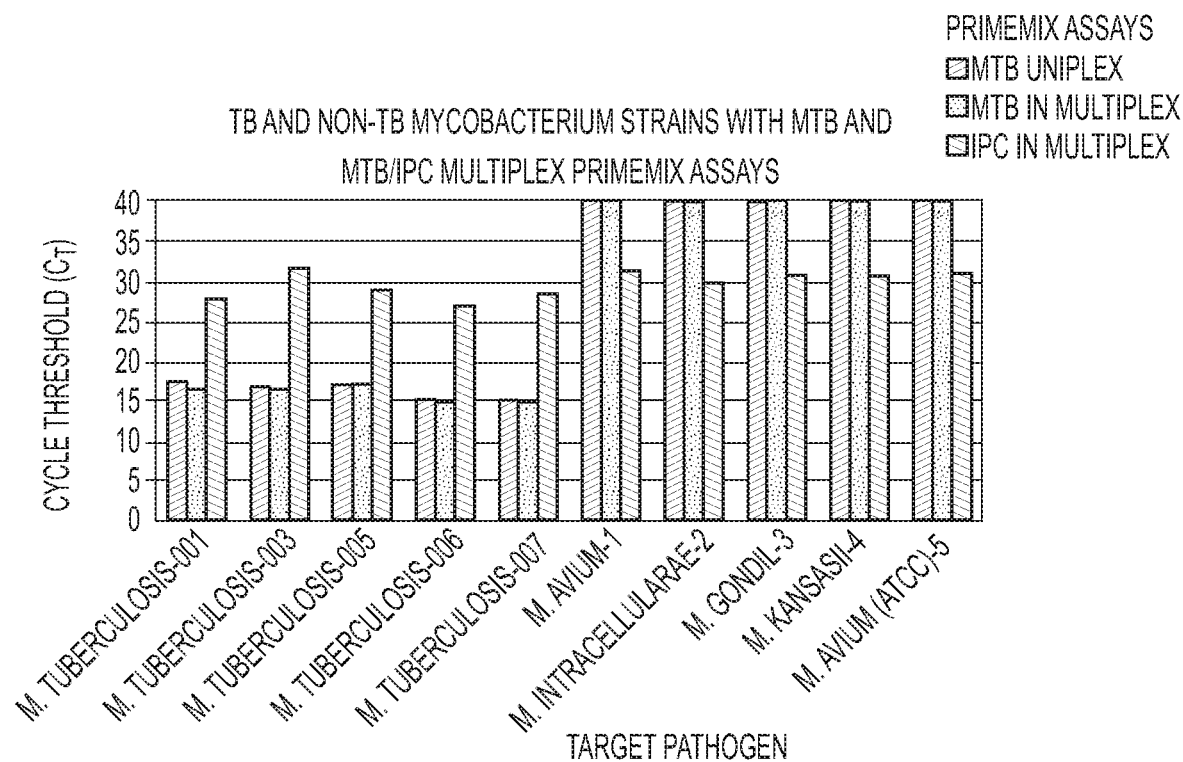
FIG. 9 shows a graph of the RT-PCR analysis when various *mycobacterium* strains, i.e., five different *M. tuberculosis* strains, two different *M. avium* strains, one *M. intracellularae* strain, one *M. gondii* strain, and one *M. kansasii* strain, were placed in and then extracted from PrimeStore® and then analyzed using both the uniplex ("MTB Uniplex") and multiplex ("MTB in Multiplex") formats of the PrimeMix® procedure. The uniplex assay used only *M. tuberculosis* complex-specific primers and probes, whereas the multiplex assay used both *M. tuberculosis* complex-specific primers and probes and IPC-specific primers and probes.
Figure 10:
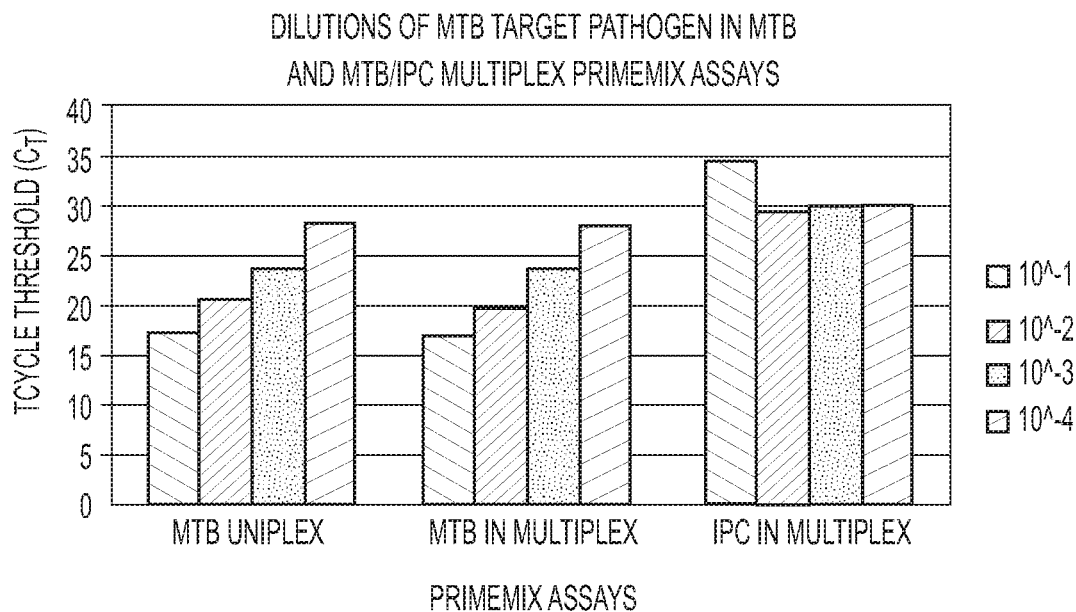
FIG. 10 shows a graph of the RT-PCR analysis when the amount of *M. tuberculosis* from a particular purified strain is varied, i.e., $10^{-4}$, $10^{-3}$, $10^{-2}$, $10^{-1}$ are representative of ten-fold dilutions wherein $10^{-1}$ represents a DNA concentration of 330 ng/µL, $10^{-2}$ represents a DNA concentration of 33 ng/µL, $10^{-3}$ represents a DNA concentration of 3.3 ng/µL and $10^{-4}$ represents a DNA concentration of 0.33 ng/µL. A uniplex reaction using PrimeMix® Universal MTB Assay with *M. tuberculosis* complex-specific primers and probes was performed (results shown in "MTB Uniplex" column"), as well as a multiplex PrimeMix® assay in which both *M. tuberculosis* complex-specific primers and probes and IPC-specific primers and probes were present was performed (results shown in "MTB in Multiplex" and "IPC in Multiplex" columns)
Figure 11:
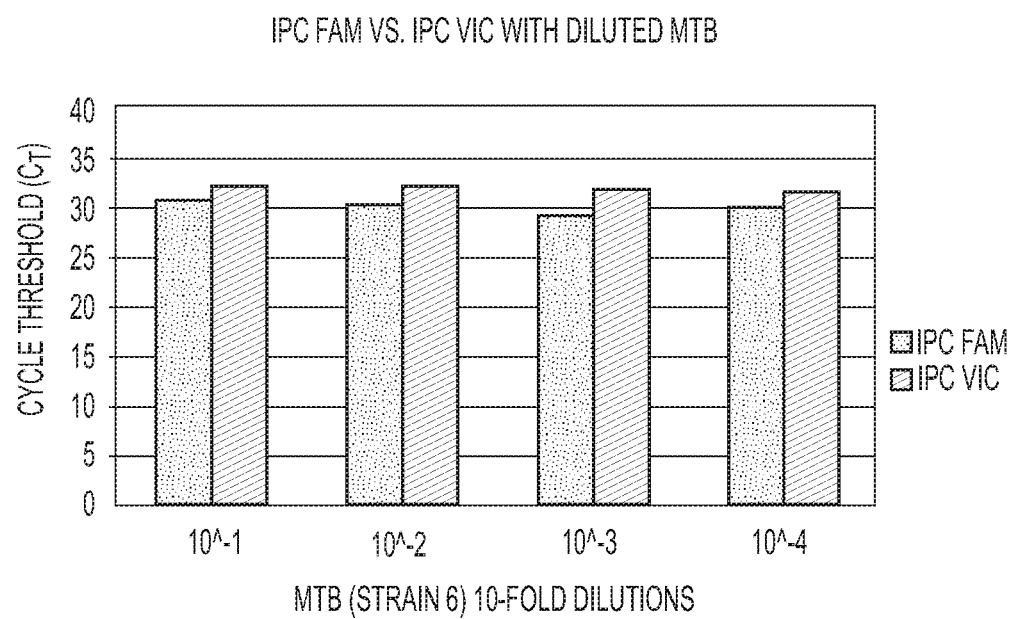
FIG. 11 shows a graph of the RT-PCR analysis when the amount of *M. tuberculosis* from a particular purified strain is varied, i.e., $10^{-4}$, $10^{-3}$, $10^{-2}$, $10^{-1}$ are representative of ten-fold dilutions wherein $10^{-1}$ represents a DNA concentration of 33 ng/μL, $10^{-2}$ represents a DNA concentration of 3.3 ng/μL, $10^{-3}$ represents a DNA concentration of 0.33 ng/μL and $10^{-4}$ represents a DNA concentration of 0.033 ng/μL and different labels, either 6-FAM ("IPC Fam") or VIC™ dye ("IPC Vic") on the IPC-specific probe were used.

The concentration of the IPC placed in PrimeStore® was varied. $10^{-5}$, $10^{-6}$, $10^{-7}$, and $10^{-8}$ ng/μL of IPC were placed into the same amount of PrimeStore®. Depending on whether a uniplex or multiplex reaction was performed, an *M. tuberculosis* complex-specific set of primers and probe were also placed in the PrimeMix®. No *M. tuberculosis* complex-specific nucleic acids were added to the PrimeStore® solution. As can be seen in FIG. 7, varying the concentration of the IPC in PrimeStore® in a multiplex PrimeMix® Universal MTB Assay ("IPC Vic in Multiplex") showed no significant difference when compared to the same concentration variations of IPC in the uniplex PrimeMix® assay (for IPC only) ("IPC Fam" and "IPC Vic"). Additionally, there were no significant differences between the IPC probes labeled with 6-FAM and those labeled with VIC™ dye in a uniplex format when IPC concentration was varied.

Example 14—Uniplex and Multiplex Assays: Varying Concentrations of *M. tuberculosis* Sample As can be seen in FIG. 8, increasing the initial amount of *M. tuberculosis* sample from 15 μL to 150 μL (a 10-fold difference) as initially stored in 1.5 mL of PrimeStore®, slightly improves the results obtained from a uniplex PrimeMix® Universal MTB Assay (average $C_\tau$ value of 15 μL sample=26.5, average $C_\tau$ value of 150 μL sample=24.1) and a multiplex PrimeMix® Universal MTB Assay (average $C_\tau$ value of 15 μL sample=26.8, average $C_\tau$ value of 150 μL sample=24.2). Detection of the IPC remains unaffected as expected. There was little observable difference in MTB PCR amplification, as measured by $C_\tau$ scores between the uniplex and multiplex PrimeMix® Universal MTB Assay.

Example 15—Uniplex and Multiplex Assays: Detection of *Mycobacterium* Strains

Various mycobacterial strains (i.e., five different *M. tuberculosis* strains, two different *M. avium* strains, one *M. intracellularae* strain, one *M. gondii* strain, and one *M. kansasii* strain) were tested using both the uniplex ("MTB Uniplex") and multiplex ("MTB in Multiplex") PrimeMix® by similar procedures to those described above. Nucleic extraction amounts varied, depending on the contents of the sputum sample from about 80 to about 180 ng/μL. As can be seen in FIG. 9, both the uniplex and multiplex assays readily detected the five different *M. tuberculosis* strains but not the other non-MTB strains. This indicates that the PrimeMix® assay readily detects *tuberculosis*-causing organisms and not other *Mycobacterium* species. No significant difference was detected between the results for the uniplex and multiplex assays for MTB detection indicating little to no loss of sensitivity between uniplex and multiplex assays. The IPC was readily detected in all multiplex assays, regardless of what mycobacterial strain was used.

Example 16—Uniplex and Multiplex Assays: Dilution of *M. tuberculosis* Target Pathogen As can be seen in FIG. 10, varying the amount of *M. tuberculosis* target sequence concentration from a particular purified strain, i.e., $10^{-4}$, $10^{-3}$, $10^{-2}$, $10^{4}$ are representative of ten-fold dilutions wherein $10^{-1}$ represents a DNA concentration of 330 ng/μL, $10^{-2}$ represents a DNA concentration of 33 ng/μL, $10^{-3}$ represents a DNA concentration of 3.3 ng/μL and $10^{-4}$ represents a DNA concentration of 0.33 ng/μL, increased the ability of the PrimeMix® assay to detect *M. tuberculosis* significantly, in both the uniplex and multiplex assays. The IPC target sequence concentration was 0.02 pg/mL for each assay. IPC detection was minimally affected by the highest concentration of *M. tuberculosis* nucleic acid, as typically expected in the performance of multiplex assays where the concentration of a target sequence is generally much higher than that of the IPC target. This could be addressed by increasing the concentration of the IPC target sequence in the assay or further molar optimization of the IPC primers and/or probe in the multiplex reaction.

Example 17—Multiplex Assays: Dilution of *M. tuberculosis* Strain

As can be seen in FIG. 11, varying the amount of *M. tuberculosis* nucleic acid from a particular purified strain, i.e., $10^{-4}$, $10^{-3}$, $10^{-2}$, $10^{-1}$ are representative of ten-fold dilutions wherein $10^{-4}$ represents a DNA concentration of 33 ng/μL, $10^{-2}$ represents a DNA concentration of 3.3 ng/μL, $10^{-3}$ represents a DNA concentration of 0.33 ng/μL and $10^{-4}$ represents a DNA concentration of 0.033 ng/μL, had no significant effect on the detection of the IPC when using IPC probes labeled with either 6-FAM or VIC™ dye. Probes labeled with 6-FAM did show lower $C_\tau$ values overall, but both methods of detection were equally effective.

Example 18—Variation in Real-Time PCR Cycle Threshold at Various BSA Concentrations PCR DNA and/or RNA enzymes and 10×PCR buffers are typically supplied in separate tubes and maintained at a constant −20 Celsius. "Master Mix" preparations are typically prepared by thawing and combining the enzyme and 10×PCR buffer with primers for amplification. The present invention is an all-inclusive blend that includes buffers, salts, enzymes, and primers and probe for real-time amplification from a 1× single-use tube that is considerably more thermostable than PCR buffers in the art. For example, in contrast to commercial 10×PCR buffer supplied with Platinum Taq DNA Polymerase (Invitrogen, Cat #s 10966-018 and 10966-026), the present invention includes the addition of BSA for stabilizing PCR enzymes in the reaction.

Bovine Serum Albumin (BSA) is used commonly in restriction enzyme reactions to stabilize some enzymes during digestion of DNA and to prevent adhesion of enzyme to reaction tubes, particularly glass capillary tubes used for PCR. Because of its stabilizing characteristics in extended, i.e., overnight restriction enzymatic reactions, BSA may likewise enhance the stability and integrity of DNA and RNA polymerases used in PCR and RT-PCR amplifications, especially when these enzymes are stored at temperatures less than −20 Celsius. BSA is reported to stabilize reactions by interfering with inhibiting substances and DNA contaminants. The presence of BSA at concentrations between 0.1-0.5 mg/mL in final reaction concentrations has no deleterious effect on downstream polymerase chain reactions (PCR) as determined by real-time PCR cycle threshold values.

Betaine improves co-amplification of two alternatively spliced variants of prostate-specific membrane antigen mRNA and amplification of cDNA of c-jun. Betaine and cationic functionalized zwitterionic compounds improves gene amplification by reducing the formation of secondary structure caused by GC-rich regions and, therefore, may be generally applicable to improve amplification of any GC-rich DNA sequence. Betaine in PrimeMix preserves and stabilizes individual nucleotides (A, T, C, G) and prevents annealing, stability, hydrolysis and oxidative degradation of PCR primers and probes in the PrimeMix solutions. Betaine present at a final concentration between 10-100 mM had an additive effect on PCR amplification as determined by cycle threshold during real-time amplification. Betaine is a stabilized molecule and well suited for PCR reaction mixtures held at temperatures greater than minus 20 Celsius because it does not promote nucleotide mutation rate during amplification and it does not degrade as readily as DTT and DMSO.

The final pH of the buffer has a huge impact on the overall stability during PCR amplification. The preferred pH for PCR is typically reported at 8.4, although buffers as basic as 9.0 have been effective. In the current invention containing an all inclusive mix of enzymes, buffers and primers we have found the optimal pH to be 8.2 (+/−0.1). A slightly less basic buffer was shown to enhance PCR amplification by real-time PCR, specifically when PrimeMix formulations are held over time at temperatures greater than minus 20 Celsius.

Figure 12:
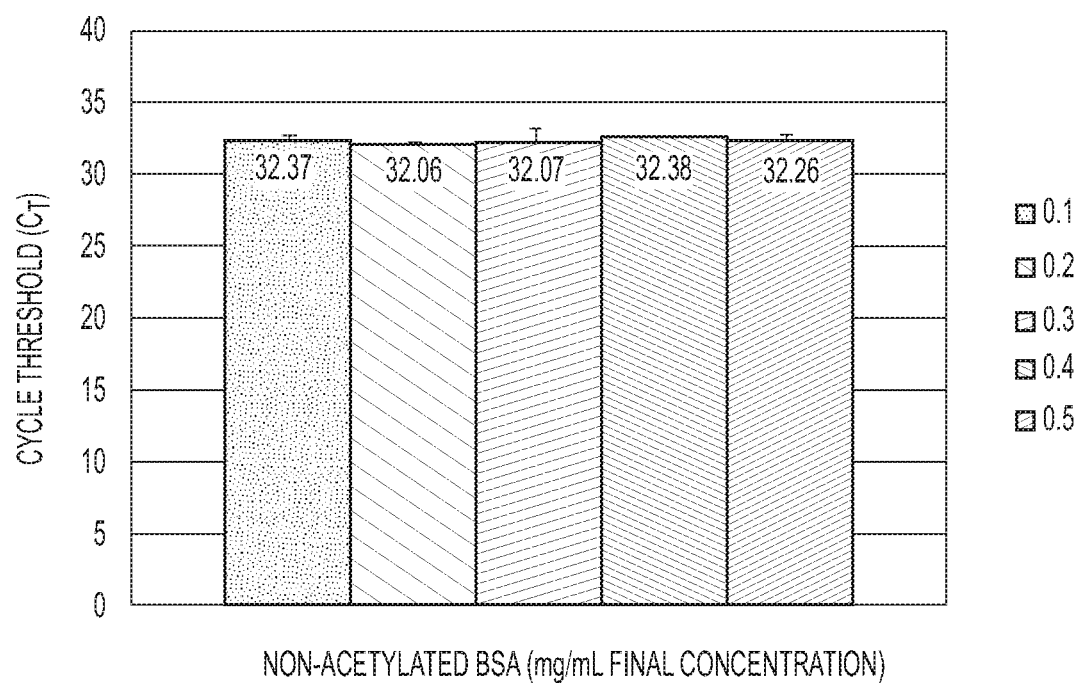
FIG. 12 shows a chart comparing non-acetylated BSA (mg/mL final concentration) vs. cycle threshold (CT).

Influenza A ($H_3N_2$) virus ($10^2$ $TCID_{50}$/mL) was amplified using PrimeMix Universal Influenza A in a 0.1-0.5 mg/mL gradient of BSA (see FIG. 12). As can be seen, there was no variation in real-time PCR cycle threshold noted at these concentrations indicating no PCR inhibition by BSA.

Other embodiments and uses of the invention will be apparent to those skilled in the art from consideration of the specification and practice of the invention disclosed herein. All references cited herein, including all publications, U.S. and foreign patents and patent applications, and all priority documents are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the claims.

The invention claimed is:

1. A PCR ready composition comprising an aqueous mixture of:
   RNase-free water;
   a buffer at a concentration of at least 50 mM;
   forward and reverse amplification primers specific for PCR amplification of a target nucleic acid sequence;
   a plurality of nucleotides sufficient for PCR amplification of the target nucleotide sequence;
   a PCR polymerase enzyme and/or a reverse transcriptase; and
   a nucleic acid probe that consists of at least a sequence selected from the group of sequences consisting of SEQ ID NO 6, SEQ ID NO 7, and SEQ ID NO: 33, wherein the primers, the plurality of nucleotides and the enzyme remain stable in the mixture for at least 5 days at ambient temperature.

2. The composition of claim 1, wherein the buffer comprises tris(hydroxymethyl) aminomethane (Tris), citrate, 2-(N-morpholino)ethanesulfonic acid (MES), N,N-Bis(2-hydroxyethyl)-2-aminoethanesulfonic acid (BES), 1,3-bis(tris(hydroxymethyl) methylamino)propane (Bis-Tris), 4-(2-hydroxyethyl)-1-piperazineethanesulfonic acid (HEPES), 3-(N-morpholino)propanesulfonic acid (MOPS), N,N-bis(2-hydroxyethyl) glycine (Bicine), N-[tris(hydroxymethyl) methyl]glycine (Tricine), N-2-acetamido-2-iminodiacetic acid (ADA), N-(2-acetamido)-2-aminoethanesulfonic acid (ACES), piperazine-1,4-bis(2-ethanesulfonic acid) (PIPES), bicarbonate, phosphate, and any combination thereof, present in the composition at a concentration of from about 50 mM to about 1 M, and with a selected pH of about 6.5 to about 9.0.

3. The composition of claim 1, wherein the forward and reverse amplification primers comprise primer sequences for PCR amplification of a viral sequence.

4. The composition of claim 3, wherein the viral sequence comprises a sequence of influenza virus.

5. The composition of claim 1, wherein the forward and reverse amplification primers comprise primer sequences for PCR amplification of a bacterial sequence.

6. The composition of claim 5, wherein the bacterial sequence is a sequence of Mycobacteria.

7. The composition of claim 1, wherein the target nucleic acid sequence is a viral, bacterial, parasitic or fungal sequence.

8. The composition of claim 7, wherein the viral sequence is a sequence of influenza virus or the bacterial sequence is a sequence of Mycobacteria.

9. The composition of claim 1, wherein the primers, the plurality of nucleotides and the enzyme remain stable for at least a month.

10. The composition of claim 1, wherein the selected pH is within one pH unit of the pKa of the buffer, within 0.5 pH units of the pKa of the buffer, or within 0.2 pH units of the pKa of the buffer at ambient temperature.

11. The composition of claim 1, wherein the nucleic acid probe hybridizes to a PCR amplification product of the target nucleic acid.

12. The composition of claim 1, further comprising a positive and/or negative control sequence.

13. The composition of claim 1, further comprising the target nucleic acid sequence.

14. The composition of claim 1, further comprising a PCR amplification product of the target nucleic acid.

15. The composition of claim 1, further comprising a chelating agent.

16. The composition of claim 15, wherein the chelating agent comprises ethylene glycol tetraacetic acid, hydroxyethylethylenediaminetriacetic acid, diethylene triamine pentaacetic acid, N,N-bis(carboxymethyl)glycine, ethylenediaminetetraacetic, citrate anhydrous, sodium citrate, calcium citrate, ammonium citrate, ammonium bicitrate, citric acid, diammonium citrate, potassium citrate, magnesium citrate, ferric ammonium citrate, lithium citrate, or a combination thereof, present in the composition at a concentration of about 0.01 mM to about 1 mM.

17. The composition of claim 1, further comprising an osmolarity agent.

18. The composition of claim 17, wherein the osmolarity agent comprises N,N,N-trimethylglycine (betaine), dimethyl sulfoxide (DMSO), formamide, glycerol, non-ionic detergents, polyethylene glycol, tetramethylammonium chloride, or a combination thereof, present in the composition at a concentration of about 1 mM to about 1 M.

19. The composition of claim 1, further comprising an albumin.

20. The composition of claim 19, wherein the albumin comprises bovine serum albumin, human serum albumin, goat serum albumin, mammalian albumin, or a combination thereof, present in the composition at a concentration of about 5 ng/ml to about 100 ng/ml.

21. The composition of claim 1, further comprising a salt.

22. The composition of claim 21, wherein the salt comprises magnesium sulfate, magnesium chloride, potassium chloride, potassium glutamate or a combination thereof, present in the composition at a concentration of about 50 mM to about 1 M.

23. The composition of claim 1, further comprising a dye.

24. The composition of claim 23, wherein the dye comprises fluorescein, 5-carboxy-X-rhodamine, ROX or a combination thereof, present in the composition at a concentration of about 0.01 mM to 50 mM.

25. A PCR-ready composition comprising as components:
   a buffer present in the composition at a concentration of at least 50 mM to about 1 M and with a pH of from about 6.5 to about 9.0;
   a chelating agent present in the composition at a concentration of about 0.01 mM to about 1 mM;
   an osmolarity agent present in the composition at a concentration of about 1 mM to about 1 M;
   an albumin present in the composition at a concentration of from about 5 ng/ml to about 100 ng/ml;
   a salt present in the composition at a concentration of from about 50 mM to about 1 M;
   a dye present in the composition at a concentration of from about 0.01 mM to 50 mM;
   forward and reverse amplification primers specific for PCR amplification of a target nucleic acid sequence;
   a plurality of nucleotides sufficient for PCR amplification of the target nucleotide sequence; and a PCR polymerase and/or a reverse transcriptase; and
a nucleic acid probe consisting of a sequence selected from the group of sequences consisting of SEQ ID NO: 6, SEQ ID NO: 7, and SEQ ID NO: 33, wherein:
the components are combined in nuclease-free water; and
the primers, the plurality of nucleotides and the enzyme remain stable in the mixture for at least 5 days at ambient temperature.

26. The composition of claim 25, wherein:
the buffer comprises tris(hydroxymethyl) aminomethane (Tris), citrate, 2-(N-morpholino)ethanesulfonic acid (MES), N,N-Bis(2-hydroxyethyl)-2-aminoethanesulfonic acid (BES), 1,3-bis(tris(hydroxymethyl) methylamino)propane (Bis-Tris), 4-(2-hydroxyethyl)-1-piperazineethanesulfonic acid (HEPES), 3-(N-morpholino)propanesulfonic acid (MOPS), N,N-bis(2-hydroxyethyl) glycine (Bicine), N-[tris(hydroxymethyl)methyl]glycine (Tricine), N-2-acetamido-2-iminodiacetic acid (ADA), N-(2-acetamido)-2-aminoethanesulfonic acid (ACES), piperazine-1,4-bis(2-ethanesulfonic acid) (PIPES), bicarbonate, phosphate, and any combination thereof;
the chelating agent comprises ethylene glycol tetraacetic acid, hydroxyethylethylenediaminetriacetic acid, diethylene triamine pentaacetic acid, N,N-bis(carboxymethyl)glycine, ethylenediaminetetraacetic, citrate anhydrous, sodium citrate, calcium citrate, ammonium citrate, ammonium bicitrate, citric acid, diammonium citrate, potassium citrate, magnesium citrate, ferric ammonium citrate, lithium citrate, or a combination thereof;
the osmolarity agent comprises N,N,N-trimethylglycine (betaine), dimethyl sulfoxide (DMSO), foramide, glycerol, non-ionic detergents, polyethylene glycol, tetramethylammonium chloride, or a combination thereof;
the albumin comprises bovine serum albumin, human serum albumin, goat serum albumin, mammalian albumin, or a combination thereof;
the salt comprises magnesium sulfate, magnesium chloride, potassium chloride, potassium glutamate or a combination thereof; or
the dye comprises fluorescein, 5-carboxy-X-rhodamine, ROX or a combination thereof.

27. The composition of claim 25, wherein the PCR polymerase enzyme comprises Taq polymerase, Pfu polymerase, KOD polymerase, hot-start polymerase, next-gen polymerase, RT-polymerase or a combination thereof.

28. The composition of claim 25, wherein the selected pH is within one pH unit of the pKa of the buffer, within 0.5 pH units of the pKa of the buffer, or within 0.2 pH units of the pKa of the buffer at ambient temperature.

29. The composition of claim 25, wherein the nucleic acid probe hybridizes to a PCR amplification product of the target nucleic acid.

30. The composition of claim 25, further comprising a positive and/or negative control sequence.

31. The composition of claim 25, further comprising the target nucleic acid sequence.

32. The composition of claim 31, wherein the target nucleic acid sequence comprises a viral or bacterial sequence.

33. The composition of claim 31, wherein the target nucleic sequence comprises a sequence of influenza virus or a sequence of Mycobacteria.

34. The composition of claim 25, further comprising a PCR amplification product or reverse transcription product of the target nucleic acid.

35. The composition of claim 25, wherein the primers, the plurality of nucleotides and the enzyme remain stable for at least a month.

36. The composition of claim 25, wherein the primers comprise at least 95% of the sequence of the group of sequence pairs consisting of SEQ ID NO: 22 and SEQ ID NO: 23, SEQ ID NO: 25 and SEQ ID NO: 26; the sequence of SEQ ID NO: 28 and SEQ ID NO: 29, and SEQ ID NO: 31 and SEQ ID NO: 32.

37. A PCR-ready composition comprising as components:
a buffer present in the composition at a concentration of at least 50 mM to about 1 M and with a pH of from about 6.5 to about 9.0;
a chelating agent present in the composition at a concentration of about 0.01 mM to about 1 mM;
forward and reverse amplification primers specific for PCR amplification of a target nucleic acid sequence;
a plurality of nucleotides sufficient for PCR amplification of the target nucleotide sequence;
at least two salts collectively present in the composition at a concentration of about 50 mM to about 10 M;
albumin present in the composition at a concentration of about 5 ng/ml to about 1 mg/ml;
a non-ionic detergent, a glycerol and betaine collectively present in the composition at a concentration of about 1 mM to about 1 M;
a dye present in the composition at about 0.01 µM to about 1 µM;
a PCR polymerase enzyme and/or a reverse transcriptase; and
a nucleic acid probe consisting of a sequence selected from the group of sequences consisting of SEQ ID NO: 6, SEQ ID NO: 7, and SEQ ID NO: 33, wherein:
the components are combined in nuclease-free water; and
the primers, the plurality of nucleotides and the enzyme remain stable in the mixture for at least 5 days at ambient temperature.

38. The composition of claim 37, wherein:
the buffer comprises tris(hydroxymethyl) aminomethane (Tris), citrate, 2-(N-morpholino)ethanesulfonic acid (MES), N,N-Bis(2-hydroxyethyl)-2-aminoethanesulfonic acid (BES), 1,3-bis(tris(hydroxymethyl) methylamino)propane (Bis-Tris), 4-(2-hydroxyethyl)-1-piperazineethanesulfonic acid (HEPES), 3-(N-morpholino)propanesulfonic acid (MOPS), N,N-bis(2-hydroxyethyl) glycine (Bicine), N-[tris(hydroxymethyl)methyl]glycine (Tricine), N-2-acetamido-2-iminodiacetic acid (ADA), N-(2-acetamido)-2-aminoethanesulfonic acid (ACES), piperazine-1,4-bis(2-ethanesulfonic acid) (PIPES), bicarbonate, phosphate, and any combination thereof;
the chelating agent comprises ethylene glycol tetraacetic acid, hydroxyethylethylenediaminetriacetic acid, diethylene triamine pentaacetic acid, N,N-bis(carboxymethyl)glycine, ethylenediaminetetraacetic, citrate anhydrous, sodium citrate, calcium citrate, ammonium citrate, ammonium bicitrate, citric acid, diammonium citrate, potassium citrate, magnesium citrate, ferric ammonium citrate, lithium citrate, or a combination thereof;
the at least two salts one or more of comprise magnesium sulfate, magnesium chloride, potassium chloride, potassium glutamate or a combination thereof;
the albumin comprises bovine serum albumin, human serum albumin, goat serum albumin, mammalian albumin, or a combination thereof; or the dye comprises fluorescein, 5-carboxy-X-rhodamine, ROX or a combination thereof.

39. The composition of claim 37, wherein the primers, the plurality of nucleotides and the enzyme remain stable for at least a month.

40. The composition of claim 37, wherein the selected pH is within one pH unit of the pKa of the buffer, within 0.5 pH units of the pKa of the buffer or within 0.2 pH units of the pKa of the buffer at ambient temperature.

41. The composition of claim 37, wherein the nucleic acid probe hybridizes to a PCR amplification product of the target nucleic acid.

42. The composition of claim 37, further comprising a positive and/or negative control sequence.

43. The composition of claim 37, further comprising the target nucleic acid sequence.

44. The composition of claim 37, further comprising a PCR amplification product or reverse transcription product of the target nucleic acid.

45. The composition of claim 23, wherein:
the buffer is present in the composition with a pH of from about 6.5 to about 9.0; and
the dye is present in the composition at a concentration of from about 0.01 mM to 50 mM.

46. The composition of claim 45, further comprising:
a chelating agent present in the composition at a concentration of about 0.01 mM to about 1 mM;
an osmolarity agent present in the composition at a concentration of about 1 mM to about 1 M; and
an albumin present in the composition at a concentration of from about 5 ng/ml to about 100 ng/ml.

* * * * *